US010849849B2

(12) United States Patent
Eng-Wong et al.

(10) Patent No.: US 10,849,849 B2
(45) Date of Patent: Dec. 1, 2020

(54) SUBCUTANEOUS HER2 ANTIBODY FORMULATIONS

(71) Applicants: Genentech, Inc., South San Francisco, CA (US); F. Hoffmann-La Roche AG, Basel (CH)

(72) Inventors: Jennifer Eng-Wong, South San Francisco, CA (US); Whitney Kirschbrown, South San Francisco, CA (US); Tarik Khan, Basel (CH); Jasper Lin, South San Francisco, CA (US); Sreedhara Alavattam, South San Francisco, CA (US); Amit Garg, South San Francisco, CA (US); Sarah Heeson, Welwyn Garden (GB); Tanja Badovinac-Crnjevic, Basel (CH); Christine Wurth, Basel (CH)

(73) Assignees: GENENTECH INC., South San Francisco, CA (US); HOFFMANN-LA ROCHE INC, Little Falls, NJ (US)

( * ) Notice: Subject to any disclaimer, the term of this patent is extended or adjusted under 35 U.S.C. 154(b) by 200 days.

(21) Appl. No.: 15/872,648

(22) Filed: Jan. 16, 2018

(65) Prior Publication Data

US 2018/0296470 A1 Oct. 18, 2018

Related U.S. Application Data

(60) Provisional application No. 62/447,359, filed on Jan. 17, 2017.

(51) Int. Cl.
| | | |
|---|---|---|
| C07K 16/28 | (2006.01) | |
| C07K 16/30 | (2006.01) | |
| C07K 16/32 | (2006.01) | |
| A61K 39/395 | (2006.01) | |
| A61K 9/00 | (2006.01) | |
| A61K 47/18 | (2017.01) | |
| A61K 47/26 | (2006.01) | |
| A61K 47/20 | (2006.01) | |
| A61K 39/00 | (2006.01) | |
| A61P 35/00 | (2006.01) | |
| A61K 9/08 | (2006.01) | |
| A61K 38/47 | (2006.01) | |

(52) U.S. Cl.
CPC .............. *A61K 9/0019* (2013.01); *A61K 9/08* (2013.01); *A61K 38/47* (2013.01); *A61K 39/001106* (2018.08); *A61K 39/39591* (2013.01); *A61K 47/183* (2013.01); *A61K 47/20* (2013.01); *A61K 47/26* (2013.01); *A61P 35/00* (2018.01); *C07K 16/32* (2013.01); *C12Y 302/01035* (2013.01); *A61K 2039/505* (2013.01); *A61K 2039/507* (2013.01); *A61K 2039/54* (2013.01); *A61K 2039/545* (2013.01); *A61K 2039/585* (2013.01); *C07K 16/28* (2013.01); *C07K 16/30* (2013.01); *C07K 2317/24* (2013.01); *C07K 2317/56* (2013.01); *C07K 2317/90* (2013.01)

(58) Field of Classification Search
CPC ............ A61K 9/0019; A61K 39/39558; A61K 2039/507
See application file for complete search history.

(56) References Cited

U.S. PATENT DOCUMENTS

| | | | |
|---|---|---|---|
| 4,968,603 | A | 6/1990 | Slamon et al. |
| 5,648,237 | A | 7/1997 | Carter |
| 5,677,171 | A | 10/1997 | Hudziak et al. |
| 5,720,937 | A | 2/1998 | Hudziak et al. |
| 5,720,954 | A | 2/1998 | Hudziak et al. |
| 5,770,195 | A | 6/1998 | Hudziak et al. |
| 5,772,997 | A | 6/1998 | Hudziak et al. |
| 5,725,856 | A | 10/1998 | Hudziak et al. |
| 5,821,337 | A | 10/1998 | Carter et al. |
| 6,015,567 | A | 1/2000 | Hudziak et al. |
| 6,127,526 | A | 3/2000 | Blank |
| 6,054,297 | A | 4/2000 | Carter et al. |
| 6,165,464 | A | 12/2000 | Hudziak et al. |
| 6,267,958 | B1 | 7/2001 | Andya et al. |
| 6,333,169 | B1 | 12/2001 | Hudziak et al. |
| 6,333,398 | B1 | 12/2001 | Blank |
| 6,339,142 | B1 | 1/2002 | Basey et al. |
| 6,489,447 | B1 | 3/2002 | Basey et al. |
| 6,399,063 | B1 | 4/2002 | Hudziak et al. |
| 6,387,371 | B1 | 5/2002 | Hudziak et al. |
| 6,407,213 | B1 | 6/2002 | Carter et al. |
| 6,417,335 | B1 | 9/2002 | Basey et al. |
| 6,573,043 | B1 | 3/2003 | Cohen et al. |
| 6,627,196 | B1 | 9/2003 | Baughman et al. |
| 6,632,979 | B2 | 10/2003 | Erickson et al. |
| 6,639,055 | B1 | 10/2003 | Carter et al. |
| 6,695,940 | B2 | 2/2004 | Devoe et al. |
| 6,685,940 | B2 | 3/2004 | Andya et al. |
| 6,719,971 | B1 | 4/2004 | Carter et al. |
| 6,800,738 | B1 | 5/2004 | Carter et al. |
| 6,797,814 | B2 | 9/2004 | Blank |
| 6,821,151 | B2 | 11/2004 | Lai et al. |
| 6,821,515 | B1 | 11/2004 | Cleland et al. |

(Continued)

FOREIGN PATENT DOCUMENTS

| | | |
|---|---|---|
| WO | 97/04801 A1 | 2/1997 |
| WO | 99/31140 A1 | 6/1999 |

(Continued)

OTHER PUBLICATIONS

Wynne et al., J. Clin. Pharmacol., 2013, 53(2): 192-201.*

(Continued)

*Primary Examiner* — Hong Sang
(74) *Attorney, Agent, or Firm* — Wendy M. Lee

(57) ABSTRACT

Fixed dose HER2 antibody formulations for subcutaneous administration are provided along with their use in the treatment of cancer. The formulations include fixed dose subcutaneous formulations of pertuzumab and subcutaneous co-formulations of pertuzumab and trastuzumab, and their use in the treatment of cancer.

28 Claims, 33 Drawing Sheets

Specification includes a Sequence Listing.

(56) References Cited

U.S. PATENT DOCUMENTS

| | | |
|---|---|---|
| 6,905,830 B2 | 6/2005 | Cohen et al. |
| 6,949,245 B1 | 9/2005 | Sliwkowski |
| 7,018,809 B1 | 3/2006 | Carter |
| 7,060,268 B2 | 6/2006 | Andya et al. |
| 7,097,840 B2 | 8/2006 | Erickson et al. |
| 7,041,292 B1 | 9/2006 | Sliwkowski |
| 6,984,494 B2 | 10/2006 | Ralph |
| 7,129,840 B2 | 10/2006 | Hull et al. |
| 7,074,404 B2 | 11/2006 | Basey et al. |
| 7,279,287 B2 | 9/2007 | Ralph |
| 7,344,840 B2 | 3/2008 | Cohen et al. |
| 7,371,376 B1 | 5/2008 | Fendly |
| 7,371,379 B2 | 5/2008 | Baughman et al. |
| 7,435,797 B2 | 10/2008 | Lowman et al. |
| 7,449,184 B2 | 11/2008 | Allison et al. |
| 7,468,252 B2 | 12/2008 | Cohen et al. |
| 7,485,302 B2 | 3/2009 | Adams et al. |
| 7,485,704 B2 | 3/2009 | Fahrner et al. |
| 7,498,030 B2 | 3/2009 | Adams et al. |
| 7,537,931 B2 | 5/2009 | Adams et al. |
| 7,560,111 B2 | 7/2009 | Kao et al. |
| 7,575,748 B1 | 8/2009 | Erickson et al. |
| 7,501,122 B2 | 10/2009 | Adams et al. |
| 7,618,631 B2 | 11/2009 | Sliwkowski |
| 7,531,645 B2 | 12/2009 | Basey et al. |
| 7,682,609 B2 | 3/2010 | Andya et al. |
| 7,700,299 B2 | 4/2010 | Moecks et al. |
| 7,807,799 B2 | 5/2010 | Fahrner et al. |
| 7,846,441 B1 | 7/2010 | Hellmann |
| 7,674,589 B2 | 9/2010 | Cohen et al. |
| 7,811,773 B2 | 12/2010 | Ralph |
| 7,850,966 B2 | 12/2010 | Lowman et al. |
| 7,879,325 B2 | 1/2011 | Kao et al. |
| 7,892,549 B2 | 2/2011 | Paton et al. |
| 7,862,817 B2 | 4/2011 | Adams et al. |
| 7,993,834 B2 | 9/2011 | Mass |
| 8,044,017 B2 | 10/2011 | Emery et al. |
| 8,075,890 B2 | 12/2011 | Carter et al. |
| 8,075,892 B2 | 12/2011 | Hellmann |
| 8,163,287 B2 | 4/2012 | Sliwkowski et al. |
| 8,241,630 B2 | 8/2012 | Kao et al. |
| 8,247,397 B2 | 8/2012 | Belvin et al. |
| 8,309,087 B2 | 11/2012 | Hellmann |
| 8,337,856 B2 | 12/2012 | Blattler et al. |
| 8,404,234 B2 | 3/2013 | Allison et al. |
| 8,597,654 B2 | 3/2013 | Bryant |
| 8,425,908 B2 | 4/2013 | Hellmann |
| 8,440,402 B2 | 5/2013 | Mass |
| 8,529,901 B2 | 9/2013 | Hasmann et al. |
| 8,591,897 B2 | 11/2013 | Bryant |
| 8,372,396 B2 | 12/2013 | Andya et al. |
| 8,604,014 B2 | 12/2013 | Belvin et al. |
| 8,642,036 B2 | 2/2014 | Hellmann |
| 8,652,479 B2 | 2/2014 | Ebens, Jr. et al. |
| 8,663,643 B2 | 3/2014 | Berry et al. |
| 8,691,232 B2 | 4/2014 | Derynck et al. |
| 8,758,747 B2 | 6/2014 | Kallmeyer et al. |
| 8,840,896 B2 | 9/2014 | Lowman et al. |
| 9,017,671 B2 | 4/2015 | Andya et al. |
| 9,181,346 B2 | 10/2015 | Harris et al. |
| 9,345,661 B2 | 5/2016 | Adler et al. |
| 9,551,033 B2 | 1/2017 | Lee-Hoeflich et al. |
| 9,687,568 B2 | 6/2017 | Hasmann et al. |
| 9,815,904 B2 | 11/2017 | Gennaro et al. |
| 9,868,760 B2 | 1/2018 | Emery et al. |
| 9,968,676 B2 | 5/2018 | Adler et al. |
| 9,969,811 B2 | 5/2018 | Gennaro et al. |
| 10,160,811 B2 | 12/2018 | Baughman et al. |
| 10,280,228 B2 | 5/2019 | Baughman et al. |
| 10,385,405 B2 | 8/2019 | Lee-Hoeflich et al. |
| 10,689,457 B2 | 6/2020 | Paton et al. |
| 2001/0014326 A1 | 8/2001 | Andya et al. |
| 2002/0001587 A1 | 3/2002 | Erickson et al. |
| 2002/0035736 A1 | 3/2002 | Erickson et al. |
| 2002/0064785 A1 | 5/2002 | Mass |
| 2002/0090662 A1 | 11/2002 | Ralph |
| 2003/0078388 A1 | 4/2003 | Basey et al. |
| 2003/0134344 A1 | 7/2003 | Mass |
| 2003/0147884 A1 | 7/2003 | Paton et al. |
| 2003/0152987 A1 | 8/2003 | Cohen et al. |
| 2003/0162796 A1 | 8/2003 | Hilberg et al. |
| 2003/0202972 A1 | 10/2003 | Andya et al. |
| 2003/0170234 A1 | 11/2003 | Hellmann |
| 2004/0037823 A9 | 2/2004 | Paton et al. |
| 2004/0106161 A1 | 3/2004 | Bossenmaier et al. |
| 2004/0082047 A1 | 4/2004 | Emery et al. |
| 2004/0258685 A1 | 12/2004 | Brunetta et al. |
| 2005/0025753 A1 | 2/2005 | Han et al. |
| 2005/0063972 A1 | 3/2005 | Basey et al. |
| 2005/0244417 A1 | 3/2005 | Ashkenazi et al. |
| 2005/0244929 A1 | 3/2005 | Carter |
| 2005/0002928 A1 | 6/2005 | Hellmann |
| 2005/0208043 A1 | 9/2005 | Adams et al. |
| 2005/0238640 A1 | 10/2005 | Sliwkowski |
| 2005/0100944 A1 | 12/2005 | Cohen et al. |
| 2005/0276812 A1 | 12/2005 | Ebens et al. |
| 2006/0013819 A1 | 1/2006 | Kelsey |
| 2006/0018899 A1 | 1/2006 | Kao et al. |
| 2006/0034840 A1 | 2/2006 | Agus |
| 2006/0034842 A1 | 2/2006 | Adams et al. |
| 2006/0046270 A1 | 2/2006 | Ralph |
| 2006/0067930 A1 | 3/2006 | Adams et al. |
| 2006/0083739 A1 | 4/2006 | Sliwkowski |
| 2006/0088523 A1 | 4/2006 | Andya et al. |
| 2006/0073143 A1 | 6/2006 | Adams et al. |
| 2006/0165702 A1 | 7/2006 | Allison et al. |
| 2006/0198843 A1 | 7/2006 | Adams et al. |
| 2006/0275305 A1 | 7/2006 | Bryant |
| 2006/0121044 A1 | 8/2006 | Amler et al. |
| 2006/0182739 A1 | 8/2006 | Basey et al. |
| 2006/0183150 A1 | 8/2006 | Cohen et al. |
| 2006/0188509 A1 | 8/2006 | Derynck et al. |
| 2006/0193854 A1 | 8/2006 | Adams et al. |
| 2006/0204505 A1 | 9/2006 | Sliwkowski et al. |
| 2006/0210561 A1 | 9/2006 | Baughman et al. |
| 2006/0212956 A1 | 9/2006 | Crocker et al. |
| 2006/0099201 A1 | 11/2006 | Andya et al. |
| 2006/0228745 A1 | 12/2006 | Mass |
| 2007/0020261 A1 | 1/2007 | Sliwkowski et al. |
| 2007/0026001 A1 | 1/2007 | Ashkenazi et al. |
| 2007/0037228 A1 | 2/2007 | Moecks et al. |
| 2007/0166753 A1 | 7/2007 | Mass |
| 2007/0184055 A1 | 9/2007 | Sliwkowski |
| 2007/0224203 A1 | 9/2007 | Friess et al. |
| 2007/0009976 A1 | 11/2007 | Lenz et al. |
| 2007/0269429 A1 | 11/2007 | Kelsey et al. |
| 2007/0292419 A1 | 12/2007 | Hellmann |
| 2008/0102069 A1 | 1/2008 | Friess et al. |
| 2008/0038271 A1 | 2/2008 | Amler et al. |
| 2008/0050373 A1 | 2/2008 | Cohen |
| 2008/0050385 A1 | 2/2008 | Friess et al. |
| 2008/0050748 A1 | 2/2008 | Cohen et al. |
| 2008/0241146 A1 | 2/2008 | Ashkenazi et al. |
| 2008/0160026 A1 | 3/2008 | Ashkenazi et al. |
| 2008/0112958 A1 | 5/2008 | Mass |
| 2008/0171040 A1 | 7/2008 | Ebens et al. |
| 2008/0187533 A1 | 7/2008 | Hellmann |
| 2008/0108096 A1 | 8/2008 | Ralph |
| 2008/0226659 A1 | 9/2008 | Erickson et al. |
| 2008/0286280 A1 | 11/2008 | Kallmeyer et al. |
| 2008/0317753 A1 | 12/2008 | Amler et al. |
| 2009/0087432 A1 | 2/2009 | Sliwkowski |
| 2009/0081223 A1 | 3/2009 | Allison et al. |
| 2009/0220492 A1 | 3/2009 | Basey et al. |
| 2009/0098135 A1 | 4/2009 | Belvin et al. |
| 2009/0099344 A1 | 4/2009 | Fahrner et al. |
| 2009/0155259 A1 | 6/2009 | Derynck et al. |
| 2009/0155803 A1 | 6/2009 | Cohen et al. |
| 2009/0187007 A1 | 7/2009 | Lowman et al. |
| 2009/0202536 A1 | 8/2009 | Ebens et al. |
| 2009/0202546 A1 | 8/2009 | Harris et al. |
| 2009/0239236 A1 | 9/2009 | Mass |
| 2009/0226455 A1 | 10/2009 | Filvaroff |
| 2009/0148401 A1 | 11/2009 | Mrsny |

(56) References Cited

U.S. PATENT DOCUMENTS

| | | |
|---|---|---|
| 2009/0148435 A1 | 11/2009 | Lebreton et al. |
| 2009/0285837 A1 | 11/2009 | Kao et al. |
| 2009/0317387 A1 | 12/2009 | Paton et al. |
| 2010/0008975 A1 | 1/2010 | Amler et al. |
| 2010/0015157 A1 | 1/2010 | Andya et al. |
| 2010/0016556 A1 | 1/2010 | Carter et al. |
| 2010/0120053 A1 | 5/2010 | Cohen et al. |
| 2010/0196363 A1 | 5/2010 | Vanhauwere et al. |
| 2010/0112603 A1 | 6/2010 | Moecks et al. |
| 2010/0158899 A1 | 6/2010 | Andya et al. |
| 2010/0285010 A1 | 11/2010 | Friess et al. |
| 2010/0298156 A1 | 11/2010 | Lee-Hoeflich et al. |
| 2011/0044977 A1 | 2/2011 | Adler et al. |
| 2011/0129464 A1 | 2/2011 | Adams et al. |
| 2011/0027190 A1 | 3/2011 | Hasmann et al. |
| 2011/0064736 A1 | 3/2011 | Friess et al. |
| 2011/0064737 A1 | 3/2011 | Agus |
| 2011/0117096 A1 | 5/2011 | Bossenmaier et al. |
| 2011/0117097 A1 | 5/2011 | Kao et al. |
| 2011/0151454 A1 | 6/2011 | Lee-Hoeflich et al. |
| 2011/0159014 A1 | 6/2011 | Lowman et al. |
| 2011/0165157 A1 | 7/2011 | Derynck et al. |
| 2011/0223159 A1 | 9/2011 | Friess |
| 2011/0236383 A1 | 9/2011 | Andya et al. |
| 2011/0033460 A1 | 10/2011 | Fendly et al. |
| 2011/0250194 A1 | 10/2011 | Hellmann |
| 2012/0003217 A1 | 1/2012 | Bryant |
| 2012/0034213 A1 | 2/2012 | Hellmann |
| 2012/0034609 A1 | 2/2012 | Mass |
| 2012/0065381 A1 | 3/2012 | Emery et al. |
| 2012/0107391 A1 | 3/2012 | Kelsey |
| 2012/0093838 A1 | 4/2012 | Mass |
| 2012/0107302 A1 | 5/2012 | Berry et al. |
| 2012/0121586 A1 | 5/2012 | Kiermaier et al. |
| 2012/0251530 A1 | 10/2012 | Sliwkowski et al. |
| 2013/0195851 A1 | 1/2013 | Alavattam et al. |
| 2013/0039909 A1 | 2/2013 | Amler et al. |
| 2013/0071384 A1 | 3/2013 | Andya et al. |
| 2013/0095172 A1 | 4/2013 | Alavattam et al. |
| 2013/0108620 A1 | 5/2013 | Blattler et al. |
| 2013/0142865 A1 | 6/2013 | Allison et al. |
| 2013/0149299 A1 | 6/2013 | Baughman et al. |
| 2013/0183292 A1 | 7/2013 | Friess et al. |
| 2013/0195845 A1 | 8/2013 | Fendly et al. |
| 2013/0209459 A1 | 8/2013 | Hellmann |
| 2013/0224185 A1 | 8/2013 | Andya et al. |
| 2013/0323180 A1 | 12/2013 | Hasmann et al. |
| 2013/0345217 A1 | 12/2013 | Belvin et al. |
| 2014/0018523 A1 | 1/2014 | Basey et al. |
| 2014/0044704 A1 | 2/2014 | Paton et al. |
| 2014/0044706 A1 | 2/2014 | Belvin et al. |
| 2014/0044709 A1 | 2/2014 | Klencke et al. |
| 2014/0079692 A1 | 3/2014 | Baughman et al. |
| 2014/0086940 A1 | 3/2014 | Bryant |
| 2014/0093458 A1 | 4/2014 | Dobosz et al. |
| 2014/0140993 A1 | 5/2014 | Ross et al. |
| 2014/0186343 A1 | 7/2014 | Harris et al. |
| 2014/0186867 A1 | 7/2014 | Harris et al. |
| 2014/0212411 A1 | 7/2014 | Blattler et al. |
| 2014/0227255 A1 | 8/2014 | Bauss et al. |
| 2014/0248274 A1 | 9/2014 | Kallmeyer et al. |
| 2014/0248609 A1 | 9/2014 | Mass |
| 2014/0308277 A1 | 10/2014 | Gennaro et al. |
| 2014/0322202 A1 | 10/2014 | Cohen |
| 2014/0341886 A1 | 11/2014 | Hellmann |
| 2016/0175438 A1 | 6/2016 | Alavattam et al. |
| 2016/0376377 A1 | 12/2016 | Basey et al. |
| 2017/0008971 A1 | 1/2017 | Dennis et al. |
| 2017/0029527 A1 | 2/2017 | Paton et al. |
| 2017/0035907 A1 | 2/2017 | Green et al. |
| 2017/0037147 A1 | 2/2017 | Allison et al. |
| 2017/0073777 A1 | 3/2017 | Lee-Hoeflich et al. |
| 2017/0166656 A1 | 6/2017 | Lowman et al. |
| 2017/0174785 A1 | 6/2017 | Harris et al. |
| 2017/0190786 A1 | 7/2017 | Fendly et al. |
| 2018/0037622 A1 | 2/2018 | Gennaro et al. |
| 2018/0037660 A1 | 2/2018 | Gennaro et al. |
| 2018/0037661 A1 | 2/2018 | Gennaro et al. |
| 2020/0157238 A1 | 5/2020 | Gennaro et al. |
| 2020/0172631 A1 | 6/2020 | Seshagiri et al. |
| 2020/0179515 A1 | 6/2020 | Andya et al. |
| 2020/0206348 A1 | 7/2020 | Benyunes et al. |
| 2020/0237910 A1 | 7/2020 | Beattie et al. |
| 2020/0239595 A1 | 7/2020 | Allison et al. |

FOREIGN PATENT DOCUMENTS

| | | |
|---|---|---|
| WO | 01/89566 A1 | 11/2001 |
| WO | 2004/078140 A2 | 9/2004 |
| WO | 2006/044908 A2 | 4/2006 |
| WO | 2006/091871 A1 | 8/2006 |

OTHER PUBLICATIONS

Hoffmann-La Roche, "A Study of Pertuzumab and Trastuzumab Subcutaneous (SC) Treatment in Combination With a Taxane in Participants With Human Epidermal Growth Factor Receptor 2 (HER2)-Positive Metastatic Breast Cancer (SAPPHIRE)", (ClinicalTrials.gov Identifier NCT02019277; Study ID ML28784; First Posted Dec. 24, 2013; Last Update Received Sep. 13, 2018; Retrieved Feb. 7, 2020); 1-11 (Feb. 7, 2020) https://clinicaltrials.gov/ct2/show/NCT02019277.

Hoffmann-La Roche, "A Study to Evaluate the Pharmacokinetics, Efficacy, and Safety of Subcutaneous Administration of the Fixed-Dose Combination of Pertuzumab and Trastuzumab in Combination With Chemotherapy in Participants With HER2-Positive Early Breast Cancer (FeDeriCa)" (ClinicalTrials.gov Identifier: NCT03493854; Study ID: WO40324; First Posted Apr. 11, 2018; Last Update Posted Jan. 3, 2020; Retrieved Feb. 7, 2020; 1-13 (Feb. 7, 2020) https://clinicaltrials.gov/ct2/show/NCT03493854.

Hoffmann-La Roche, A Dose-Finding Study of Pertuzumab (Perjeta) in Combination With Trastuzumab (Herceptin) in Healthy Male Participants and Women With Early Breast Cancer (EBC)' (ClinicalTrials.gov Identifier NCT02738970; Study ID: BO30185; First Posted Apr. 14, 2016; Last Updated Posted Jun. 12, 2018; Retrieved Feb. 7, 2020), 1-10 (Feb. 7, 2020) https://clinicaltrials.gov/ct2/show/NCT02738970.

Hoffmann-La Roche, "A Study to Evaluate Patient Preference and Satisfaction of Subcutaneous Administration of the Fixed-Dose Combination of Pertuzumab and Trastuzumab in Participants With HER2-Positive Early Breast Cancer (PHranceSCa)" (ClinicalTrials.gov Identifier: NCT03674112; Study ID: RO7198574; First Posted Sep. 17, 2018; Last Update Posted: Aug. 12, 2019; Retrieved: Aug. 15, 2019; 1-12 (Aug. 15, 2019) https://clinicaltrials.gov/ct2/show/NCT03674112.

Hoffmann-La Roche, "A Two-Arm Study to Evaluate the Pharmacokinetics, Efficacy, and Safety of Subcutaneous Administration of the Fixed-Dose Combination of Pertuzumab and Trastuzumab in Combination With Chemotherapy in Chinese Participants With HER2-Positive Early Breast Cancer ", (ClinicalTrials.gov Identifier NCT04024462; Study ID YO41137; First Posted Jul. 18, 2019; Last Update Posted Feb. 5, 2020; Retrieved Feb. 7, 2020) ; 1-13 (Feb. 7, 2020) https://clinicaltrials.gov/ct2/show/NCT04024462.

Khan, Tarik, "CMC Challenges in Developing Co-Formulations and Co-Administration Procedures with Multiple mAbs" AAPS National Biotechnology Conference, pp. 1-21 ( May 2, 2017).

Roche's fixed-dose subcutaneous combination of Perjeta and Herceptin showed non-inferiority when compared to intravenous formulations for people with HER2-positive breast cancer, Press Release, pp. 1-3 https://www.roche.com/media/releases/med-cor-2019-09-13.htm ( Sep. 13, 2019).

Agus et al., "Clinical Activity in a Phase I Trial of HER-2-Targeted rhuMAb 2C4 (pertuzumab) in Patients with Advanced Solid Malignancies (AST)" Proceedings of the American Society of Clinical Oncology (Abstract No. 771), 22:192 ( 2003).

(56) References Cited

OTHER PUBLICATIONS

Agus et al., "Targeting ligand-activated ErbB2 signaling inhibits breast and prostate tumor growth" Cancer Cell 2(2):127-137 (Aug. 2002).
Allison et al., "Pharmacokinetics of HER2-targeted rhuMAb 2C4 (pertuzumab) in patients with advanced solid malignancies: Phase Ia results" Pro Am Soc Clin Oncol 22:197 ( 2003).
Arming, S. et al., "In vitro Mutagenesis of PH-20 Hyaluronidase from Human Sperm" Eur J Biochem 247:810-814 ( 1997).
Baselga et al., "Objective response rate in a phase II multicenter trial of pertuzumab (P), a HER2 dimerization inhibiting monaclonal antibody, in combination with trastuzumab (T) in patients (pts) with HER2-positive metastatic breast cancer (MBC) which has progressed during treatment with T" J Clin Oncol (Abstract 1004; 2007 ASCO Annual Meeting), 25(18S Suppl Jun. 20):1-2 ( 2007).
Baselga et al., "Pertuzumab plus trastuzumab plus docetaxel for metastatic breast cancer" N Engl J Med 366(2):109-119 (Jan. 12, 2012).
Baselga et al., "Phase II Study of Weekly Intravenous Recombinant Humanized Anti-p185 $^{HER2}$ Monoclonal Antibody in Patients With HER2/neu-Overexpressing Metastatic Breast Cancer" J Clin Oncol 14(3):737-744 (Mar. 1996).
Bookbinder et al., "A recombinant human enzyme for enhanced interstitial transport of therapeutics" J Control Release 114(2):230-41 (Aug. 2006).
Bywaters, E. G. L. et al., "Reconstitution of the Dermal Barrier to Dye Spread After Hyaluronidase Injection" Brit Med J 2(4741):1178-1183 (Nov. 1951).
Chain, E., "A Mucolytic Enzyme in Testes Extracts" Nature 144:977-978 ( 1939).
Cherr, G. N. et al., "The PH-20 Protein in Cynomolgus Macaque Spermatozoa: Identification of Two Different Forms Exhibiting Hyaluronidase Activity" Dev Biol 175:142-153 ( 1996).
Cherry et al., "Physical Mechanisms of Cell Damage in Microcarrier Cell Culture Bioreactors" Biotechnology and Bioengineering 32:1001-1014 ( 1988).
Cho et al., "Structure of the extracellular region of HER2 alone and in complex with the Herceptin Fab" Nature 421:756-760 (Feb. 13, 2003).
Danilkovitch-Miagkova, A. et al., "Hyaluronidase 2 Negatively Regulates RON Receptor Tyrosine Kinase and Mediates Transformation of Epithelial Cells by Jaagsiekte Sheep Retrovirus" P Natl Acad Sci USA 100(8):4580-4585 (Apr. 15, 2003).
Duran-Reynals, "A spreading factor in certain snake venoms and its relation to their mode of action" Cr Soc Biol Paris:69-81 ( 1938).
Frost, G. I. et al., "A microtiter-based assay for hyaluronidase activity not requiring specialized reagents" Anal Biochem 251(2):263-9 (Sep. 1997).
Frost, G. I. et al., "Purification, Cloning, and Expression of Human Plasma Hyaluronidase" Biochem Bioph Res Co 236:10-15 ( 1997).
Frost, Gregory I., "Recombinant Human Hyaluronidase (rHuPH20): an Enabling Platform for Subcutaneous Drug and Fluid Administration" Expert Opin Drug Del 4(4):427-440 ( 2007).
Gianni et al., "5-year analysis of neoadjuvant pertuzumab and trastuzumab in patients with locally advanced, inflammatory, or early-stage HER2-positive breast cancer (NeoSphere): a multicentre, open-label, phase 2 randomised trial" Lancet Oncol. 17(6):791-800 (Jun. 2016).
Gianni et al., "Efficacy and safety of neoadjuvant pertuzumab and trastuzumab in women with locally advanced, inflammatory, or early HER2-positive breast cancer (NeoSphere): a randomised multicentre, open-label, phase 2 trial" Lancet Oncol 13:25-32 (Jan. 2012).
Hamizi et al., "Subcutaneous trastuzumab: development of a new formulation for treatment of HER2-positive early breast cancer" Onco Targets Ther. 6:89-94 ( 2013).
Harari and Yarden, "Molecular mechanisms underlying ErbB2/HER2 action in breast cancer" Oncogene 19(53):6102-14 (Dec. 2000).
Harris et al. et al., "Endocytic Function, Glycosaminoglycan Specificity, and Antibody Sensitivity of the Recombinant Human 190-kDa Hyaluronan Receptor for Endocytosis (HARE)" J Biol Chem 279(35):36201-36209 ( 2004).
Hoffmann-La Roche:"A Dose-Finding Study of Pertuzumab (Perjeta) in Combination With Trastuzumab (Herceptin) in Healthy Male Participants and Women With Early Breast Cancer (EBC)", ClinicalTrials.gov Identifier: NCT02738970, Apr. 14, 2016, Reterieved from the Internet:https://clinicaltrials.gov/ct2/show/nct02738970.
Lalancette, C. et al., "Characterization of an 80-Kilodalton Bull Sperm Protein Identified as PH-20" Biology of Reproduction 65:628-636 ( 2001).
Laurent et al. Degradation of Bioactive Substances: Physiology and Pathophysiology J.H. Henriksen, Boca Raton, FL:CRC Press,:249-265 ( 1991).
Laurent, U. B. G. et al., "Catabolism of Hyaluronan in Rabbit Skin Takes Place Locally, In Lymph Nodes and Liver" Exp Physiol 76:695-703 ( 1991).
Malik et al., 'Dose-Response Studies of Recombinant Humanized Monoclonal Antibody 2C4 in Tumor Xenograft Models' Proceedings of the AACR (Abstract No. 773) 44:176-177 (Mar. 2003) (For information purposes only).
Marty et al., "Randomized Phase II Trial of the Efficacy and Saftey of Trastuzumab Combined with Docetaxel in Patients with Human Epidermal Growth Factor Receptor 2-Positive Metastatic Breast Cancer Administered as First-Line Treatment" J Clin Oncol 23(19):4265-4274 (Jul. 1, 2005).
PCT—"Annex Form PCT/ISA/206 Communication Relating to the Results of the Partial International Search, dated Jun. 18, 2018—International Application No. PCT/US2018/013854".
Phelps, B. M. et al., "Restricted Lateral Diffusion of PH-20, a PI-Anchored Sperm Membrane Protein" Science 240:1780-1782 (Jun. 1988).
Portera et al., "A report of cardiac events in a phase II clinical study using trastuzumab combined with pertuzumab in HER2-positive metastatic breast cancer (MBC)" J Clin Oncol (Abstract No. 1028 (2007 ASCO Annual Meeting)), 25(18S Suppl Jun. 20):1028 (Jun. 2007).
Slamon et al., "Use of chemotherapy plus a monoclonal antibody against HER2 for metastatic breast cancer that overexpresses HER2" N Engl J Med. 344(11):783-92 (Mar. 2001).
Sliwkowski, "Ready to partner" Nat Struct Biol. 10(3):158-9 (Mar. 2003).
Tammi et al., "Degradation of Newly Synthesized High Molecular Mass Hyaluronan in the Epidermal and Dermal Compartments of Human Skin in Organ Culture" J Invest Dermatol 97:126-130 ( 1991).
Weissmann, Bernard, "The Transglycosylative Action of Testicular Hyaluronidase" J Biol Chem 216:783-794 ( 1955).
Yarden et al., "Untangling the ErbB signalling network" Nat Rev Mol Cell Biol 2:127-137 (Feb. 2001).
Celltrion Press Release, "Remsima SC joins the existing market for subcutaneous injections . . . signaling a drastic change in autoimmune treatments" MoneyToday-Korea (Interview, CEO—SEO, Jung-Jin; Korean with Eng. Transl.; Web page Access Date: Aug. 6, 2020),:1-5 (Nov 26, 2019) https://news.mt.co.kr/mtview.php?no=2019112610162881129.
McKee, S., "Teva's subcutaneous asthma drug fails in PhIII" Pharma Times Media, Ltd:1 (Jan. 28, 2018) http://www.pharmatimes.com/news/tevas_subcutaneous_asthma_drug_fails_in_phiii_1218310.
Pimentel, F.F., et al., "Development of New Formulations of Biologics: Expectations, Immunogenicity, and Safety for Subcutaneous Trastuzumab" Pharmaceut Med 32(5):319-523 (Sep. 24, 2018).
"Pertuzumab (Perjeta) United States Prescribing Information (USPI),":1-35 (Dec. 2017)—Pertuzumab (Perjeta) United States Prescribing Information (USPI).
"Pertuzumab, Trastuzumab, and Hyaluronidase-zzxf (Phesgo) United States Prescribing Information (USPI),":1-23 (Jun. 2020)—'Pertuzumab, Trastuzumab, and Hyaluronidase-zzx (Phesgo) United States Prescribing Information (USPI)—.

(56) References Cited

OTHER PUBLICATIONS

"Trastuzumab (Herceptin) United States Prescribing Information (USPI),":1-38 (Apr. 2017)—Trastuzumab (Herceptin) United States Prescribing Information (USPI)—.

* cited by examiner

Variable Light

```
                 10                  20                  30              40
2C4     DTVMTQSHKIMSTSVGDRVSITC  [KASQDVSIGVA]  WYQQRP
        **    **** *             *                     *
574     DIQMTQSPSSLSASVGDRVTITC  [KASQDVSIGVA]  WYQQKP
                                    *   * hum κI  DIQMTQSPSSLSASVGDRVTITC  [RASQSISNYLA]  WYQQKP 50           60         0              80
2C4     GQSPKLLIY  [SASYRYT]  GVPDRFTGSGSGTDFTFTISSVQA
        **                       *  *         *     * *
574     GKAPKLLIY  [SASYRYT]  GVPSRFSGSGSGTDFTLTISSLQP
                    * ***** hum κI  GKAPKLLIY  [AASSLES]  GVPSRFSGSGSGTDFTLTISSLQP 90          100
2C4     EDLAVYYC  [QQYYIYPYT]  FGGGTKLEIK     (SEQ ID NO:5)
         * *                     *   *
574     EDFATYYC  [QQYYIYPYT]  FGQGTKVEIK     (SEQ ID NO:7)
                    *** * hum κI  EDFATYYC  [QQYNSLPWT]  FGQGTKVEIK     (SEQ ID NO:9)
```

*FIG. 2A*

Variable Heavy

```
                 10                  20                   30               40
2C4      EVQLQQSGPELVKPGTSVKISCKAS  [GFTFTDYTMD]  WVKQS
           **  **  *   *  ***   *                        * *
574      EVQLVESGGGLVQPGGSLRLSCAAS  [GFTFTDYTMD]  WVRQA
                                       ** * * hum III  EVQLVESGGGLVQPGGSLRLSCAAS  [GFTFSSYAMS]  WVRQA 50       a      60                  70          80
2C4      HGKSLEWIG  [DVNPNSGGSIYNQRFKG]  KASLTVDRSSRIVYM
         *  *   **                        *** *      **** *
574      PGKGLEWVA  [DVNPNSGGSIYNQRFKG]  RFTLSVDRSKNTLYL
                     **** * ****       *  * hum III  PGKGLEWVA  [VISGDGGSTYYADSVKG]  RFTISRDNSKNTLYL abc      90       100ab             110
2C4      ELRSLTFEDTAVYYCAR  [NLGPSFYFDY]  WGQGTTLTVSS     (SEQ ID NO:6)
         *** **                                   **
574      QMNSLRAEDTAVYYCAR  [NLGPSFYFDY]  WGQGTLVTVSS     (SEQ ID NO:8)
                              ******** hum III  QMNSLRAEDTAVYYCAR  [GRVGYSLYDY]  WGQGTLVTVSS     (SEQ ID NO:10)
```

*FIG. 2B*

Amino Acid Sequence for Pertuzumab Light Chain

```
1          10         20         30         40         50         60
|          |          |          |          |          |          |
DIQMTQSPSSLSASVGDRVTITCKASQDVSIGVAWYQQKPGKAPKLLIYSASYRYTGVPS 70         80         90        100        110        120
           |          |          |          |          |          |
RFSGSGSGTDFTLTISSLQPEDFATYYCQQYYIYPYTFGQGTKVEIKRTVAAPSVFIFPP 130        140        150        160        170        180
           |          |          |          |          |          |
SDEQLKSGTASVVCLLNNFYPREAKVQWKVDNALQSGNSQESVTEQDSKDSTYSLSSTLT 190        200        210
           |          |          |
LSKADYEKHKVYACEVTHQGLSSPVTKSFNRGEC  (SEQ ID NO: 11)
```

FIG. 3A

Amino Acid Sequence for Pertuzumab Heavy Chain

```
1          10         20         30         40         50         60
|          |          |          |          |          |          |
EVQLVESGGGLVQPGGSLRLSCAASGFTFTDYTMDWVRQAPGKGLEWVADVNPNSGGSIY 70         80         90        100        110        120
           |          |          |          |          |          |
NQRFKGRFTLSVDRSKNTLYLQMNSLRAEDTAVYYCARNLGPSFYFDYWGQGTLVTVSSA 130        140        150        160        170        180
           |          |          |          |          |          |
STKGPSVFPLAPSSKSTSGGTAALGCLVKDYFPEPVTVSWNSGALTSGVHTFPAVLQSSG 190        200        210        220        230        240
           |          |          |          |          |          |
LYSLSSVVTVPSSSLGTQTYICNVNHKPSNTKVDKKVEPKSCDKTHTCPPCPAPELLGGP 250        260        270        280        290        300
           |          |          |          |          |          *|
SVFLFPPKPKDTLMISRTPEVTCVVVDVSHEDPEVKFNWYVDGVEVHNAKTKPREEQYNS 310        320        330        340        350        360
           |          |          |          |          |          |
TYRVVSVLTVLHQDWLNGKEYKCKVSNKALPAPIEKTISKAKGQPREPQVYTLPPSREEM 370        380        390        400        410        420
           |          |          |          |          |          |
TKNQVSLTCLVKGFYPSDIAVEWESNGQPENNYKTTPPVLDSDGSFFLYSKLTVDKSRWQ 430        440        448
           |          |          |
QGNVFSCSVMHEALHNHYTQKSLSLSPG   (SEQ ID NO: 12)
```

FIG. 3B

Trastuzumab Light Chain

```
  1                                            15                            30                           45
  D I Q M T Q S P S S L S A S V G D R V T I T C R A S Q D V N T A V A W Y Q Q K P G K A P K
 46                                            60                            75                           90
  L L I Y S A S F L Y S G V P S R F S G S R S G T D F T L T I S S L Q P E D F A T Y Y C Q
 91                                           105                           120                          135
  H Y T T P P T F G Q G T K V E I K R T V A A P S V F I F P P S D E Q L K S G T A S V V C L
136                                           150                           165                          180
  L N N F Y P R E A K V Q W K V D N A L Q S G N S Q E S V T E Q D S K D S T Y S L S S T L T
181                                           195                           210  214
  L S K A D Y E K H K V Y A C E V T H Q G L S S P V T K S F N R G E C   (SEQ ID NO: 13)
```

FIG. 4A

Trastuzumab Heavy Chain

```
1   EVQLVESGGG LVQPGGSLRL SCAASGFNIK DTYIHWVRQA PGKGL          45
46  EWVARIYPTN GYTRYADSVK GRFTISADTS KNTAYLQMNS LRAED          90
91  TAVYYCSRWG GDGFYAMDYW GQGTLVTVSS ASTKGPSVFP LAPSS          135
136 KSTSGGTAAL GCLVKDYFPE PVTVSWNSGA LTSGVHTFPA VLQSS          180
181 GLYSLSSVVT VPSSSLGTQT YICNVNHKPS NTKVDKKVEP KSCDK          225
226 THTCPPCPAP ELLGGPSVFL FPPKPKDTLM ISRTPEVTCV VVDVS          270
271 HEDPEVKFNW YVDGVEVHNA KTKPREEQYN STYRVVSVLT VLHQD          315
316 WLNGKEYKCK VSNKALPAPI EKTISKAKGQ PREPQVYTLP PSREE          360
361 MTKNQVSLTC LVKGFYPSDI AVEWESNGQP ENNYKTTPPV LDSDG          405
406 SFFLYSKLTV DKSRWQQGNV FSCSVMHEAL HNHYTQKSLS LSPG           449
```

(SEQ ID NO: 14)

FIG. 4B

Pertuzumab Variant Light Chain

```
1                                              15                            30                              45
V H S D I Q M T Q S P S S L S A S V G D R V T I T C K A S Q D V S I G V A W Y Q Q K P G K
46                                             60                            75                              90
A P K L L I Y S A S Y R Y T G V P S R F S G S G S G T D F T L T I S S L Q P E D F A T Y Y
91                                             105                           120                             135
C Q Q Y Y I Y P Y T F G Q G T K V E I K R T V A A P S V F I F P P S D E Q L K S G T A S V
136                                            150                           165                             180
V C L L N N F Y P R E A K V Q W K V D N A L Q S G N S Q E S V T E Q D S K D S T Y S L S S
181                                            195                           210         217
T L T L S K A D Y E K H K V Y A C E V T H Q G L S S P V T K S F N R G E C     (SEQ ID NO: 15)
```

FIG. 5A

Pertuzumab Variant Heavy Chain

```
  1 E V Q L V E S G G G L V Q P G G S L R L S C A A S G F T F T D Y T M D W V R Q A P G K G L    45
 46 E W V A D V N P N S G G S I Y N Q R F K G R F T L S V D R S K N T L Y L Q M N S L R A E D    90
 91 T A V Y Y C A R N L G P S F Y F D Y W G Q G T L V T V S S A S T K G P S V F P L A P S S K   135
136 S T S G G T A A L G C L V K D Y F P E P V T V S W N S G A L T S G V H T F P A V L Q S S G   180
181 L Y S L S S V V T V P S S S L G T Q T Y I C N V N H K P S N T K V D K K V E P K S C D K T   225
226 H T C P P C P A P E L L G G P S V F L F P P K P K D T L M I S R T P E V T C V V V D V S H   270
271 E D P E V K F N W Y V D G V E V H N A K T K P R E E Q Y N S T Y R V V S V L T V L H Q D W   315
316 L N G K E Y K C K V S N K A L P A P I E K T I S K A K G Q P R E P Q V Y T L P P S R E E M   360
361 T K N Q V S L T C L V K G F Y P S D I A V E W E S N G Q P E N N Y K T T P P V L D S D G S   405
406 F F L Y S K L T V D K S R W Q Q G N V F S C S V M H E A L H N H Y T Q K S L S L S P G K   449
```

(SEQ ID NO: 16)

FIG. 5B

8030185 Study Overview

| Cohort | Population | N | Agent | Dose (mg) Single Injection | Volume of Injection (mL) | Concentration of Halozyme (U/mL)# | Amount of Halozyme (Units) |
|---|---|---|---|---|---|---|---|
| Part 1 | | | | Dose Finding | | | |
| 1 (control) | HMV | 6 | Piv | 420 | | NA | NA |
| 2 | HMV | 6 | Psc | 400 | 3.3 | 2,000 U/mL | 6,600 U |
| 3 | HMV | 6 | Psc | 600 | 5 | 2,000 U/mL | 10,000 U |
| 4 | HMV | 6 | Psc loading | 1200 | 10 | 2,000 U/mL | 20,000 U |
| 5 (control) | HMV | 6 | Hsc | 600 | 5 | 2,000 U/mL | 10,000 U |
| 6 | HMV | 6 | Psc + Hsc (co-mix) | 400 + 600 | 8.3 | 2,000 U/mL | 16,600 U |
| 7 | HMV | 6 | Psc + Hsc (co-mix) | 1200 + 600 | 15 | 2,000 U/mL | 30,000 U |
| 8 (Halozyme from Herceptin only) | HMV | 6 | Psc + Hsc (co-mix) | 1200 + 600 | 15 | 667 U/mL | 10,000 U |
| Part 2 | | | | Dose Confirmation | | | |
| 9* | EBC | 20 | Psc + Hsc (co-mix) | TBD + 600 | | | |
| 10^ | EBC | 20 | Psc + Hsc (FDC) | TBD + 600 | | | |

MabThera and Herceptin SC use 2,000 U/mL
*Enrollment planned January 2017
^Enrollment planned October 2017

FIG. 8

Overview of Adverse Events in Part 1

| Extreme Grade | Cohort 1 (P IV 420mg) N = 6 | Cohort 5 (H 600mg) N = 6 | Cohort 2 (P 400mg) N = 6 | Cohort 3 (P 600mg) N = 6 | Cohort 4 (P 1200 mg) N = 6 | Cohort 6 (P 400mg+ H 600mg) N = 6 | Cohort 7 (P 1200mg+ H 600mg) N = 6 | Cohort 8 (P 1200mg* + H 600mg) N = 6 |
|---|---|---|---|---|---|---|---|---|
| Total AEs n = 145 (%) | 15 (10) | 10 (7) | 10 (7) | 22 (15) | 24 (17) | 33 (23) | 18 (13) | 13 (9) |
| Grade 1 | 9 (6) | 9 (6) | 6 (4) | 19 (13) | 17 (12) | 21 (15) | 9 (6) | 8 (6) |
| Grade 2 | 2 (1) | 1 (1) | 4 (3) | 1 (1) | 2 (1) | 6 (4) | 4 (3) | 2 (1) |
| Grade >=3 | 1 (1) | 0 (0) | 0 (0) | 0 (0) | 0 (0) | 0 (0) | 0 (0) | 0 (0) | o One Grade 3 AE of diarrhoea, onset Day 32: unrelated, concurrent illness.
  - Possible viral infection as concurrent URTI o No SAE, AESI, AE leading to discontinuation, AE leading to death o Some AEs ongoing so no final Extreme Grade

*No additional rHuPH20

FIG. 13

Overview of Adverse Events in Part 1
No. of subjects

| No. of subjects with AE | Cohort 1 (P IV 420mg) N = 6 | Cohort 5 (H 600mg) N = 6 | Cohort 2 (P400mg) N = 6 | Cohort 3 (P 600mg) N = 6 | Cohort 4 (P 1200 mg) N = 6 | Cohort 6 (P 400 mg + H 600mg) N = 6 | Cohort 7 (P 1200 mg + H 600mg) N = 6 | Cohort 8 (P 1200 mg*+ H 600mg) N = 6 |
|---|---|---|---|---|---|---|---|---|
| Any AE, n (%) | 5 (83) | 5 (83) | 5 (83) | 6 (100) | 5 (83) | 6 (100) | 6 (100) | 6 (100) |
| Grade 1 | 4 (67) | 5 (83) | 4 (67) | 6 (100) | 5 (83) | 6 (100) | 6 (100) | 5 (83) |
| Grade 2 | 2 (33) | 1 (17) | 3 (50) | 1 (17) | 2 (33) | 5 (83) | 2 (33) | 2 (33) |
| Grade >= 3 | 1 (17) | 0 | 0 | 0 | 0 | 0 | 0 | 0 |

*No additional rHuPH20

FIG. 14

Most Common Adverse Events (all grades) – incidence ≥ 5% overall in study No. of subjects

| Adverse event preferred term | Cohort 1 (P IV 420mg) N=6 | Cohort 5 (H 600mg) N=6 | Cohort 2 (P 400mg) N=6 | Cohort 3 (P 600mg) N=6 | Cohort 4 (P 1200mg) N=6 | Cohort 6 (P 400 mg + H 600mg) N=6 | Cohort 7 (P 1200 mg + H 600mg) N=6 | Cohort 8 (P 1200 mg + H 600mg) N=6 |
|---|---|---|---|---|---|---|---|---|
| UPPER RESPIRATORY TRACT INFECTION | 2 (33) | 0 | 0 | 2 (33) | 2 (33) | 3 (50) | 2 (33) | 2 (33) |
| DIARRHOEA | 3 (50) | 0 | 1 (17) | 2 (33) | 1 (17) | 1 (17) | 1 (17) | 0 |
| HEADACHE | 1 (17) | 1 (17) | 0 | 1 (17) | 2 (33) | 0 | 4 (67) | 0 |
| DRUG ERUPTION | 1 (17) | 0 | 0 | 0 | 1 (17) | 2 (33) | 3 (50) | 2 (33) |
| ANGULAR CHEILITIS | 2 (33) | 0 | 0 | 1 (17) | 0 | 3 (50) | 0 | 1 (17) |
| PAIN IN EXTREMITY | 0 | 2 (33) | 0 | 1 (17) | 2 (33) | 1 (17) | 0 | 0 |
| EPISTAXIS | 1 (17) | 0 | 0 | 0 | 1 (17) | 3 (50) | 0 | 0 |
| RASH | 0 | 1 (17) | 1 (17) | 2 (33) | 1 (17) | 0 | 0 | 0 |
| ABDOMINAL PAIN | 0 | 0 | 2 (33) | 0 | 0 | 1 (17) | 1 (17) | 0 |
| DRY SKIN | 0 | 0 | 0 | 0 | 0 | 2 (33) | 0 | 0 |
| INJECTION RELATED REACTION | 0 | 1 (17) | 1 (17) | 1 (17) | 0 | 0 | 0 | 1 (17) |
| NASAL CONGESTION | 0 | 1 (17) | 0 | 0 | 2 (33) | 0 | 0 | 1 (17) |
| OROPHARYNGEAL PAIN | 1 (17) | 0 | 0 | 0 | 1 (17) | 0 | 0 | 1 (17) |
| ECZEMA | 0 | 1 (17) | 0 | 0 | 1 (17) | 1 (17) | 0 | 0 |
| FOLLICULITIS | 0 | 0 | 0 | 1 (17) | 1 (17) | 0 | 0 | 0 |

FIG. 15

EGFR Related Toxicity

| AEGT basket term/ No. of subjects (%) | Cohort 1 (P IV 420mg) N = 6 | Cohort 5 (H 600mg) N = 6 | Cohort 2 (P 400mg) N = 6 | Cohort 3 (P 600mg) N = 6 | Cohort 4 (P 1200mg) N = 6 | Cohort 6 (P 400 mg+ H 600mg) N = 6 | Cohort 7 (P 1200 mg+ H 600mg) N = 6 | Cohort 8 (P 1200 mg*+ H 600mg) N = 6 |
|---|---|---|---|---|---|---|---|---|
| Diarrhoea | 3 (50) | 0 | 1 (17) | 2 (33) | 2 (33) | 2 (33) | 1 (17) | 0 |
| Mucositis | 2 (33) | 0 | 2 (33) | 1 (17) | 0 | 4 (67) | 0 | 1 (17) |
| EGFR Rash | 1 (17) | 2 (33) | 1 (17) | 3 (50) | 3 (50) | 3 (50) | 4 (67) | 2 (33) |

Diarrhoea [PT: Diarrhoea (9), Frequent Bowel Movements (2)]
Onset range: Day 2- 36 with most in first 10 days after drug Mucositis [PT: Angular Cheilitis (7), Mouth Ulceration (2), Aphthous Ulcer (2) and Gastroenteritis (1)]
Onset range: Day 8- 38, majority occurring between 13 - 29

EGFR Associated Rash [PT: Drug Eruption (9), Rash (5), Eczema (3), Folliculitis (2), Acne (1) and Dermatitis Acneform (1)]
Onset range: Day 4 - 54, no pattern

*No additional rHuPH20

FIG. 16

Injection Related Reactions and Injection Site Reactions

| No. of subjects (%) | Cohort 1 (P IV 420mg) N=6 | Cohort 2 (P 400mg) N=6 | Cohort 3 (P 600mg) N=6 | Cohort 4 (P 1200mg) N=6 | Cohort 5 (H 600mg) N=6 | Cohort 6 (P 400mg+ H 600mg) N=6 | Cohort 7 (P 1200mg+ H 600mg) N=6 | Cohort 8 (P 1200mg*+ H 600mg) N=6 |
|---|---|---|---|---|---|---|---|---|
| Infusion Related Reaction (Systemic) | 0 | | | | | | | |
| Injection Related Reaction (Systemic) | | 0 | 0 | 0 | 1 (17) | 2 (33) | 0 | 1 (17) |
| Injection Site Reaction (Local) | | 0 | 0 | 0 | 0 | 0 | 1 (17) | 0 |

Injection Site Reaction (Local): any morphological or physiological change at or near the injection site
- 1 Injection Site Reaction in Cohort 7
- 1200mg P SC + 600mg H SC with rHuPH20
- Symptoms were discomfort, pain, tightness and numbness at injection site Injection Related Reactions (Systemic)
- Symptoms included fever, chills, nausea, stiffness, lightheadedness, skin sensitivity, photophobia, temperature fluctuation, headache

*No additional rHuPH20

FIG. 17

LVEF – ECHO Assessments

| No. of subjects (%) | Cohort 1 (P IV) N=6 | Cohort 5 (H SC) N=6 | Cohort 2, 3, 4 (P SC) N=18 | Cohort 6, 7, 8 (P+H SC) N=18 |
|---|---|---|---|---|
| LVEF measurement (%) - Baseline | 6 (100) | 6 (100) | 18 (100) | 18 (100) |
| Absolute value <50% and decrease from baseline ≥10% | 0 | 0 | 0 | 0 |
| Absolute value <50% OR decrease from baseline ≥10%points | 0 | 0 | 1* | 0 |

\* Cohort 3 (600mg P SC):
- One HMV had a drop of >10% from 67% at Baseline to 56% at Day 22
- Follow up EF at Day 85 = 60 %
- Cardiologist confirmed no evidence of cardiotoxicity
- Drop due to variability of imaging method

Drug Substance to support FDCs

Trastuzumab (Herceptin SC DS)
- Trastuzumab: 120 mg/ml
- pH 5.5
- 20 mM His-HCl
- 210 mM trehalose
- 0.04% PS20
- 10 mM methionine

Pertuzumab SC DS
- Pertuzumab: 120 mg/ml
- pH 5.5
- 20 mM His-HCl
- 200 mM sucrose
- 0.04% PS20
- 10 mM methionine rHuPH20
10 mg/mL rhuPH20 in His-HCl buffer pH 6.5, 130 mM NaCl, 0.05% (w/v) Polysorbate 80
Diluted ~ 435X in DP (negligible)

EBC = early breast cancer; GM = geometric mean; HMV = healthy male volunteer; IV = Intravenous SC = subcutaneous.

Vertical bars, when shown, represent 2.5 or 97.5 percentile confidence intervals on geometric mean.

Geometric Mean Serum Pertuzumab Concentration-Time Profile in HMV or EBC Patients EBC = early breast cancer; GM = geometric mean; HMV = healthy male volunteer; SC = subcutaneous.

Vertical bars, when shown, represent 2.5 or 97.5 percentile confidence intervals on geometric mean.

SUBCUTANEOUS HER2 ANTIBODY FORMULATIONS

CROSS REFERENCE TO RELATED APPLICATIONS

This application claims the benefit of priority under 35 USC § 119(e) of provisional Application No. 62/447,359, filed Jan. 17, 2017, the full disclosure of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Jan. 12, 2018, is named P34027-US_SL.txt and is 31,954 bytes in size.

FIELD OF THE INVENTION

The invention concerns fixed dose HER2 antibody formulations for subcutaneous administration and their use in the treatment of cancer. In particular, the invention concerns fixed dose pertuzumab formulations, subcutaneous formulations comprising pertuzumab and trastuzumab, and their use in the treatment of cancer.

BACKGROUND OF THE INVENTION

HER2 Antibodies

Members of the HER family of receptor tyrosine kinases are important mediators of cell growth, differentiation and survival. The receptor family includes four distinct members including epidermal growth factor receptor (EGFR, ErbB1, or HER1), HER2 (ErbB2 or $p185^{new}$), HER3 (ErbB3) and HER4 (ErbB4 or tyro2). Members of the receptor family have been implicated in various types of human malignancy.

A recombinant humanized version of the murine anti-HER2 antibody 4D5 (huMAb4D5-8, rhuMAb HER2, trastuzumab or HERCEPTIN®, U.S. Pat. No. 5,821,337) is clinically active in patients with HER2-overexpressing metastatic breast cancers that have received extensive prior anti-cancer therapy (Baselga et al., *J. Clin. Oncol.* 14:737-744 (1996)).

Trastuzumab received marketing approval from the Food and Drug Administration Sep. 25, 1998 for the treatment of patients with metastatic breast cancer whose tumors overexpress the HER2 protein. At present, trastuzumab is approved for use as a single agent or in combination with chemotherapy or hormone therapy in the metastatic setting, and as single agent or in combination with chemotherapy as adjuvant treatment for patients with early-stage HER2-positive breast cancer. trastuzumab-based therapy is now the recommended treatment for patients with HER2-positive early-stage breast cancer who do not have contraindications for its use (Herceptin® prescribing information; NCCN Guidelines, version 2.2011). trastuzumab plus docetaxel (or paclitaxel) is a registered standard of care in the first-line metastatic breast cancer (MBC) treatment setting (Slamon et al. N Engl J Med. 2001; 344(11):783-792. Marty et al. J Clin Oncol. 2005; 23(19):4265-4274).

Patients treated with the HER2 antibody trastuzumab are selected for therapy based on HER2 expression. See, for example, WO99/31140 (Paton et al.), US2003/0170234A1 (Hellmann, S), and US2003/0147884 (Paton et al.); as well as WO01/89566, US2002/0064785, and US2003/0134344 (Mass et al.). See, also, U.S. Pat. Nos. 6,573,043, 6,905,830, and US2003/0152987, Cohen et al., concerning immunohistochemistry (IHC) and fluorescence in situ hybridization (FISH) for detecting HER2 overexpression and amplification. Thus, the optimal management of metastatic breast cancer now takes into account not only a patient's general condition, medical history, and receptor status, but also the HER2 status.

Pertuzumab (also known as recombinant humanized monoclonal antibody 2C4 (rhuMAb 2C4); Genentech, Inc, South San Francisco) represents the first in a new class of agents known as HER dimerization inhibitors (HDI) and functions to inhibit the ability of HER2 to form active heterodimers or homodimers with other HER receptors (such as EGFR/HER1, HER2, HER3 and HER4). See, for example, Harari and Yarden *Oncogene* 19:6102-14 (2000); Yarden and Sliwkowski. *Nat Rev Mol Cell Biol* 2:127-37 (2001); Sliwkowski *Nat Struct Biol* 10:158-9 (2003); Cho et al. *Nature* 421:756-60 (2003); and Malik et al. *Pro Am Soc Cancer Res* 44:176-7 (2003).

Pertuzumab blockade of the formation of HER2-HER3 heterodimers in tumor cells has been demonstrated to inhibit critical cell signaling, which results in reduced tumor proliferation and survival (Agus et al. *Cancer Cell* 2:127-37 (2002)).

Pertuzumab has undergone testing as a single agent in the clinic with a phase Ia trial in patients with advanced cancers and phase II trials in patients with ovarian cancer and breast cancer as well as lung and prostate cancer. In a Phase I study, patients with incurable, locally advanced, recurrent or metastatic solid tumors that had progressed during or after standard therapy were treated with pertuzumab given intravenously every 3 weeks. pertuzumab was generally well tolerated. Tumor regression was achieved in 3 of 20 patients evaluable for response. Two patients had confirmed partial responses. Stable disease lasting for more than 2.5 months was observed in 6 of 21 patients (Agus et al. *Pro Am Soc Clin Oncol* 22:192 (2003)). At doses of 2.0-15 mg/kg, the pharmacokinetics of pertuzumab was linear, and mean clearance ranged from 2.69 to 3.74 mL/day/kg and the mean terminal elimination half-life ranged from 15.3 to 27.6 days. Antibodies to pertuzumab were not detected (Allison et al. *Pro Am Soc Clin Oncol* 22:197 (2003)).

US 2006/0034842 describes methods for treating ErbB-expressing cancer with anti-ErbB2 antibody combinations. US 2008/0102069 describes the use of trastuzumab and pertuzumab in the treatment of HER2-positive metastatic cancer, such as breast cancer. Baselga et al., *J Clin Oncol*, 2007 ASCO Annual Meeting Proceedings Part I, Col. 25, No. 18S (June 20 Supplement), 2007:1004 report the treatment of patients with pre-treated HER2-positive breast cancer, which has progressed during treatment with trastuzumab, with a combination of trastuzumab and pertuzumab. Portera et al., *J Clin Oncol*, 2007 ASCO Annual Meeting Proceedings Part I. Vol. 25, No. 18S (June 20 Supplement), 2007:1028 evaluated the efficacy and safety of trastuzumab+pertuzumab combination therapy in HER2-positive breast cancer patients, who had progressive disease on trastuzumab-based therapy. The authors concluded that further evaluation of the efficacy of combination treatment was required to define the overall risk and benefit of this treatment regimen.

Pertuzumab has been evaluated in Phase II studies in combination with trastuzumab in patients with HER2-positive metastatic breast cancer who have previously received trastuzumab for metastatic disease. One study, conducted by the National cancer Institute (NCI), enrolled 11 patients with previously treated HER2-positive metastatic breast cancer. Two out of the 11 patients exhibited a partial response (PR) (Baselga et al., *J Clin Oncol* 2007 ASCO Annual Meeting Proceedings; 25:185 (June 20 Supplement): 1004).

The results of a Phase II neoadjuvant study evaluating the effect of a novel combination regimen of pertuzumab and trastuzumab plus chemotherapy (docetaxel) in women with early-stage HER2-positive breast cancer, presented at the CTRC-AACR San Antonio Breast Cancer Symposium (SABCS), Dec. 8-12, 2010, showed that the two HER2 antibodies plus docetaxel given in the neoadjuvant setting prior to surgery significantly improved the rate of complete tumor disappearance (pathological complete response rate, pCR, of 45.8 percent) in the breast by more than half compared to trastuzumab plus docetaxel (pCR of 29.0 percent), p=0.014.

The Clinical Evaluation of pertuzumab and trastuzumab (CLEOPATRA) Phase II clinical study assessed the efficacy and safety of pertuzumab plus trastuzumab plus docetaxel, as compared with placebo plus trastuzumab plus docetaxel, as first-line treatment for patients with locally recurrent, unresectable, or metastatic HER2-positive breast cancer. The combination of pertuzumab plus trastuzumab plus docetaxel, as compared with placebo plus trastuzumab plus docetaxel, when used as first-line treatment for HER2-positive metastatic breast cancer, significantly prolonged progression-free survival, with no increase in cardiac toxic effects. (Baselga et al., *N Eng J Med* 2012 366:2, 109-119).

The Phase II clinical study NeoSphere assessed the efficacy and safety of neoadjuvant administration of pertuzumab and trastuzumab in treatment-naïve women (patients who has not received any previous cancer therapy) with operable, locally advanced, and inflammatory breast cancer. Patients give pertuzumab and trastuzumab plus docetaxel showed a significantly improved pathological complete response rate compared with those given trastuzumab plus docetaxel, without substantial differences in tolerability (Gianni et al., *Lancet Oncol* 2012 13(1):25-32). Results of 5-year follow-up are reported by Gianni et al., *Lancet Oncol* 2016 17(6):791-800).

Patent Publications related to HER2 antibodies include: U.S. Pat. Nos. 5,677,171; 5,720,937; 5,720,954; 5,725,856; 5,770,195; 5,772,997; 6,165,464; 6,387,371; 6,399,063; 6,015,567; 6,333,169; 4,968,603; 5,821,337; 6,054,297; 6,407,213; 6,639,055; 6,719,971; 6,800,738; 5,648,237; 7,018,809; 6,267,958; 6,695,940; 6,821,515; 7,060,268; 7,682,609; 7,371,376; 6,127,526; 6,333,398; 6,797,814; 6,339,142; 6,417,335; 6,489,447; 7,074,404; 7,531,645; 7,846,441; 7,892,549; 6,573,043; 6,905,830; 7,129,840; 7,344,840; 7,468,252; 7,674,589; 6,949,245; 7,485,302; 7,498,030; 7,501,122; 7,537,931; 7,618,631; 7,862,817; 7,041,292; 6,627,196; 7,371,379; 6,632,979; 7,097,840; 7,575,748; 6,984,494; 7,279,287; 7,811,773; 7,993,834; 7,435,797; 7,850,966; 7,485,704; 7,807,799; 7,560,111; 7,879,325; 7,449,184; 7,700,299; and US 2010/0016556; US 2005/0244929; US 2001/0014326; US 2003/0202972; US 2006/0099201; US 2010/0158899; US 2011/0236383; US 2011/0033460; US 2005/0063972; US 2006/018739; US 2009/0220492; US 2003/0147884; US 2004/0037823; US 2005/0002928; US 2007/0292419; US 2008/0187533; US 2003/0152987; US 2005/0100944; US 2006/0183150; US2008/0050748; US 2010/0120053; US 2005/0244417; US 2007/0026001; US 2008/0160026; US 2008/0241146; US 2005/0208043; US 2005/0238640; US 2006/0034842; US 2006/0073143; US 2006/0193854; US 2006/0198843; US 2011/0129464; US 2007/0184055; US 2007/0269429; US 2008/0050373; US 2006/0083739; US 2009/0087432; US 2006/0210561; US 2002/0035736; US 2002/0001587; US 2008/0226659; US 2002/0090662; US 2006/0046270; US 2008/0108096; US 2007/0166753; US 2008/0112958; US 2009/0239236; US 2004/008204; US 2009/0187007; US 2004/0106161; US 2011/0117096; US 2004/0048525; US 2004/0258685; US 2009/0148401; US 2011/0117097; US 2006/0034840; US 2011/0064737; US 2005/0276812; US 2008/0171040; US 2009/0202536; US 2006/0013819; US 2006/0018899; US 2009/0285837; US 2011/0117097; US 2006/0088523; US 2010/0015157; US 2006/0121044; US 2008/0317753; US2006/0165702; US 2009/0081223; US 2006/0188509; US 2009/0155259; US 2011/0165157; US 2006/0204505; US 2006/0212956; US 2006/0275305; US 2007/0009976; US 2007/0020261; US 2007/0037228; US 2010/0112603; US 2006/0067930; US 2007/0224203; US 2008/0038271; US 2008/0050385; 2010/0285010; US 2008/0102069; US 2010/0008975; US 2011/0027190; US 2010/0298156; US 2009/0098135; US 2009/0148435; US 2009/0202546; US 2009/0226455; US 2009/0317387; and US 2011/0044977.

Hyaluronidase Enzymes

Hyaluronidases are a group of generally neutral- or acid-active enzymes found throughout the animal kingdom. Hyaluronidases vary with respect to substrate specificity, and mechanism of action (WO 2004/078140). There are three general classes of hyaluronidases: 1. Mammalian-type hyaluronidases, (EC 3.2.1.35) which are endo-β-N-acetyl-hexosaminidases with tetrasaccharides and hexasaccharides as the major end products. They have both hydrolytic and transglycosidase activities, and can degrade hyaluronan and chondroitin sulfates (CS), generally C4-S and C6-S. 2. Bacterial hyaluronidases (EC 4.2.99.1) degrade hyaluronan and, and to various extents, CS and DS. They are endo-β-N-acetylhexosaminidases that operate by a beta elimination reaction that yields primarily disaccharide end products. 3. Hyaluronidases (EC 3.2.1.36) from leeches, other parasites, and crustaceans are endo-beta-glucuronidases that generate tetrasaccharide and hexasaccharide end products through hydrolysis of the β1-3 linkage.

Mammalian hyaluronidases can be further divided into two groups: neutral-active and acid-active enzymes. There are six hyaluronidase-like genes in the human genome, HYAL1, HYAL2, HYAL3, HYAL4, HYALP1 and PH20/SPAM1. HYALP1 is a pseudogene, and HYAL3 has not been shown to possess enzyme activity toward any known substrates. HYAL4 is a chondroitinase and exhibits little activity towards hyaluronan. HYAL1 is the prototypical acid-active enzyme and PH20 is the prototypical neutral-active enzyme. Acid-active hyaluronidases, such as HYAL1 and HYAL2 generally lack catalytic activity at neutral pH (i.e. pH 7). For example, HYAL1 has little catalytic activity in vitro over pH 4.5 [Frost I. G. and Stern, R., "A microtiter-based assay for hyaluronidase activity not requiring specialized reagents", *Anal. Biochemistry,* 1997; 251:263-269]. HYAL2 is an acid-active enzyme with a very low specific activity in vitro.

The hyaluronidase-like enzymes can also be characterized by those which are generally locked to the plasma membrane via a glycosylphosphatidyl inositol anchor such as human HYAL2 and human PH20 [Danilkovitch-Miagkova et al., *Proc. Natl. Acad. Sci. USA,* 2003; 100(8):4580-4585; Phelps et al., *Science* 1988; 240(4860): 1780-1782], and those which are generally soluble such as human HYAL1 [Frost, I. G. et al., "Purification, cloning, and expression of human plasma hyaluronidase", *Biochem. Biophys. Res. Commun.* 1997; 236(1):10-15]. However, there are variations from species to species: bovine PH20 for example is very loosely attached to the plasma membrane and is not anchored via a phospholipase sensitive anchor [Lalancette et al., *Biol. Reprod.*, 2001; 65(2):628-36]. This unique feature of bovine hyaluronidase has permitted the use of the soluble bovine testes hyaluronidase enzyme as an extract for clinical use (Wydase™, Hyalase™). Other PH20 species are lipid anchored enzymes that are generally not soluble without the use of detergents or lipases. For example, human PH20 is anchored to the plasma membrane via a GPI anchor. Attempts to make human PH20 DNA constructs that would not introduce a lipid anchor into the polypeptide resulted in either a catalytically inactive enzyme, or an insoluble enzyme [Arming et al., *Eur. J. Biochem.*, 1997; 247(3):810-4]. Naturally occurring macaque sperm hyaluronidase is found in both a soluble and membrane bound form. While the 64 kDa membrane bound form possesses enzyme activity at pH 7.0, the 54 kDa form is only active at pH 4.0 [Cherr et al., *Dev. Biol.*, 1996; 10; 175(1): 142-53]. Thus, soluble forms of PH20 are often lacking enzyme activity under neutral conditions.

WO2006/091871 describes that small amounts of soluble hyaluronidase glycoproteins (sHASEGPs) can be introduced into a formulation in order to facilitate the administration of therapeutic drug into the hypodermis. By rapidly depolymerizing HA in the extracellular space sHASEGP reduces the viscosity of the interstitium, thereby increasing hydraulic conductance and allowing for larger volumes to be administered safely and comfortably into the SC tissue. The increased hydraulic conductance induced by sHASEGP through reduced interstitial viscosity allows for greater dispersion, potentially increasing the systemic bioavailability of subcutaneously (SC) administered therapeutic drug.

When injected in the hypodermis, the depolymerization of HA by sHASEGP is localized to the injection site in the SC tissue. Experimental evidence shows that the sHASEGP is inactivated locally in the interstitial space with a half-life of 13 to 20 minutes in mice, without detectable systemic absorption in blood following single intravenous dose in CD-1 mice. Within the vascular compartment sHASEGP demonstrates a half-life of 2.3 and 5 minutes in mice and Cynomolgus monkeys, respectively, with doses up to 0.5 mg/kg. The rapid clearance of sHASEGP, combined with the continual synthesis of the HA substrate in the SC tissue, results in a transient and locally-active permeation enhancement for other co-injected molecules, the effects of which are fully reversible within 24 to 48 hours post administration [Bywaters G. L., et al., "Reconstitution of the dermal barrier to dye spread after Hyaluronidase injection", *Br. Med. J.*, 1951; 2 (4741): 1178-1183].

In addition to its effects on local fluid dispersion, sHASEGP also acts as absorption enhancer. Macromolecules greater than 16 kilodaltons (kDa) are largely excluded from absorption through the capillaries via diffusion and are mostly absorbed via the draining lymph nodes. A subcutaneously administered macromolecule such as e.g. a therapeutic antibody (molecular weight approximately 150 kDa) must therefore traverse the interstitial matrix before reaching the draining lymphatics for subsequent absorption into the vascular compartment. By increasing local dispersion, sHASEGP increases the rate (Ka) of absorption of many macromolecules. This leads to increased peak blood levels ($C_{max}$) and potentially to increased bioavailability relative to SC administration in the absence of sHASEGP [Bookbinder L. H., et al., "A recombinant human enzyme for enhanced interstitial transport of therapeutics", *J. Control. Release* 2006; 114: 230-241].

Hyaluronidase products of animal origin have been used clinically for over 60 years, primarily to increase the dispersion and absorption of other co-administered drugs and for hypodermoclysis (SC injection/infusion of fluid in large volume) [Frost G. I., "Recombinant human hyaluronidase (rHuPH20): an enabling platform for subcutaneous drug and fluid administration", *Expert Opinion on Drug Delivery*, 2007; 4: 427-440]. The details on the mechanism of action of hyaluronidases have been described in detail in the following publications: Duran-Reynolds F., "A spreading factor in certain snake venoms and its relation to their mode of action", *CR Soc Biol* Paris, 1938; 69-81; Chain E., "A mucolytic enzyme in testes extracts", Nature 1939; 977-978; Weissmann B., "The transglycosylative action of testicular hyaluronidase", *J. Biol. Chem.*, 1955; 216: 783-94; Tammi, R., Saamanen, A. M., Maibach, H. I., Tammi M., "Degradation of newly synthesized high molecular mass hyaluronan in the epidermal and dermal compartments of human skin in organ culture", *J. Invest. Dermatol.* 1991; 97:126-130; Laurent, U. B. G., Dahl, L. B., Reed, R. K., "Catabolism of hyaluronan in rabbit skin takes place locally, in lymph nodes and liver". *Exp. Physiol.* 1991; 76: 695-703; Laurent, T. C. and Fraser, J. R. E., "Degradation of Bioactive Substances: Physiology and Pathophysiology", Henriksen, J. H. (Ed) CRC Press, Boca Raton, Fla.; 1991. pp. 249-265; Harris, E. N., et al., "Endocytic function, glycosaminoglycan specificity, and antibody sensitivity of the recombinant human 190-kDa hyaluronan receptor for endocytosis (HARE)", *J. Biol. Chem.* 2004; 279:36201-36209; Frost, G. I., "Recombinant human hyaluronidase (rHuPH20): an enabling platform for subcutaneous drug and fluid administration", *Expert Opinion on Drug Delivery*, 2007; 4: 427-440. Hyaluronidase products approved in EU countries include Hylase® "Dessau" and Hyalase®. Hyaluronidase products of animal origin approved in the US include Vitrase™, Hydase™, and Amphadase™.

Stable lyophilized antibody formulations comprising a lyoprotectant, a buffer and a surfactant have been described by Andya et al. (WO 97/04801 and U.S. Pat. Nos. 6,267,958, 6,685,940, 6,821,151, 7,060,268). WO 2006/044908 provides antibody formulations, including monoclonal antibodies formulated in histidine-acetate buffer, pH 5.5 to 6.5, preferably 5.8 to 6.2. Anti-HER2 antibody formulations are disclosed in U.S. Pat. Nos. 8,372,396; 9,017,671. Subcutaneous anti-HER2 antibody formulations and their uses are described in U.S. Pat. No. 9,345,661. Intravenous fixed dose administration of pertuzumab is disclosed in U.S. Pat. Nos. 7,449,184 and 8,404,234.

SUMMARY OF THE INVENTION

In one aspect, the invention concerns an article of manufacture comprising a single dose vial containing a single fixed dose of a HER2 antibody comprising the variable light chain and variable heavy chain amino acid sequences of SEQ ID Nos. 7 and 8, respectively, wherein the fixed dose is about 600 mg or about 1200 mg. Preferably, the HER2 antibody is pertuzumab.

In one embodiment, the article of manufacture comprises two single dose vials, wherein a first vial contains a single fixed dose of about 1200 mg of pertuzumab, and a second vial contains a single fixed dose of about 600 mg of pertuzumab.

In a second embodiment, the article of manufacture comprises two single dose vials, wherein the first vial contains a single fixed dose of about 600 mg of pertuzumab and the second vial contains a single fixed dose of about 600 mg of trastuzumab.

In a third embodiment, the article of manufacture comprises two single dose vials, wherein the first vial contains a single fixed dose of about 1200 mg of pertuzumab and a second vial comprising a single fixed dose of 600 mg of trastuzumab.

In all embodiments, at least one of the single dose vials may contain the fixed dose(s) in a liquid formulation for subcutaneous administration.

In all embodiments, the liquid formulation for subcutaneous administration may further comprise a hyaluronidase enzyme, such as recombinant human hyaluronidase (rHuPH20). rHuPH20 may be present in an amount sufficient to result in an increase in the dispersion of the pertuzumab or trastuzumab contained in the same liquid formulation during subcutaneous administration.

rHuPH2 may be present in the trastuzumab-containing liquid formulation, for example at a concentration of between about 150 U/ml and 16,000 U/ml, or at a concentration of between about 600 U/ml and about 16,000 U/ml, or at a concentration of between about 1,000 U/ml and about 2,000 U/ml, e.g. at a concentration of about 2,000 U/ml or at a concentration of at least about 600 U/mL.

rHuPH20 may be present in the pertuzumab containing liquid formulation at a concentration of between about 600 U/ml and about 2,000 U/ml, such as at a concentration of about 600 U/mL, or at a concentration of about 667 U/ml, or at a concentration of about 1,000 U/mL, or at a concentration of about 2,000 U/mL.

In another embodiment, the single dose vial present in the article of manufacture further comprises a single fixed dose of trastuzumab.

In one embodiment the single fixed dose of pertuzumab and the single fixed dose of trastuzumab is contained in a single liquid formulation for subcutaneous administration, where the liquid formulation may, for example contain a single fixed dose of about 600 mg of pertuzumab and a single fixed dose of about 600 mg of trastuzumab, or a single fixed dose of about 1200 mg of pertuzumab and a single fixed dose of about 600 mg of trastuzumab.

The liquid formulation comprising the fixed dose of pertuzumab and fixed dose of pertuzumab may further comprise a hyaluronidase enzyme, such as recombinant human hyaluronidase (rHuPH20), which may be present in said liquid formulation in an amount sufficient to result in an increase in the dispersion of the pertuzumab and trastuzumab contained in the same liquid formulation during subcutaneous administration, such as at a concentration of at least about 600 U/mL, or at a concentration of between about 600 U/ml and about 2,000 U/ml, e.g. at a concentration of about 1,000 U/mL.

In some embodiments, the articles of manufacture herein further comprise a package insert instructing the user to administer the fixed dose(s) subcutaneously to a patient with HER2 positive cancer.

In one embodiment, the package insert instructs the user to administer the fixed doses of pertuzumab and trastuzumab subcutaneously to a patient with HER2 positive cancer.

In another embodiment, the package insert instructs the user to co-administer the fixed dose pertuzumab and the fixed dose of trastuzumab subcutaneously as two separate subcutaneous injections.

In a further embodiment, the package insert instructs the user to administer the fixed dose pertuzumab co-mixed with the fixed-dose trastuzumab, as a single subcutaneous injection.

In yet another embodiment, the package insert instructs the user to administer the fixed doses of pertuzumab and trastuzumab subcutaneously to a patient with HER2 positive cancer.

The cancer may, for example, be breast cancer, peritoneal cancer, fallopian tube cancer, lung cancer, colorectal cancer, biliary cancer or bladder cancer, such as early breast cancer (EBC) or metastatic breast cancer (MBC).

In another aspect, the invention concerns an article of manufacture comprising a 10-mL or 20-mL vial holding a single fixed dose of a HER2 antibody comprising the variable light and variable heavy amino acid sequences in SEQ ID Nos. 7 and 8, respectively, wherein the fixed dose is about 600 mg or about 1200 mg of the HER2 antibody, and a package insert instructing the user to administer the fixed dose subcutaneously to a patient with HER2 positive cancer.

In one embodiment, the HER2 antibody is pertuzumab.

In another embodiment, the fixed dose of pertuzumab is contained in a liquid formulation for subcutaneous administration, wherein the liquid formulation may, for example, comprise the pertuzumab at a concentration of about 100-150 mg/mL, e.g. at a concentration of about 120 mg/mL.

In various embodiments, the liquid formulation present in the article of manufacture further comprises recombinant human hyaluronidase (rHuPH20) in amount sufficient to result in an increase in the dispersion of the pertuzumab during subcutaneous administration, such as at a concentration of about 2,000 U/mL, or at a concentration of about 1,000 U/mL.

The article of manufacture may further comprise one of more excipients selected from the group consisting of buffering agents, stabilizers and surfactants.

In one embodiment, the buffering agent is suitable to adjust the pH to about 5.0 to 6.0, such as pH 5.5 to 5.7, e.g. 5.5. An exemplary buffer is a histidine buffer, such as L-histidine acetate.

The stabilizer may comprise sucrose and optionally methionine and/or trehalose

A preferred surfactant is polysorbate 20.

In a further aspect, the invention concerns an aqueous formulation for subcutaneous administration comprising pertuzumab at a concentration of about 120 mg/mL, rHuPH20 at a concentration of about 1000-2000 U/mL, an L-histidine buffer to adjust to pH to about 5.5-5.7, sucrose, methionine and polysorbate 20.

In one embodiment, the rHuPH20 is present at a concentration of about 1000 U/mL.

In another embodiment, the rHuPH20 is present at a concentration of about 2000 U/mL.

In a further embodiment, the of the aqueous solution is pH is 5.7.

The invention further concerns a liquid subcutaneous pharmaceutical composition comprising a fixed dose of pertuzumab and a fixed dose of trastuzumab co-formulated in an aqueous solution further comprising rHuPH20, a buffering agent suitable to adjust the pH to about 5.0 to 6.0, a stabilizer and a surfactant.

In one embodiment, the buffering agent is a histidine buffer.

In another embodiment, the buffering agent is L-histidine acetate.

In yet another embodiment, the pH is 5.5-5.7, e.g. 5.5.

In other embodiments, the liquid pharmaceutical composition comprises sucrose as a stabilizer, and may further comprise methionine and/or trehalose as a stabilizer.

In one specific aspect, the liquid pharmaceutical composition comprises 600 mg pertuzumab at a concentration of 60 mg/ml, 600 mg trastuzumab at a concentration of 60 mg/ml, 1,000 U/mL rHuPH20, 20 mM His-HCl pH 5.5, 105 mM trehalose, 100 mM sucrose, 0.04% polysorbate 20, 10 mM methionine, and sterile water for injection up to a total volume of 10 ml, which, for example, be contained in a 15-ml vial.

In another specific aspect, the liquid pharmaceutical composition comprises 1,200 mg pertuzumab at a concentration of 80 mg/ml, 600 mg trastuzumab at a concentration of 40 mg/ml, 1,000 U/mL rHuPH20, 20 mM His-HCl pH 5.5, 70 mM trehalose, 133 mM sucrose, 0.04% polysorbate 20, 10 mM methionine, and sterile water for injection up to a total volume of 15 ml, which may be contained in a 20-ml vial.

The above articles of manufacture may further comprise a package insert with instructions to subcutaneously administer the liquid pharmaceutical composition contained therein to a human subject with HER2 positive cancer, such as, for example, breast cancer, peritoneal cancer, fallopian tube cancer, lung cancer, colorectal cancer, biliary cancer and bladder cancer, e.g. early breast cancer (EBC) or metastatic breast cancer (MBC).

In a further aspect, the invention concerns a method for treating cancer comprising subcutaneously administering to a human subject with a HER2 positive cancer one or more fixed dose(s) of a HER2 antibody comprising the variable light and variable heavy amino acid sequences in SEQ ID Nos. 7 and 8, respectively, in an amount effective to treat the cancer, wherein the fixed dose is about 600 mg and/or about 1200 mg.

The HER2 antibody preferably is pertuzumab.

In one embodiment, the method comprises administering to the human subject pertuzumab at a fixed loading dose of about 1200 mg followed by at least one maintenance dose of about 600 mg.

In a second embodiment, the administration of the loading dose is followed by administration of multiple maintenance doses.

In a third embodiment, the first maintenance dose of pertuzumab is administered to the human subject approximately two weeks or approximately three weeks after administration of the loading dose of pertuzumab.

In further embodiments, the fixed doses of pertuzumab are administered to the human subject approximately every 2 weeks or approximately every 3 weeks.

The cancer may be HER2 positive cancer, such as breast cancer, peritoneal cancer, fallopian tube cancer, lung cancer, colorectal cancer, biliary cancer and bladder cancer, e.g. early breast cancer (EBC) or metastatic breast cancer (MBC).

Optionally, the method may further comprise administering a second therapeutic agent to the patient, such as a different HER2 antibody, e.g. trastuzumab, or a chemotherapeutic agent.

In one embodiment, the fixed dose pertuzumab is administered subcutaneously in combination with subcutaneously administered trastuzumab.

In another embodiment, the fixed dose pertuzumab and the trastuzumab are co-administered subcutaneously as two separate subcutaneous injections.

In yet another embodiment, the fixed dose pertuzumab is co-mixed with fixed dose trastuzumab, and administered as a single subcutaneous injection.

In a further embodiment, the fixed dose pertuzumab and fixed dose trastuzumab are administered as a single co-formulation for subcutaneous administration, such as any of the co-formulations described hereinabove and throughout the disclosure.

The chemotherapeutic agent, if administered, may, for example, be a taxane and/or an anthracycline, such as paclitaxel, docetaxel, daunorubicin, doxorubicin, and/or epirubicin.

BRIEF DESCRIPTION OF THE DRAWINGS

FIGS. 2A and 2B depict alignments of the amino acid sequences of the variable light ($V_L$) (FIG. 2A) and variable heavy ($V_H$) (FIG. 2B) domains of murine monoclonal antibody 2C4 (SEQ ID Nos. 5 and 6, respectively); $V_L$ and $V_H$ domains of variant 574/pertuzumab (SEQ ID NOs. 7 and 8, respectively), and human $V_L$ and $V_H$ consensus frameworks (hum κI, light kappa subgroup I; humIII, heavy subgroup III) (SEQ ID Nos. 9 and 10, respectively). Asterisks identify differences between variable domains of pertuzumab and murine monoclonal antibody 2C4 or between variable domains of pertuzumab and the human framework. Complementarity Determining Regions (CDRs) are in brackets.

FIGS. 3A and 3B show the amino acid sequences of pertuzumab light chain (FIG. 3A; SEQ ID NO. 11) and heavy chain (FIG. 3B; SEQ ID No. 12). CDRs are shown in bold. Calculated molecular mass of the light chain and heavy chain are 23,526.22 Da and 49,216.56 Da (cysteines in reduced form). The carbohydrate moiety is attached to Asn 299 of the heavy chain.

FIGS. 4A and 4B show the amino acid sequences of trastuzumab light chain (FIG. 4A; SEQ ID NO. 13) and heavy chain (FIG. 4B; SEQ ID NO. 14), respectively. Boundaries of the variable light and variable heavy domains are indicated by arrows.

FIGS. 5A and 5B depict a variant pertuzumab light chain sequence (FIG. 5A; SEQ ID NO. 15) and a variant pertuzumab heavy chain sequence (FIG. 5B; SEQ ID NO. 16), respectively.

FIG. 8 Study Overview.

FIG. 13 Overview of Adverse Events Part 1.

FIG. 14 Overview of Adverse Events Pat 1, No. of subjects.

FIG. 15 Most Common Adverse Events (all grades)—incidence >5% overall in study, No. of subjects FIG. 16 EGFR related toxicity FIG. 17 Injection Related Reactions and Injection Site Reactions FIG. 18 LVEF—ECHO Assessments FIG. 19 Compositions of the pertuzumab, trastuzumab and rHuPH20 Subcutaneous Drug Substances (SC DS) used in the preparation of the fixed-dose pertuzumab-trastuzumab Co-Formulations.

DETAILED DESCRIPTION OF THE PREFERRED EMBODIMENTS

I. Definitions

Figure 1:
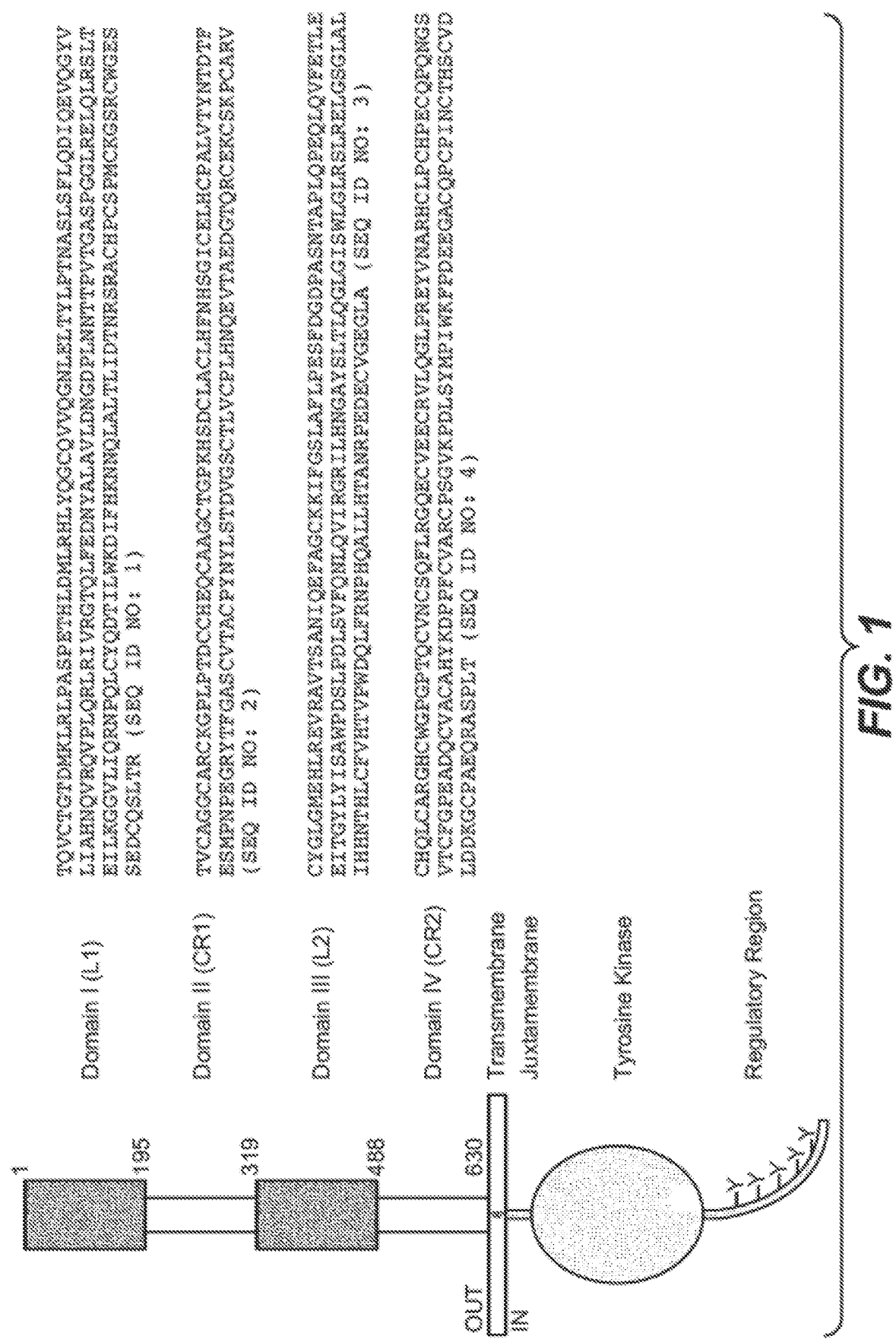
FIG. 1 provides a schematic of the HER2 protein structure, and amino acid sequences for Domains I-IV (SEQ ID Nos.1-4, respectively) of the extracellular domain thereof.

The term "pharmaceutical formulation" refers to a preparation which is in such form as to permit the biological activity of the active ingredient to be effective, and which contains no additional components which are unacceptably toxic to a subject to which the formulation would be administered. Such formulations are sterile.

A "sterile" formulation is aseptic or free from all living microorganisms and their spores.

A "stable" formulation is one in which the protein therein essentially retains its physical stability and/or chemical stability and/or biological activity upon storage. Preferably, the formulation essentially retains its physical and chemical stability, as well as its biological activity upon storage. The storage period is generally selected based on the intended shelf-life of the formulation. Various analytical techniques for measuring protein stability are available in the art and are reviewed in Peptide and Protein. Drug Delivery, 247-301, Vincent Lee Ed., Marcel Dekker, Inc., New York, N.Y., Pubs. (1991) and Jones, A. Adv. Drug Delivery Rev. 10: 29-90 (1993), for example. Stability can be measured at a selected temperature for a selected time period. Preferably, the formulation is stable at about 40° C. for at least about 2-4 weeks, and/or stable at about 5.0 and/or 15° C. for at least 3 months, and/or stable at about −20° C. for at least 3 months or at least 1 year. Furthermore, the formulation is preferably stable following freezing (to, e.g., −70° C.) and thawing of the formulation, for example following 1, 2 or 3 cycles of freezing and thawing. Stability can be evaluated qualitatively and/or quantitatively in a variety of different ways, including evaluation of aggregate formation (for example using size exclusion chromatography, by measuring turbidity, and/or by visual inspection); by assessing charge heterogeneity using cation exchange chromatography or capillary zone electrophoresis; amino-terminal or carboxy-terminal sequence analysis; mass spectrometric analysis; SDS-PAGE analysis to compare reduced and intact antibody; peptide map (for example tryptic or LYS-C) analysis; evaluating biological activity or antigen binding function of the antibody; etc. Instability may involve any one or more of: aggregation, deamidation (e.g. Asn deamidation), oxidation (e.g. Met oxidation), isomerization (e.g. Asp isomeriation), clipping/hydrolysis/fragmentation (e.g. hinge region fragmentation), succinimide formation, unpaired cysteine(s), N-terminal extension, C-terminal processing, glycosylation differences, etc.

An antibody which is "susceptible to deamidation" is one comprising one or more residue which has been found to be prone to deamidate.

An antibody which is "susceptible to aggregation" is one which has been found to aggregate with other antibody molecule(s), especially upon freezing and/or agitation.

An antibody which is "susceptible to fragmentation" is one which has been found to be cleaved into two or more fragments, for example at a hinge region thereof.

By "reducing deamidation, aggregation, or fragmentation" is intended preventing or decreasing the amount of deamidation, aggregation, or fragmentation relative to the monoclonal antibody formulated at a different pH or in a different buffer.

Herein, "biological activity" of a monoclonal antibody refers to the ability of the antibody to bind to antigen and result in a measurable biological response which can be measured in vitro or in vivo. In the case of pertuzumab, in one embodiment, the biological activity refers to the ability of the formulated antibody to inhibit proliferation of the human breast cancer cell line MDA-MB-175-VII.

By "isotonic" is meant that the formulation of interest has essentially the same osmotic pressure as human blood. Isotonic formulations will generally have an osmotic pressure from about 250 to 350 mOsm. Isotonicity can be measured using a vapor pressure or ice-freezing type osmometer, for example.

As used herein, "buffer" refers to a buffered solution that resists changes in pH by the action of its acid-base conjugate components. The buffer of this invention preferably has a pH in the range from about 5.0 to about 7.0, preferably from about 5.5 to about 6.5, for example from about 5.5 to about 6.2, such as, for example, 5.5 or 5.7. Examples of buffers that will control the pH in this range include acetate, succinate, succinate, gluconate, histidine, citrate, glycylglycine and other organic acid buffers. The preferred buffer herein is a histidine buffer.

A "histidine buffer" is a buffer comprising histidine ions. Examples of histidine buffers include histidine chloride, histidine acetate, histidine phosphate, histidine sulfate. The preferred histidine buffer identified in the examples herein was found to be histidine acetate. In the preferred embodiment, the histidine acetate buffer is prepared by titrating L-histidine (free base, solid) with acetic acid (liquid). Preferably, the histidine buffer or histidine-acetate buffer is at pH 5.5 to 6.5, or at pH 5.7 to 6.2, e.g. pH 5.7.

A "saccharide" herein comprises the general composition $(CH_2O)_n$ and derivatives thereof, including monosaccharides, disaccharides, trisaccharides, polysaccharides, sugar alcohols, reducing sugars, nonreducing sugars, etc.

Examples of saccharides herein include glucose, sucrose, trehalose, lactose, fructose, maltose, dextran, glycerin, dextran, erythritol, glycerol, arabitol, sylitol, sorbitol, mannitol, mellibiose, melezitose, raffinose, mannotriose, stachyose, maltose, lactulose, maltulose, glucitol, maltitol, lactitol, isomaltulose, etc. The preferred saccharide herein is a nonreducing disaccharide, such as trehalose or sucrose.

Herein, a "surfactant" refers to a surface-active agent, preferably a nonionic surfactant. Examples of surfactants herein include polysorbate (for example, polysorbate 20 and, polysorbate 80); poloxamer (e.g. poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl oleyl-taurate; and the MONAQUAT™ series (Mona Industries, Inc., Paterson, N.J.); polyethyl glycol, polypropyl glycol, and copolymers of ethylene and propylene glycol (e.g. Pluronics, PF68 etc), etc. The preferred surfactant herein is polysorbate 20.

A "HER receptor" is a receptor protein tyrosine kinase which belongs to the HER receptor family and includes EGFR, HER2, HER3 and HER4 receptors. The HER receptor will generally comprise an extracellular domain, which may bind an HER ligand and/or dimerize with another HER receptor molecule; a lipophilic transmembrane domain; a conserved intracellular tyrosine kinase domain; and a carboxyl-terminal signaling domain harboring several tyrosine residues which can be phosphorylated. The HER receptor may be a "native sequence" HER receptor or an "amino acid sequence variant" thereof. Preferably the HER receptor is native sequence human HER receptor.

The expressions "ErbB2" and "HER2" are used interchangeably herein and refer to human HER2 protein described, for example, in Semba et al., *PNAS (USA)* 82:6497-6501 (1985) and Yamamoto et al. *Nature* 319:230-234 (1986) (Genebank accession number X03363). The term "erbB2" refers to the gene encoding human ErbB2 and "neu" refers to the gene encoding rat p185$^{neu}$. Preferred HER2 is native sequence human HER2.

Herein, "HER2 extracellular domain" or "HER2 ECD" refers to a domain of HER2 that is outside of a cell, either anchored to a cell membrane, or in circulation, including fragments thereof. The amino acid sequence of HER2 is shown in FIG. 1. In one embodiment, the extracellular domain of HER2 may comprise four domains: "Domain I" (amino acid residues from about 1-195; SEQ ID NO: 1), "Domain II" (amino acid residues from about 196-319; SEQ ID NO: 2), "Domain III" (amino acid residues from about 320-488: SEQ ID NO: 3), and "Domain IV" (amino acid residues from about 489-630; SEQ ID NO: 4) (residue numbering without signal peptide). See Garrett et al. *Mol. Cell.* 11: 495-505 (2003), Cho et al. *Nature* 421: 756-760 (2003), Franklin et al. *Cancer Cell* 5:317-328 (2004), and Plowman et al. *Proc. Natl. Acad. Sci.* 90:1746-1750 (1993), as well as FIG. 1 herein.

"HER3" or "ErbB3" herein refer to the receptor as disclosed, for example, in U.S. Pat. Nos. 5,183,884 and 5,480,968 as well as Kraus et al. *PNAS (USA)* 86:9193-9197 (1989).

A "low HER3" cancer is one which expresses HER3 at a level less than the median level for HER3 expression in the cancer type. In one embodiment, the low HER3 cancer is epithelial ovarian, peritoneal, or fallopian tube cancer. HER3 DNA, protein, and/or mRNA level in the cancer can be evaluated to determine whether the cancer is a low HER3 cancer. See, for example, U.S. Pat. No. 7,981,418 for additional information about low HER3 cancer. Optionally, a HER3 mRNA expression assay is performed in order to determine that the cancer is a low HER3 cancer. In one embodiment, HER3 mRNA level in the cancer is evaluated, e.g. using polymerase chain reaction (PCR), such as quantitative reverse transcription PCR (qRT-PCR). Optionally, the cancer expresses HER3 at a concentration ratio equal or lower than about 2.81 as assessed qRT-PCR, e.g. using a COBAS z480® instrument.

A "HER dimer" herein is a noncovalently associated dimer comprising at least two HER receptors. Such complexes may form when a cell expressing two or more HER receptors is exposed to an HER ligand and can be isolated by immunoprecipitation and analyzed by SDS-PAGE as described in Sliwkowski et al., *J. Biol. Chem.*, 269(20): 14661-14665 (1994), for example. Other proteins, such as a cytokine receptor subunit (e.g. gp130) may be associated with the dimer. Preferably, the HER dimer comprises HER2.

A "HER heterodimer" herein is a noncovalently associated heterodimer comprising at least two different HER receptors, such as EGFR-HER2, HER2-HER3 or HER2-HER4 heterodimers.

A "HER antibody" is an antibody that binds to a HER receptor. Optionally, the HER antibody further interferes with HER activation or function. Preferably, the HER antibody binds to the HER2 receptor. HER2 antibodies of interest herein are pertuzumab and trastuzumab.

"HER activation" refers to activation, or phosphorylation, of any one or more HER receptors. Generally, HER activation results in signal transduction (e.g. that caused by an intracellular kinase domain of a HER receptor phosphorylating tyrosine residues in the HER receptor or a substrate polypeptide). HER activation may be mediated by HER ligand binding to a HER dimer comprising the HER receptor of interest. HER ligand binding to a HER dimer may activate a kinase domain of one or more of the HER receptors in the dimer and thereby results in phosphorylation of tyrosine residues in one or more of the HER receptors and/or phosphorylation of tyrosine residues in additional substrate polypeptides(s), such as Akt or MAPK intracellular kinases.

"Phosphorylation" refers to the addition of one or more phosphate group(s) to a protein, such as a HER receptor, or substrate thereof.

An antibody which "inhibits HER dimerization" is an antibody which inhibits, or interferes with, formation of a HER dimer. Preferably, such an antibody binds to HER2 at the heterodimeric binding site thereof. The most preferred dimerization inhibiting antibody herein is pertuzumab or MAb 2C4. Other examples of antibodies which inhibit HER dimerization include antibodies which bind to EGFR and inhibit dimerization thereof with one or more other HER receptors (for example EGFR monoclonal antibody 806, MAb 806, which binds to activated or "untethered" EGFR; see Johns et al., *J. Biol. Chem.* 279(29):30375-30384 (2004)); antibodies which bind to HER3 and inhibit dimerization thereof with one or more other HER receptors; and antibodies which bind to HER4 and inhibit dimerization thereof with one or more other HER receptors.

A "HER2 dimerization inhibitor" is an agent that inhibits formation of a dimer or heterodimer comprising HER2.

A "heterodimeric binding site" on HER2, refers to a region in the extracellular domain of HER2 that contacts, or interfaces with, a region in the extracellular domain of EGFR, HER3 or HER4 upon formation of a dimer therewith. The region is found in Domain II of HER2 (SEQ ID NO: 15). Franklin et al. *Cancer Cell* 5:317-328 (2004).

A HER2 antibody that "binds to a heterodimeric binding site" of HER2, binds to residues in Domain II (SEQ ID NO: 2) and optionally also binds to residues in other of the domains of the HER2 extracellular domain, such as domains I and III, SEQ ID NOs: 1 and 3), and can sterically hinder, at least to some extent, formation of a HER2-EGFR, HER2-HER3, or HER2-HER4 heterodimer. Franklin et al. *Cancer Cell* 5:317-328 (2004) characterize the HER2-pertuzumab crystal structure, deposited with the RCSB Protein Data Bank (ID Code IS78), illustrating an exemplary antibody that binds to the heterodimeric binding site of HER2.

An antibody that "binds to domain II" of HER2 binds to residues in domain II (SEQ ID NO: 2) and optionally residues in other domain(s) of HER2, such as domains I and III (SEQ ID NOs: 1 and 3, respectively). Preferably the antibody that binds to domain II binds to the junction between domains I, II and III of HER2.

For the purposes herein, "pertuzumab" and "rhuMAb 2C4", which are used interchangeably, refer to an antibody comprising the variable light and variable heavy amino acid sequences in SEQ ID NOs: 7 and 8, respectively. Where pertuzumab is an intact antibody, it preferably comprises an IgG1 antibody; in one embodiment comprising the light chain amino acid sequence in SEQ ID NO: 11 or 15, and heavy chain amino acid sequence in SEQ ID NO: 12 or 16. The antibody is optionally produced by recombinant Chinese Hamster Ovary (CHO) cells. The terms "pertuzumab" and "rhuMAb 2C4" herein cover biosimilar versions of the drug with the United States Adopted Name (USAN) or International Nonproprietary Name (INN): pertuzumab.

For the purposes herein, "trastuzumab" and rhuMAb4D5", which are used interchangeably, refer to an antibody comprising the variable light and variable heavy amino acid sequences from within SEQ ID Nos: 13 and 14, respectively. Where trastuzumab is an intact antibody, it preferably comprises an IgG1 antibody; in one embodiment comprising the light chain amino acid sequence of SEQ ID NO: 13 and the heavy chain amino acid sequence of SEQ ID NO: 14. The antibody is optionally produced by Chinese Hamster Ovary (CHO) cells. The terms "trastuzumab" and "rhuMAb4D5" herein cover biosimilar versions of the drug with the United States Adopted Name (USAN) or International Nonproprietary Name (INN): trastuzumab.

The term "antibody" herein is used in the broadest sense and specifically covers monoclonal antibodies, polyclonal antibodies, multispecific antibodies (e.g. bispecific antibodies), and antibody fragments, so long as they exhibit the desired biological activity.

"Humanized" forms of non-human (e.g., rodent) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992) Humanized HER2 antibodies specifically include trastuzumab (HERCEPTIN®) as described in Table 3 of U.S. Pat. No. 5,821,337 expressly incorporated herein by reference and as defined herein; and humanized 2C4 antibodies such as pertuzumab as described and defined herein.

An "intact antibody" herein is one which comprises two antigen binding regions, and an Fc region. Preferably, the intact antibody has a functional Fc region.

"Antibody fragments" comprise a portion of an intact antibody, preferably comprising the antigen binding region thereof. Examples of antibody fragments include Fab, Fab', $F(ab')_2$, and Fv fragments; diabodies; linear antibodies; single-chain antibody molecules; and multispecific antibodies formed from antibody fragment(s).

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end. The constant domain of the light chain is aligned with the first constant domain of the heavy chain, and the light-chain variable domain is aligned with the variable domain of the heavy chain. Particular amino acid residues are believed to form an interface between the light chain and heavy chain variable domains.

The term "hypervariable region" when used herein refers to the amino acid residues of an antibody which are responsible for antigen-binding. The hypervariable region generally comprises amino acid residues from a "complementarity determining region" or "CDR" (e.g. residues 24-34 (L1), 50-56 (L2) and 89-97 (L3) in the light chain variable domain and 31-35 (H1), 50-65 (H2) and 95-102 (H3) in the heavy chain variable domain; Kabat et al., *Sequences of Proteins of Immunological Interest*, 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk *J. Mol. Biol.* 196:901-917 (1987)). "Framework Region" or "FR" residues are those variable domain residues other than the hypervariable region residues as herein defined.

The term "Fc region" herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue.

Unless indicated otherwise, herein the numbering of the residues in an immunoglobulin heavy chain is that of the EU index as in Kabat et al., *Sequences of Proteins of Immunological Interest,* 5th Ed. Public Health Service, National Institutes of Health, Bethesda, Md. (1991), expressly incorporated herein by reference. The "EU index as in Kabat" refers to the residue numbering of the human IgG1 EU antibody.

A "functional Fc region" possesses an "effector function" of a native sequence Fc region. Exemplary "effector functions" include Clq binding; complement dependent cytotoxicity; Fc receptor binding; antibody-dependent cell-mediated cytotoxicity (ADCC); phagocytosis; down regulation of cell surface receptors (e.g. B cell receptor; BCR), etc. Such effector functions generally require the Fc region to be combined with a binding domain (e.g. an antibody variable domain) and can be assessed using various assays as herein disclosed, for example.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

Depending on the amino acid sequence of the constant domain of their heavy chains, intact antibodies can be assigned to different "classes". There are five major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called α, δ, ε, γ, and μ, respectively. The subunit structures and three-dimensional configurations of different classes of immunoglobulins are well known.

A "naked antibody" is an antibody that is not conjugated to a heterologous molecule, such as a cytotoxic moiety or radiolabel.

An "affinity matured" antibody is one with one or more alterations in one or more hypervariable regions thereof which result an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. *Bio/Technology* 10:779-783 (1992) describes affinity maturation by VH and VL domain shuffling. Random mutagenesis of CDR and/or framework residues is described by: Barbas et al. *Proc Nat. Acad. Sci, USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

A "deamidated" antibody is one in which one or more asparagine residues thereof has been derivitized, e.g. to an aspartic acid, a succinimide, or an iso-aspartic acid.

The terms "cancer" and "cancerous" refer to or describe the physiological condition in mammals that is typically characterized by unregulated cell growth.

An "advanced" cancer is one which has spread outside the site or organ of origin, either by local invasion ("locally advanced") or metastasis ("metastatic"). Accordingly, the term "advanced" cancer includes both locally advanced and metastatic disease.

"Metastatic" cancer refers to cancer which has spread from one part of the body (e.g. the breast) to another part of the body.

A "refractory" cancer is one which progresses even though an anti-tumor agent, such as a chemotherapy or biologic therapy, such as immunotherapy, is being administered to the cancer patient. An example of a refractory cancer is one which is platinum refractory.

A "recurrent" cancer is one which has regrown, either at the initial site or at a distant site, after a response to initial therapy, such as surgery.

A "locally recurrent" cancer is cancer that returns after treatment in the same place as a previously treated cancer.

A "non-resectable" or "unresectable" cancer is not able to be removed (resected) by surgery.

"Early-stage breast cancer" herein refers to breast cancer that has not spread beyond the breast or the axillary lymph nodes. Such cancer is generally treated with neoadjuvant or adjuvant therapy.

"Neoadjuvant therapy" or "neoadjuvant treatment" or "neoadjuvant administration" refers to systemic therapy given prior to surgery.

"Adjuvant therapy" or "adjuvant treatment" or "adjuvant administration" refers to systemic therapy given after surgery.

Herein, a "patient" or "subject" is a human patient. The patient may be a "cancer patient," i.e. one who is suffering or at risk for suffering from one or more symptoms of cancer, in particular breast cancer.

A "patient population" refers to a group of cancer patients. Such populations can be used to demonstrate statistically significant efficacy and/or safety of a drug, such as pertuzumab and/or trastuzumab.

A "relapsed" patient is one who has signs or symptoms of cancer after remission. Optionally, the patient has relapsed after adjuvant or neoadjuvant therapy.

A cancer or biological sample which "displays HER expression, amplification, or activation" is one which, in a diagnostic test, expresses (including overexpresses) a HER receptor, has amplified HER gene, and/or otherwise demonstrates activation or phosphorylation of a HER receptor.

A cancer or biological sample which "displays HER activation" is one which, in a diagnostic test, demonstrates activation or phosphorylation of a HER receptor. Such activation can be determined directly (e.g. by measuring HER phosphorylation by ELISA) or indirectly (e.g. by gene expression profiling or by detecting HER heterodimers, as described herein).

A cancer cell with "HER receptor overexpression or amplification" is one which has significantly higher levels of a HER receptor protein or gene compared to a noncancerous cell of the same tissue type. Such overexpression may be caused by gene amplification or by increased transcription or translation. HER receptor overexpression or amplification may be determined in a diagnostic or prognostic assay by evaluating increased levels of the HER protein present on the surface of a cell (e.g. via an immunohistochemistry assay; IHC). Alternatively, or additionally, one may measure levels of HER-encoding nucleic acid in the cell, e.g. via in situ hybridization (ISH), including fluorescent in situ hybridization (FISH; see WO98/45479 published October, 1998) and chromogenic in situ hybridization (CISH; see, e.g. Tanner et al., *Am. J. Pathol.* 157(5): 1467-1472 (2000); Bella et al., *J. Clin. Oncol.* 26: (May 20 suppl; abstr 22147) (2008)), southern blotting, or polymerase chain reaction (PCR) techniques, such as quantitative real time PCR (qRT-PCR). One may also study HER receptor overexpression or amplification by measuring shed antigen (e.g., HER extracellular domain) in a biological fluid such as serum (see, e.g., U.S. Pat. No. 4,933,294 issued Jun. 12, 1990; WO91/05264 published Apr. 18, 1991; U.S. Pat. No. 5,401,638 issued Mar. 28, 1995; and Sias et al. *J. Immunol. Methods* 132: 73-80 (1990)). Aside from the above assays, various in vivo assays are available to the skilled practitioner. For example, one may expose cells within the body of the patient to an antibody which is optionally labeled with a detectable label, e.g. a radioactive in situ for radioactivity or by analyzing a biopsy taken from a patient previously exposed to the antibody.

A "HER2-positive" cancer comprises cancer cells which have higher than normal levels of HER2. Optionally, HER2-positive cancer has an immunohistochemistry (IHC) score of 2+ or 3+ and/or is in situ hybridization (ISH), fluorescent in situ hybridization (FISH) or chromogenic in situ hybridization (CISH) positive, e.g. has an ISH/FISH/CISH amplification ratio of ≥2.0.

A "HER2-mutated" cancer comprises cancer cells with a HER2-activating mutation, including kinase domain mutations, which can, for example, be identified by next generation sequencing (NGS) or real-time polymerase chain reaction (RT-PCR). "HER2-mutated" cancer specifically includes cancer characterized by insertions in exon 20 of HER2, deletions around amino acid residues 755-759 of HER2, any of the mutations G309A, G309E, S310F, D769H, D769Y, V777L, P780-Y781insGSP, V842I, R896C (Bose et al., Cancer Discov 2013; 3:1-14), as well as previously reported identical non-synonymous putative activating mutations (or indels) in COSMIC database found in two or more unique specimens. For further details see, e.g. Stephens et al., *Nature* 2004; 431:525-6; Shigematsu et al., *Cancer Res* 2005; 65:1642-6; Buttitta et al., *Int J Cancer* 2006; 119:2586-91; Li et al., *Oncogene* 2008; 27:4702-11; Sequist et al., *J Clin Oncol* 2010; 28:3076-83; Arcila et al., *Clin Cancer Res* 2012; 18:4910-8; Greulich et al., *Proc Natl Acad Sci USA* 2012; 109:14476-81; and Herter-Sprie et al., *Front Oncol* 2013; 3:1-10.

Herein, an "anti-tumor agent" refers to a drug used to treat cancer. Non-limiting examples of anti-tumor agents herein include chemotherapy agents, HER dimerization inhibitors, HER antibodies, antibodies directed against tumor associated antigens, anti-hormonal compounds, cytokines, EGFR-targeted drugs, anti-angiogenic agents, tyrosine kinase inhibitors, growth inhibitory agents and antibodies, cytotoxic agents, antibodies that induce apoptosis, COX inhibitors, farnesyl transferase inhibitors, antibodies that binds oncofetal protein CA 125, HER2 vaccines, Raf or ras inhibitors, liposomal doxorubicin, topotecan, taxane, dual tyrosine kinase inhibitors, TLK286, EMD-7200, pertuzumab, trastuzumab, erlotinib, and bevacizumab.

The "epitope 2C4" is the region in the extracellular domain of HER2 to which the antibody 2C4 binds. In order to screen for antibodies which bind essentially to the 2C4 epitope, a routine cross-blocking assay such as that described in *Antibodies, A Laboratory Manual*, Cold Spring Harbor Laboratory, Ed Harlow and David Lane (1988), can be performed. Preferably the antibody blocks 2C4's binding to HER2 by about 50% or more. Alternatively, epitope mapping can be performed to assess whether the antibody binds essentially to the 2C4 epitope of HER2. Epitope 2C4 comprises residues from Domain II (SEQ ID NO: 2) in the extracellular domain of HER2. 2C4 and pertuzumab binds to the extracellular domain of HER2 at the junction of domains I, II and III (SEQ ID NOs: 1, 2, and 3, respectively). Franklin et al. *Cancer Cell* 5:317-328 (2004).

The "epitope 4D5" is the region in the extracellular domain of HER2 to which the antibody 4D5 (ATCC CRL 10463) and trastuzumab bind. This epitope is close to the transmembrane domain of HER2, and within Domain IV of HER2 (SEQ ID NO: 4). To screen for antibodies which bind essentially to the 4D5 epitope, a routine cross-blocking assay such as that described in *Antibodies, A Laboratory Manual*, Cold Spring Harbor Laboratory, Ed Harlow and David Lane (1988), can be performed. Alternatively, epitope mapping can be performed to assess whether the antibody binds essentially to the 4D5 epitope of HER2 (e.g. any one or more residues in the region from about residue 529 to about residue 625, inclusive of the HER2 ECD, residue numbering including signal peptide).

"Treatment" refers to both therapeutic treatment and prophylactic or preventative measures. Those in need of treatment include those already with cancer as well as those in which cancer is to be prevented. Hence, the patient to be treated herein may have been diagnosed as having cancer or may be predisposed or susceptible to cancer.

The term "effective amount" refers to an amount of a drug effective to treat cancer in the patient. The effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. The effective amount may extend progression free survival (e.g. as measured by Response Evaluation Criteria for Solid Tumors, RECIST, or CA-125 changes), result in an objective response (including a partial response, PR, or complete response, CR), increase overall survival time, and/or improve one or more symptoms of cancer (e.g. as assessed by FOSI).

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins such as small molecule toxins or enzymatically active toxins of bacterial, fungal, plant or animal origin, including fragments and/or variants thereof.

A "chemotherapy" is use of a chemical compound useful in the treatment of cancer. Examples of chemotherapeutic agents, used in chemotherapy, include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; TLK 286 (TELCYTA™); acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; bisphosphonates, such as clodronate; antibiotics such as the enediyne antibiotics (e.g., calicheamicin, especially calicheamicin gamma II and caliceamicin omega II (see, e.g., Agnew, Chem Intl. Ed. Engl., 33: 183-186 (1994)) and anthracyclines such as annamycin, AD 32, alcarubicin, daunorubicin, doxorubicin, dexrazoxane, DX-52-1, epirubicin, GPX-100, idarubicin, valrubicin, KRN5500, menogaril, dynemicin, including dynemicin A, an esperamicin, neocarzinostatin chromophore and related chromoprotein enediyne antiobiotic chromophores, aclacinomysins, actinomycin, authramycin, azaserine, bleomycins, cactinomycin, carabicin, carminomycin, carzinophilin, chromomycinis, dactinomycin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin, liposomal doxorubicin, and deoxydoxorubicin), esorubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, and zorubicin; folic acid analogues such as denopterin, pteropterin, and trimetrexate; purine analogs such as fludarabine, 6-mercaptopurine, thiamiprine, and thioguanine; pyrimidine analogs such as ancitabine, azacitidine, 6-azauridine, carmofur, cytarabine, dideoxyuridine, doxifluridine, enocitabine, and floxuridine; androgens such as calusterone, dromostanolone propionate, epitiostanol, mepitiostane, and testolactone; antiadrenals such as aminoglutethimide, mitotane, and trilostane; folic acid replenisher such as folinic acid (leucovorin); aceglatone; anti-folate anti-neoplastic agents such as ALIMTA®, LY231514 pemetrexed, dihydrofolate reductase inhibitors such as methotrexate, anti-metabolites such as 5-fluorouracil (5-FU) and its prodrugs such as UFT, S-1 and capecitabine, and thymidylate synthase inhibitors and glycinamide ribonucleotide formyltransferase inhibitors such as raltitrexed (TOMUDEX$^{RM}$, TDX); inhibitors of dihydropyrimidine dehydrogenase such as eniluracil; aldophosphamide glycoside; aminolevulinic acid; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); cyclophosphamide; thiotepa; taxanes; chloranbucil; gemcitabine (GEMZAR®); 6-thioguanine; mercaptopurine; platinum; platinum analogs or platinum-based analogs such as cisplatin, oxaliplatin and carboplatin; vinblastine (VELBAN®); etoposide (VP-16); ifosfamide; mitoxantrone; vincristine (ONCOVIN®); vinca alkaloid; vinorelbine (NAVELBINE®); novantrone; edatrexate; daunomycin; aminopterin; xeloda; ibandronate; topoisomerase inhibitor RFS 2000; difluorometlhylornithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovorin.

Also included in this definition are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON® toremifene; aromatase inhibitors; and anti-androgens such as flutamide, nilutamide, bicalutamide, leuprolide, and goserelin; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; and pharmaceutically acceptable salts, acids or derivatives of any of the above.

A "taxane" is a chemotherapy which inhibits mitosis and interferes with microtubules. Examples of taxanes include Paclitaxel (TAXOL®; Bristol-Myers Squibb Oncology, Princeton, N.J.); cremophor-free, albumin-engineered nanoparticle formulation of paclitaxel or nab-paclitaxel (ABRAXANE™; American Pharmaceutical Partners, Schaumberg, Ill.); and Docetaxel (TAXOTERE®; Rhône-Poulenc Rorer, Antony, France).

An "anthacycline" is a type of antibiotic that comes from the fungus *Streptococcus peucetius*, examples include: Daunorubicin, Doxorubicin, Epirubicin, and any other anthracycline chemotherapeutic agents, including those listed before.

"Anthracycline-based chemotherapy" refers to a chemotherapy regimen that consists of or includes one or more anthracycline. Examples include, without limitation, 5-FU, epirubicin, and cyclophosphamide (FEC); 5-FU, doxorubicin, and cyclophosphamide (FAC); doxorubicin and cyclophosphamide (AC); epirubicin and cyclophosphamide (EC); dose-dense doxorubicin and cyclophosphamide (ddAC), and the like.

For the purposes herein, "carboplatin-based chemotherapy" refers to a chemotherapy regimen that consists of or includes one or more Carboplatins. An example is TCH (Docetaxel/TAXOL®, Carboplatin, and trastuzumab/HERCEPTIN®).

An "aromatase inhibitor" inhibits the enzyme aromatase, which regulates estrogen production in the adrenal glands. Examples of aromatase inhibitors include: 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole. In one embodiment, the aromatase inhibitor herein is letrozole or anastrozole.

An "antimetabolite chemotherapy" is use of an agent which is structurally similar to a metabolite, but cannot be used by the body in a productive manner. Many antimetabolite chemotherapy interferes with the production of the nucleic acids, RNA and DNA. Examples of antimetabolite chemotherapeutic agents include gemcitabine (GEMZAR®), 5-fluorouracil (5-FU), capecitabine (XELODA™), 6-mercaptopurine, methotrexate, 6-thioguanine, pemetrexed, raltitrexed, arabinosylcytosine ARA-C cytarabine (CYTOSAR-U®), dacarbazine (DTIC-DOME®), azocytosine, deoxycytosine, pyridmidene, fludarabine (FLUDARA®), cladrabine, 2-deoxy-D-glucose etc.

By "chemotherapy-resistant" cancer is meant that the cancer patient has progressed while receiving a chemotherapy regimen (i.e. the patient is "chemotherapy refractory"), or the patient has progressed within 12 months (for instance, within 6 months) after completing a chemotherapy regimen.

The term "platin" is used herein to refer to platinum based chemotherapy, including, without limitation, cisplatin, carboplatin, and oxaliplatin.

The term "fluoropyrimidine" is used herein to refer to an antimetabolite chemotherapy, including, without limitation, capecitabine, floxuridine, and fluorouracil (5-FU).

A "fixed" or "flat" dose of a therapeutic agent herein refers to a dose that is administered to a human patient without regard for the weight (WT) or body surface area (BSA) of the patient. The fixed or flat dose is therefore not provided as a mg/kg dose or a mg/m$^2$ dose, but rather as an absolute amount of the therapeutic agent.

A "loading" dose herein generally comprises an initial dose of a therapeutic agent administered to a patient, and is followed by one or more maintenance dose(s) thereof. Generally, a single loading dose is administered, but multiple loading doses are contemplated herein. Usually, the amount of loading dose(s) administered exceeds the amount of the maintenance dose(s) administered and/or the loading dose(s) are administered more frequently than the maintenance dose(s), so as to achieve the desired steady-state concentration of the therapeutic agent earlier than can be achieved with the maintenance dose(s).

A "maintenance" dose herein refers to one or more doses of a therapeutic agent administered to the patient over a treatment period. Usually, the maintenance doses are administered at spaced treatment intervals, such as approximately every week, approximately every 2 weeks, approximately every 3 weeks, or approximately every 4 weeks, preferably every 3 weeks.

A "vial" is a container suitable for holding a liquid or lyophilized preparation. In one embodiment, the vial is a single-use vial, e.g. a 10 ml or a 20 ml single-use vial with a stopper, such as a 10 ml single use glass vial with a 20 mm stopper.

A "package insert" is a leaflet that, by order of the Food and Drug Administration (FDA) or other Regulatory Authority, must be placed inside the package of every prescription drug. The leaflet generally includes the trademark for the drug, its generic name, and its mechanism of action; states its indications, contraindications, warnings, precautions, adverse effects, and dosage forms; and includes instructions for the recommended dose, time, and route of administration.

The expression "safety data" concerns the data obtained in a controlled clinical trial showing the prevalence and severity of adverse events to guide the user regarding the safety of the drug, including guidance on how to monitor and prevent adverse reactions to the drug.

"Efficacy data" refers to the data obtained in controlled clinical trial showing that a drug effectively treats a disease, such as cancer.

By "stable mixture" when referring to a mixture of two or more drugs, such as pertuzumab and trastuzumab, means that each of the drugs in the mixture essentially retains its physical and chemical stability in the mixture as evaluated by one or more analytical assays. Exemplary analytical assays for this purpose include: color, appearance and clarity (CAC), concentration and turbidity analysis, particulate analysis, size exclusion chromatography (SEC), ion-exchange chromatography (IEC), capillary zone electrophoresis (CZE), image capillary isoelectric focusing (iCIEF), and potency assay. In one embodiment, mixture has been shown to be stable for up to 24 hours at 5° C. or 30° C.

Administration "in combination" encompasses combined administration and separate administration, in which case, administration of one therapeutic agent can occur prior to, simultaneously, and/or following, administration of another therapeutic agents. Thus, administration of pertuzumab and trastuzumab in combination (or administration of a combination of pertuzumab and trastuzumab) encompasses combined administration and separate administration in either order.

A drug that is administered "concurrently" with one or more other drugs is administered during the same treatment cycle, on the same day of treatment as the one or more other drugs, and, optionally, at the same time as the one or more other drugs. For instance, for cancer therapies given every 3-weeks, the concurrently administered drugs are each administered on day-1 of a 3-week cycle.

The term "co-administration" is used herein to refer to separate administration, including, for example, administration of pertuzumab and trastuzumab as two separate subcutaneous (SC) injections.

The term "co-mixed" is used herein to refer to simultaneous administration as a single injection, including, for example, administration of pertuzumab and trastuzumab as a single subcutaneous (SC) injection, prepared by the health professional on site, immediately prior to SC administration by mixing separate pertuzumab and trastuzumab formulations.

The term "co-formulation" is used herein to refer to a single ready-to-use pharmaceutical formulation comprising two or more active ingredients, including, for example, a single ready-to-use pharmaceutical formulation comprising pertuzumab and trastuzumab formulated together for subcutaneous (SC) administration.

II. Antibody and Chemotherapy Compositions (i) HER2 Antibodies

The HER2 antigen to be used for production of antibodies may be, e.g., a soluble form of the extracellular domain of a HER2 receptor or a portion thereof, containing the desired epitope. Alternatively, cells expressing HER2 at their cell surface (e.g. NIH-3T3 cells transformed to overexpress HER2; or a carcinoma cell line such as SK-BR-3 cells, see Stancovski et al. *PNAS (USA)* 88:8691-8695 (1991)) can be used to generate antibodies. Other forms of HER2 receptor useful for generating antibodies will be apparent to those skilled in the art.

Various methods for making monoclonal antibodies herein are available in the art. For example, the monoclonal antibodies may be made using the hybridoma method first described by Kohler et al., *Nature*, 256:495 (1975), by recombinant DNA methods (U.S. Pat. No. 4,816,567).

The anti-HER2 antibodies used in accordance with the present invention, pertuzumab and trastuzumab, are commercially available.

U.S. Pat. No. 6,949,245 describes production of exemplary humanized HER2 antibodies which bind HER2 and block ligand activation of a HER receptor.

Humanized HER2 antibodies specifically include trastuzumab as described in Table 3 of U.S. Pat. No. 5,821,337 expressly incorporated herein by reference and as defined herein; and humanized 2C4 antibodies such as pertuzumab as described and defined herein.

The humanized antibodies herein may, for example, comprise nonhuman hypervariable region residues incorporated into a human variable heavy domain and may further comprise a framework region (FR) substitution at a position selected from the group consisting of 69H, 71H and 73H utilizing the variable domain numbering system set forth in Kabat et al., *Sequences of Proteins of Immunological Interest*, 5th Ed. Public Health Service, National Institutes of Health, Bethesda, Md. (1991). In one embodiment, the humanized antibody comprises FR substitutions at two or all of positions 69H, 71H and 73H.

An exemplary humanized antibody of interest herein comprises variable heavy domain complementarity determining residues GFTFTDYTMX (SEQ ID NO: 17), where X is preferably D or S; DVNPNSGGSIYNQRFKG (SEQ ID NO: 18); and/or NLGPSFYFDY (SEQ ID NO: 19), optionally comprising amino acid modifications of those CDR residues, e.g. where the modifications essentially maintain or improve affinity of the antibody. For example, an antibody variant for use in the methods of the present invention may have from about one to about seven or about five amino acid substitutions in the above variable heavy CDR sequences. Such antibody variants may be prepared by affinity maturation, e.g., as described below.

The humanized antibody may comprise variable light domain complementarity determining residues KASQD-VSIGVA (SEQ ID NO: 20); SASYX$^1$X$^2$X$^3$, where X$^1$ is preferably R or L, X$^2$ is preferably Y or E, and X$^3$ is preferably T or S (SEQ ID NO: 21); and/or QQYYIYPYT (SEQ ID NO: 22), e.g. in addition to those variable heavy domain CDR residues in the preceding paragraph. Such humanized antibodies optionally comprise amino acid modifications of the above CDR residues, e.g. where the modifications essentially maintain or improve affinity of the antibody. For example, the antibody variant of interest may have from about one to about seven or about five amino acid substitutions in the above variable light CDR sequences. Such antibody variants may be prepared by affinity maturation, e.g., as described below.

The present application also contemplates affinity matured antibodies which bind HER2. The parent antibody may be a human antibody or a humanized antibody, e.g., one comprising the variable light and/or variable heavy sequences of SEQ ID Nos. 7 and 8, respectively (i.e. comprising the VL and/or VH of pertuzumab). An affinity matured variant of pertuzumab preferably binds to HER2 receptor with an affinity superior to that of murine 2C4 or pertuzumab (e.g. from about two or about four fold, to about 100 fold or about 1000 fold improved affinity, e.g. as assessed using a HER2-extracellular domain (ECD) ELISA). Exemplary variable heavy CDR residues for substitution include H28, H30, H34, H35, H64, H96, H99, or combinations of two or more (e.g. two, three, four, five, six, or seven of these residues). Examples of variable light CDR residues for alteration include L28, L50, L53, L56, L91, L92, L93, L94, L96, L97 or combinations of two or more (e.g. two to three, four, five or up to about ten of these residues).

Humanization of murine 4D5 antibody to generate humanized variants thereof, including trastuzumab, is described in U.S. Pat. Nos. 5,821,337, 6,054,297, 6,407,213, 6,639,055, 6,719,971, and 6,800,738, as well as Carter et al. PNAS (USA), 89:4285-4289 (1992). HuMAb4D5-8 (trastuzumab) bound HER2 antigen 3-fold more tightly than the mouse 4D5 antibody, and had secondary immune function (ADCC) which allowed for directed cytotoxic activity of the humanized antibody in the presence of human effector cells. HuMAb4D5-8 comprised variable light ($V_L$) CDR residues incorporated in a $V_L$ κ subgroup I consensus framework, and variable heavy ($V_H$) CDR residues incorporated into a $V_H$ subgroup III consensus framework. The antibody further comprised framework region (FR) substitutions as positions: 71, 73, 78, and 93 of the $V_H$ (Kabat numbering of FR residues; and a FR substitution at position 66 of the $V_L$ (Kabat numbering of FR residues). trastuzumab comprises non-A allotype human γ1 Fc region.

Various forms of the humanized antibody or affinity matured antibody are contemplated. For example, the humanized antibody or affinity matured antibody may be an antibody fragment. Alternatively, the humanized antibody or affinity matured antibody may be an intact antibody, such as an intact IgG1 antibody.

(ii) Pertuzumab Compositions

In one embodiment of a HER2 antibody composition, the composition comprises a mixture of a main species pertuzumab antibody and one or more variants thereof. The preferred embodiment herein of a pertuzumab main species antibody is one comprising the variable light and variable heavy amino acid sequences in SEQ ID Nos. 7 and 8, and most preferably comprising a light chain amino acid sequence of SEQ ID No. 11, and a heavy chain amino acid sequence of SEQ ID No. 12 (including deamidated and/or oxidized variants of those sequences). In one embodiment, the composition comprises a mixture of the main species pertuzumab antibody and an amino acid sequence variant thereof comprising an amino-terminal leader extension. Preferably, the amino-terminal leader extension is on a light chain of the antibody variant (e.g. on one or two light chains of the antibody variant). The main species HER2 antibody or the antibody variant may be an full length antibody or antibody fragment (e.g. Fab of F(ab')2 fragments), but preferably both are full length antibodies. The antibody variant herein may comprise an amino-terminal leader extension on any one or more of the heavy or light chains thereof. Preferably, the amino-terminal leader extension is on one or two light chains of the antibody. The amino-terminal leader extension preferably comprises or consists of VHS-. Presence of the amino-terminal leader extension in the composition can be detected by various analytical techniques including, but not limited to, N-terminal sequence analysis, assay for charge heterogeneity (for instance, cation exchange chromatography or capillary zone electrophoresis), mass spectrometry, etc. The amount of the antibody variant in the composition generally ranges from an amount that constitutes the detection limit of any assay (preferably N-terminal sequence analysis) used to detect the variant to an amount less than the amount of the main species antibody. Generally, about 20% or less (e.g. from about 1% to about 15%, for instance from 5% to about 15%) of the antibody molecules in the composition comprise an amino-terminal leader extension. Such percentage amounts are preferably determined using quantitative N-terminal sequence analysis or cation exchange analysis (preferably using a high-resolution, weak cation-exchange column, such as a PROPAC WCX-10™ cation exchange column). Aside from the amino-terminal leader extension variant, further amino acid sequence alterations of the main species antibody and/or variant are contemplated, including but not limited to an antibody comprising a C-terminal lysine residue on one or both heavy chains thereof, a deamidated antibody variant, etc.

Moreover, the main species antibody or variant may further comprise glycosylation variations, non-limiting examples of which include antibody comprising a G1 or G2 oligosaccharide structure attached to the Fc region thereof, antibody comprising a carbohydrate moiety attached to a light chain thereof (e.g. one or two carbohydrate moieties, such as glucose or galactose, attached to one or two light chains of the antibody, for instance attached to one or more lysine residues), antibody comprising one or two non-glycosylated heavy chains, or antibody comprising a sialidated oligosaccharide attached to one or two heavy chains thereof etc.

The composition may be recovered from a genetically engineered cell line, e.g. a Chinese Hamster Ovary (CHO) cell line expressing the HER2 antibody, or may be prepared by peptide synthesis.

For more information regarding exemplary pertuzumab compositions, see U.S. Pat. Nos. 7,560,111 and 7,879,325 as well as US 2009/0202546A1.

(iii) Trastuzumab Compositions

The trastuzumab composition generally comprises a mixture of a main species antibody (comprising light and heavy chain sequences of SEQ ID NOS: 13 and 14, respectively), and variant forms thereof, in particular acidic variants (including deamidated variants). Preferably, the amount of such acidic variants in the composition is less than about 25%, or less than about 20%, or less than about 15%. See, U.S. Pat. No. 6,339,142. See, also, Harris et al., *J. Chromatography, B* 752:233-245 (2001) concerning forms of trastuzumab resolvable by cation-exchange chromatography, including Peak A (Asn30 deamidated to Asp in both light chains); Peak B (Asn55 deamidated to isoAsp in one heavy chain); Peak 1 (Asn30 deamidated to Asp in one light chain); Peak 2 (Asn30 deamidated to Asp in one light chain, and Asp102 isomerized to isoAsp in one heavy chain); Peak 3 (main peak form, or main species antibody); Peak 4 (Asp102 isomerized to isoAsp in one heavy chain); and Peak C (Asp102 succinimide (Asu) in one heavy chain). Such variant forms and compositions are included in the invention herein.

(iv) Subcutaneous Formulations Comprising a Hyaluronidase Enzyme

Hyaluronidase enzyme acts primarily as a permeation enhancer to increase the dispersion and absorption of other co-administered drugs. Hyaluronidase transiently hydrolyses hyaluronan, component of the SC matrix, leading to reduced viscosity of the extracellular matrix of the hypodermis and, thus, to an improved delivery of subcutaneously administered drugs to the systemic circulation.

Soluble Hyaloronidase glycoproteins (sHASEGP), a process for preparing the same and their use in pharmaceutical compositions have been described in WO 2004/078140. The use of soluble Hyaluronidase glycoproteins in combination with a variety of exemplary antibodies, such as e.g. trastuzumab, has been mentioned in WO 2006/091871.

The hyaluronidase enzyme in the formulations of the present invention enhances the delivery of the anti-HER2 antibody or antibodies (e.g. pertuzumab and/or trastuzumab) to the systemic circulation, e.g. by increasing the absorption of the active substance (it acts as a permeation enhancer). The hyaluronidase enzyme also increases the delivery of the therapeutic HER2 antibody or antibodies (e.g. pertuzumab and/or trastuzumab) into the systemic circulation via the subcutaneous application route by the reversible hydrolyzation of hyaluronan, an extracellular component of the SC interstitial tissue. The hydrolysis of hyaluronan in the hypodermis temporarily opens channels in the interstitial space of the SC tissue and thereby improves the delivery of the therapeutic anti-HER2 antibody into the systemic circulation. In addition, the administration shows reduced pain in humans and less volume-derived swelling of the SC tissue.

Hyaluronidase, when administered locally has its entire effect locally. In other word hyaluronidase is inactivated and metabolized locally in minutes and has not been noted to have systemic or long term effects. The rapid inactivation of hyaluronidase within minutes when it enters the blood stream precludes a realistic ability to perform comparable biodistribution studies between different hyaluronidase products. This property also minimizes any potential systemic safety concerns because the hyaluronidase product cannot act at distant sites.

The unifying feature of all hyaluronidase enzymes is their ability to depolymerize hyaluronan, regardless of differences in chemical structure, in species source, in tissue sources, or in the batches of drug product sourced from the same species and tissue. They are unusual in that their activity is the same (except for potency) in spite of having different structures.

The hyaluronidase enzyme excipient in accordance with the formulation of the present invention is characterized by having no adverse effect on the molecular integrity of the HER2 antibody or antibodies in the stable pharmaceutical formulations described herein. Furthermore, the hyaluronidase enzyme merely modifies the delivery of the HER2 antibody or HER2 antibodies to the systemic circulation but does not possess any properties that could provide or contribute to the therapeutic effects of systemically absorbed HER2 antibody or antibodies. The hyaluronidase enzyme is not systemically bioavailable and does not adversely affect the molecular integrity of the HER2 antibody or antibodies at the recommended storage conditions of the stable pharmaceutical formulation in accordance with the invention.

A number of suitable hyaluronidase enzymes in accordance with the present invention are known from the prior art. The preferred enzyme is a human hyaluronidase enzyme, most preferably the recombinant human hyaluronidase enzyme known as rHuPH20. rHuPH20 is a member of the family of neutral and acid-active $\beta$-1,4 glycosyl hydrolases that depolymerize hyaluronan by the hydrolysis of the β-1,4 linkage between the $C_1$ position of N-acetyl glucosamine and the $C_4$ position of glucuronic acid. Hyaluronan is a polysaccharide found in the intracellular ground substance of connective tissue, such as the subcutaneous interstitial tissue, and of certain specialized tissues, such as the umbilical cord and vitreous humor. The hydrolysis of hyaluronan temporarily decreases the viscosity of the interstitial tissue and promotes the dispersion of injected fluids or of localized transudates or exudates, thus facilitating their absorption. The effects of hyaluronidase are local and reversible with complete reconstitution of the tissue hyaluronan occurring within 24 to 48 hours (Frost, G. I., "Recombinant human hyaluronidase (rHuPH20): an enabling platform for subcutaneous drug and fluid administration", Expert Opinion on Drug Delivery, 2007; 4:427-440). The increase in the permeability of connective tissue through the hydrolysis of hyaluronan correlates with the efficacy of hyaluronidase for their capability to increase the dispersion and absorption of co-administered molecules.

The human genome contains several hyaluronidase genes. Only the PH20 gene product possesses effective hyaluronidase activity under physiologic extracellular conditions and acts as a spreading agent, whereas acid-active hyaluronidases do not have this property.

rHuPH20 is the first and only recombinant human hyaluronidase enzyme currently available for therapeutic use. Naturally occurring human PH20 protein has a lipid anchor attached to the carboxy terminal amino acid that anchors it to the plasma membrane. The rHuPH20 enzyme developed by Halozyme is a truncated deletion variant that lacks such amino acids in the carboxy terminus responsible for the lipid attachment. This gives rise to a soluble, neutral pH-active enzyme similar to the protein found in bovine testes preparations. The rHuPH20 protein is synthesized with a 35 amino acid signal peptide that is removed from the N-terminus during the process of secretion. The mature rHuPH20 protein contains an authentic N-terminal amino acid sequence orthologous to that found in some bovine hyaluronidase preparations.

The PH20 hyaluronidases, including the animal derived PH20 and recombinant human rHuPH20, depolymerize hyaluronan by the hydrolysis of the β-1,4 linkage between the $C_1$ position of N-acetyl glucosamine and the $C_4$ position of glucuronic acid. The tetrasaccharide is the smallest digestion product (Weissmann, B., "The transglycosylative action of testicular hyaluronidase", J. Biol. Chem., 1955; 216: 783-94). This N-acetyl glucosamine/glucuronic acid structure is not found in N-linked glycans of recombinant biological products and therefore rHuPH20 will not affect the glycosylation of antibodies it is formulated with, such as e.g. pertuzumab or pertuzumab and trastuzumab. The rHuPH20 enzyme itself possesses six N-linked glycans per molecule with core structures similar to that found in monoclonal antibodies. As anticipated, these N-linked structures do not change over time, confirming the lack of enzymatic activity of rHuPH20 on these N-linked glycan structures. The short half-life of rHuPH20 and the constant synthesis of hyaluronan lead to a short and local action of the enzyme on tissues.

The hyaluronidase enzyme present in the subcutaneous formulation in accordance with the present invention can be prepared by using recombinant DNA technology. In this way it is ensured that the same protein (identical amino acid sequence) is obtained all the time and that an allergic reaction, e.g. caused by contaminating proteins co-purified during extraction from a tissue, is avoided. The hyaluronidase enzyme used in the formulation as exemplified herein is a human enzyme, viz. rHuPH20.

The amino acid sequence of rHuPH20 (HYLENEX™) is well known and available under CAS Registry No. 75971-58-7. The approximate molecular weight is 61 kDa.

While the safety and efficacy of hyaluronidase products has been established, there are only two monoclonal antibodies (Herceptin® and MabThera®) that have been approved for subcutaneous delivery, using hyaluronidase containing formulations. There is no known hyaluronidase containing subcutaneous formulation comprising two antibodies in the same formulation (co-formulation of two antibodies).

The concentration of the hyaluronidase enzyme depends on the actual hyaluronidase enzyme used in the preparation of the formulation in accordance with the invention. An effective amount of the hyaluronidase enzyme can be readily determined by the person skilled in the art based on the disclosure further below.

The hyaluronidase enzyme should be provided in sufficient amount to result in an increase in the dispersion and absorption of the co-administered anti-HER2 antibody or antibodies, such as pertuzumab and/or trastuzumab. The minimal amount of the hyaluronidase enzyme is at least about 150 U/ml. More particularly the effective amount of the hyaluronidase enzyme is about 150 U/ml to about 16,000 U/ml, or about 600 U/ml to about 16,000 ml, or about 1,000 to 16,000 U/ml, where the latter corresponds to about 0.01 mg to 0.16 mg protein based on an assumed specific activity of 100,000 U/mg. Alternatively the concentration of the hyaluronidase enzyme is about 1,500 to 12,000 U/ml, or more particularly about 2,000 U/ml or about 12,000 U/ml. The amounts specified correspond to the amount of hyaluronidase enzyme initially added to the formulation. The hyaluronidase enzyme concentrations measured in the final formulation may vary within a certain range. The ratio (w/w) of the hyaluronidase enzyme to the anti-HER2 antibody or antibodies is generally in the range of 1:1,000 to 1:8,000, or in the range of 1:4,000 to 1:5,000 or about 1:6,000.

The hyaluronidase enzyme may be derived from animals, human samples or manufactured based on the recombinant DNA technology as described further below.

In some embodiments, the subcutaneous HER2 antibody formulations herein comprise recombinant human hyaluronidase (rHuPH20) at a concentration of about 600 U/mL to about 16,000 U/mL, or about 1,000 U/mL to about 16,000 U/mL, or about 1,000 to about 2,000 U/ml, or at a concentration of about 600 U/ml, or about 667 U/mL, or about 1,000 U/mL, or about 2,000 U/mL, preferable about 1,000 U/mL.

In some embodiments the highly concentrated, stable pertuzumab formulations of the present invention comprise a fixed dose of 600 mg or 1200 mg of pertuzumab and recombinant human hyaluronidase (rHuPH20) at a concentration of 1,000 U/mL.

As noted above the soluble hyaluronidase glycoprotein may be considered to be a further excipient in the anti-HER2 formulation. The soluble hyaluronidase glycoprotein may be added to the anti-HER2 formulation at the time of manufacturing the anti-HER2 formulation or may be added shortly before the injection. Alternatively the soluble hyaluronidase glycoprotein may be provided as a separate injection. In the latter case the soluble hyaluronidase glycoprotein may be provided in a separate vial either in lyophilized form which must be reconstituted with suitable diluents before the subcutaneous injection takes place, or may be provided as a liquid formulation by the manufacturer. The anti-HER2 formulation and the soluble hyaluronidase glycoprotein may be procured as separate entities or may also be provided as kits comprising both injection components and suitable instructions for their subcutaneous administration. Suitable instructions for the reconstitution and/or administration of one or both of the formulations may also be provided.

In addition to the hyaluronidase enzyme, such as rHuPH20, the subcutaneous formulations of the present invention comprise one or more additional excipients, such as one or more buffering agents, one or more stabilizers, and/or one or more surfactants.

The buffer used in the formulations in accordance with the present invention has a pH in the range from about 5.0 to about 7.0, or from about 5.0 to about 6.0, or from about 5.3 to about 5.8, or from about 5.5 to about 5.7.

For the subcutaneous (SC) pertuzumab formulations the pH of about 5.7 has been found most suitable. A preferred pH of a subcutaneous (SC) trastuzumab formulation is about 5.5.

Examples of buffering agents that will control the pH in this range include acetate, succinate, gluconate, histidine, citrate, glycylglycine and other organic acid buffers. The most suitable buffer in accordance with the present invention is a histidine buffer, such as, for example, histidine chloride, histidine acetate, histidine phosphate, histidine sulfate, preferably a histidine chloride buffer. A histidine chloride buffer can be prepared by titrating L-histidine (free base, solid) with diluted hydrochloric acid. In particular the histidine buffer or histidine chloride buffer is an L-histidine buffer at pH of 5.5±0.6, more particularly at a pH from about 5.3 to about 5.8, and most particularly has a pH of 5.5 or 5.7.

The stabilizer may, for example, be a saccharide or a combination of saccharides, including monosaccharides, disaccharides, trisaccharides, polysaccharides, sugar alcohols, reducing sugars, nonreducing sugars, etc. Examples of saccharides herein include glucose, sucrose, trehalose, lactose, fructose, maltose, dextran, glycerin, dextran, erythritol, glycerol, arabitol, sylitol, sorbitol, mannitol, mellibiose, melezitose, raffinose, mannotriose, stachyose, maltose, lactulose, maltulose, glucitol, maltitol, lactitol, and isomaltulose. A particularly suitable saccharide for use in the trastuzumab SC formulations is trehalose, and a particularly suitable saccharide for use in the pertuzumab SC formulations is sucrose.

The surfactant preferably is a nonionic surfactant. Examples of surfactants herein include polysorbate; poloxamer (e.g. poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl oleyl-taurate; and the MONAQUAT™ series (Mona Industries, Inc., Paterson, N.J.); polyethyl glycol, polypropyl glycol, and copolymers of ethylene and propylene glycol (e.g. Pluronics, PF68 etc); etc. Polysorbate 20 (PS20) and Polysorbate 80 (PS80), respectively are particularly suitable for use in the formulations described herein.

III. Selecting Patients for Therapy

Detection of HER2 expression or amplification can be used to select patients for treatment in accordance with the present invention. Several FDA-approved commercial assays are available to identify HER2-positive, HER2-expressing, HER2-overexpressing or HER2-amplified cancer patients. These methods include HERCEPTEST® (Dako) and PATHWAY® HER2 (immunohistochemistry (IHC) assays) and PathVysion® and HER2 FISH pharmDx™ (FISH assays). Users should refer to the package inserts of specific assay kits for information on the validation and performance of each assay.

For example, HER2 expression or overexpression may be analyzed by IHC, e.g. using the HERCEPTEST® (Dako). Paraffin embedded tissue sections from a tumor biopsy may be subjected to the IHC assay and accorded a HER2 protein staining intensity criteria as follows:

Score 0 no staining is observed or membrane staining is observed in less than 10% of tumor cells.

Score 1+ a faint/barely perceptible membrane staining is detected in more than 10% of the tumor cells. The cells are only stained in part of their membrane.

Score 2+ a weak to moderate complete membrane staining is observed in more than 10% of the tumor cells.

Score 3+ a moderate to strong complete membrane staining is observed in more than 10% of the tumor cells.

Those tumors with 0 or 1+ scores for HER2 overexpression assessment may be characterized as HER2-negative, whereas those tumors with 2+ or 3+ scores may be characterized as HER2-positive.

Tumors overexpressing HER2 may be rated by immunohistochemical scores corresponding to the number of copies of HER2 molecules expressed per cell, and can been determined biochemically:

0=0–10,000 copies/cell,
1+=at least about 200,000 copies/cell,
2+=at least about 500,000 copies/cell,
3+=at least about 2,000,000 copies/cell.

Overexpression of HER2 at the 3+ level, which leads to ligand-independent activation of the tyrosine kinase (Hudziak et al., *Proc. Natl. Acad. Sci. USA,* 84:7159-7163 (1987)), occurs in approximately 30% of breast cancers, and in these patients, relapse-free survival and overall survival are diminished (Slamon et al., *Science,* 244:707-712 (1989); Slamon et al., *Science,* 235:177-182 (1987)).

The presence of HER2 protein overexpression and gene amplification are highly correlated, therefore, alternatively, or additionally, the use of in situ hybridization (ISH), e.g. fluorescent in situ hybridization (FISH), assays to detect gene amplification may also be employed for selection of patients appropriate for treatment in accordance with the present invention. FISH assays such as the INFORM™ (sold by Ventana, Ariz.) or PathVysion® (Vysis, Ill.) may be carried out on formalin-fixed, paraffin-embedded tumor tissue to determine the extent (if any) of HER2 amplification in the tumor.

Most commonly, HER2-positive status is confirmed using archival paraffin-embedded tumor tissue, using any of the foregoing methods.

Preferably, HER2-positive patients having a 2+ or 3+ IHC score and/or who are FISH or ISH positive are selected for treatment in accordance with the present invention. Patients with 3+ IHC score and FISH/ISH positivity are particularly suitable for treatment in accordance with the present invention.

HER2 mutations associated with responsiveness to HER2-directed therapy have also been identified. Such mutations include, without limitation, insertions in exon 20 of HER2, deletions around amino acid residues 755-759 of HER2, any of the mutations G309A, G309E, S310F, D769H, D769Y, V777L, P780-Y781insGSP, V842I, R896C (Bose et al., Cancer Discov 2013; 3:1-14), as well as previously reported identical non-synonymous putative activating mutations (or indels) in COSMIC database found in two or more unique specimens.

See also U.S. Pat. No. 7,981,418 for alternative assays for screening patients for therapy with pertuzumab, and the Examples.

IV. Pharmaceutical Formulations

Therapeutic formulations of the HER2 antibodies used in accordance with the present invention are prepared for storage by mixing an antibody having the desired degree of purity with optional pharmaceutically acceptable carriers, excipients or stabilizers (*Remington's Pharmaceutical Sciences* 16$^{th}$ edition, Osol, A. Ed. (1980)), generally in the form of lyophilized formulations or aqueous solutions. Antibody crystals are also contemplated (see US Pat Appln 2002/0136719). Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Lyophilized antibody formulations are described in WO 97/04801, expressly incorporated herein by reference.

Lyophilized antibody formulations are described in U.S. Pat. Nos. 6,267,958, 6,685,940 and 6,821,515, expressly incorporated herein by reference. The preferred HERCEPTIN® (trastuzumab) formulation is a sterile, white to pale yellow preservative-free lyophilized powder for intravenous (IV) administration, comprising 440 mg trastuzumab, 400 mg alpha α,α-trehalose dehydrate, 9.9 mg L-histidine-HCl, 6.4 mg L-histidine, and 1.8 mg polysorbate 20, USP. Reconstitution of 20 mL of bacteriostatic water for injection (BWFI), containing 1.1% benzyl alcohol as a preservative, yields a multi-dose solution containing 21 mg/mL trastuzumab, at pH of approximately 6.0. For further details, see the trastuzumab prescribing information.

The preferred pertuzumab formulation for therapeutic use comprises 30 mg/mL pertuzumab in 20 mM histidine acetate, 120 mM sucrose, 0.02% polysorbate 20, at pH 6.0. An alternate pertuzumab formulation comprises 25 mg/mL pertuzumab, 10 mM histidine-HCl buffer, 240 mM sucrose, 0.02% polysorbate 20, pH 6.0.

The formulation of the placebo used in the clinical trials described in the Examples is equivalent to pertuzumab, without the active agent.

The formulation herein may also contain more than one active compound as necessary for the particular indication being treated, preferably those with complementary activities that do not adversely affect each other. Various drugs which can be combined with the HER dimerization inhibitor are described in the Method Section below. Such molecules are suitably present in combination in amounts that are effective for the purpose intended.

The formulations to be used for in vivo administration must be sterile. This is readily accomplished by filtration through sterile filtration membranes.

Exemplary specific formulations suitable for use in the methods of the present invention are as follows:

Pertuzumab IV: pertuzumab 420 mg/14 ml concentrate for i.v. infusion is a sterile, clear to slightly opalescent, colorless to pale brown liquid supplied in 20 ml single-use glass vials with 20 mm stoppers. Each single-use vial contains 420 mg of pertuzumab at a concentration of 30 mg/mL in 20 mM L-histidine acetate (pH 6.0), 120 mM sucrose and 0.02% polysorbate 20.

Pertuzumab SC with rHuPH20: pertuzumab 600 mg/5 ml with rHuPH20 solution for s.c. injection is a sterile, preservative-free, colorless to slightly brownish liquid supplied in 10 ml single-use vials with 20 mm stoppers. Vials are filled to enable delivery and transfer of 5.0 ml of the study drug filled with about 5.4 ml drug product). Each vial is composed of a formulations containing 120 mg/mL RO4368451 in L-histidine acetate buffer containing excipients sucrose, polysorbate 20, methionine, and rHuPH20 (2000 U/mL) at pH 5.7.

A specific pertuzumab SC formulation with rHuPH20 has the following ingredients:
120 mg/mL pertuzumab
240 mM Sucrose
0.02% Polysorbate 20
10 mM Methionine
2000 U/mL rhuPH20
20 mM Histidine/Acetate
pH 5.7

Pertuzumab SC without rHuPH20: pertuzumab 500 mg/5 ml solution for s.c. injection is a sterile, preservative-free, colorless to slightly brownish liquid supplied in 10 ml single-use glass vials with 20 mm stoppers. Vials are filled to enable delivery and transfer of 5.0 ml of study drug. Each vial is composed of a formulation containing 120 mg/mL pertuzumab in L-histidine acetate buffer containing excipients sucrose, polysorbate 20, and methionine at pH 5.7.

Trastuzumab SC: trastuzumab for subcutaneous administration typically contains the following ingredients: recombinant human hyaluronidase (rHuPH20); L-histidine; L-histidine hydrochloride monohydrate; α,α-trehalose dehydrate; L-methionine; Polysorbate 20; Water for injections, trastuzumab 600 mg/5 ml. The trastuzumab solution for s.c. injection is a sterile, preservative-free, colorless to slightly brownish liquid supplied in 6 ml single-use glass vials with 20 mm stoppers. Each vial is composed of a formulation containing 120 mg/mL of trastuzumab in L-Histidine-HCl buffer containing excipients trehalose, polysorbate 20, methionine, and rHuPH20 (2000 U/mL) at pH 5.5.

A specific trastuzumab SC formulation has the following ingredients: 120 mg/mL trastuzumab
210 mM Trehalose
0.04% Polysorbate 20
10 mM Methionine
2,000 U/mL rHuPH20
20 mM Histidine-HCl
pH 5.5

A specific pertuzumab-trastuzumab SC fixed-dose combination (FDC) Loading dosage form has the following composition: trastuzumab 600 mg and pertuzumab 1,200 mg in 15 ml solution for s.c. injection is a sterile, preservative-free, colorless to slightly brownish liquid supplied in 20 ml single-use glass vials with 20 mm stoppers. Each vial is composed of a formulation containing 40 mg/mL of trastuzumab and 80 mg/ml of pertuzumab in L-Histidine-HCl buffer containing excipients trehalose, sucrose, polysorbate 20, methionine, and rHuPH20 (1,000 U/mL) at pH 5.5. A specific pertuzumab-trastuzumab SC fixed-dose combination (FDC) Maintenance dosage form has the following composition: trastuzumab 600 mg and pertuzumab 600 mg in 10 ml solution for s.c. injection is a sterile, preservative-free, colorless to slightly brownish liquid supplied in 15 ml single-use glass vials with 20 mm stoppers. Each vial is composed of a formulation containing 60 mg/mL of trastuzumab and 60 mg/ml of pertuzumab in L-Histidine-HCl buffer containing excipients trehalose, sucrose, polysorbate 20, methionine, and rHuPH20 (1,000 U/mL) at pH 5.5.

V. Treatment Methods

For intravenous administration, pertuzumab and trastuzumab are administered according to applicable prescribing information.

Pertuzumab is typically administered every three weeks by intravenous infusion, starting with a first 840 mg infusion administered over 60 minutes, followed by a second and any subsequent intravenous infusions of 420 mg administered over 30 to 60 minutes. Further details of suitable administration schedules are given in the trastuzumab Prescribing Information.

Trastuzumab is typically administered every three weeks by intravenous infusion starting with a first 8 mg/kg loading dose over 90 minutes, followed by a second and any subsequent intravenous infusions 6 mg/kg maintenance doses administered over 30 to 60 minutes. Further details of suitable administration schedules are given in the trastuzumab Prescribing Information.

Pertuzumab and trastuzumab can be administered during the same visit, in either order.

According to the present invention, pertuzumab or pertuzumab+trastuzumab are administered subcutaneously.

Pertuzumab SC is typically administered every three weeks as subcutaneous injection, starting with a fixed loading dose of about 1200 mg, followed by a second and any subsequent fixed maintenance doses of about 600 mg as hereinabove disclosed and as described in the Examples. The injection site should be alternated between the left and the right thigh. New injections should be given at least 2.5 cm from the old site on healthy skin and not into areas where the skin is red, bruised, tender or hard.

Trastuzumab SC is typically administered as subcutaneous injections at a 600 mg dose over 2-5 minutes every three weeks. The injection site should be alternated between the left and the right thigh. New injections should be given at least 2.5 cm from the old site on healthy skin and not into areas where the skin is red, bruised, tender or hard.

Pertuzumab/trastuzumab SC co-formulations are administered in a similar manner

For the co-mix subcutaneous administration of pertuzumab and trastuzumab, it is necessary to compound the final mixture in syringes using a syringe connector. The subcutaneous injection is finally administered using a disposable plastic syringe and stainless steel needle.

VI. Articles of Manufacture

In another embodiment of the invention, an article of manufacture containing materials useful for the treatment of cancer. The article of manufacture comprises a vial with a fixed dose of the pertuzumab for subcutaneous administration, wherein the fixed dose is approximately 600 mg or approximately 1200 of pertuzumab. The article of manufacture preferably further comprises a package insert. The package insert may provide instructions to administer the fixed dose to a patient with HER2-expressing, e.g. HER2-positive, HER2-amplified, or HER2-mutated cancer subcutaneously, alone or in combination with subcutaneous administration of trastuzumab, where administration in combination includes, without limitation, co-administration, co-mixed administration and administration of a co-formulation, as hereinabove defined and described and as described in the Examples. In certain embodiments, the cancer is breast cancer, ovarian cancer, peritoneal cancer, fallopian tube cancer, lung cancer, prostate cancer, colorectal cancer, biliary cancer and bladder cancer. In other embodiments, the cancer is breast cancer, peritoneal cancer, fallopian tube cancer, lung cancer, colorectal cancer, biliary cancer and bladder cancer. In a particular embodiment, the cancer is breast cancer, such as early breast cancer or metastatic breast cancer.

In one embodiment, the article of manufacture is a single-use glass vial equipped with a stopper, which contains the formulation to be administered.

Another form of an article of manufacture is a syringe, containing the formulation to be administered, which may be attached to a stainless steel hypodermic needle for subcutaneous administration.

In one embodiment, the article of manufacture comprises two vials, wherein a first vial contains a fixed dose of approximately 1200 mg of pertuzumab, and a second vial contains a fixed dose of approximately 600 mg of pertuzumab.

In another embodiment, the article of manufacture of comprises two vials, wherein a first vial contains a fixed dose of approximately 600 mg of pertuzumab, and a second vial contains a fixed dose of approximately 600 mg of trastuzumab.

In another embodiment, the article of manufacture comprises a single-dose vial containing about 600 mg of pertuzumab.

IV. Deposit of Biological Materials

The following hybridoma cell lines have been deposited with the American Type Culture Collection, 10801 University Boulevard, Manassas, Va. 20110-2209, USA (ATCC):

| Antibody Designation | ATCC No. | Deposit Date |
|---|---|---|
| 4D5 | ATCC CRL 10463 | May 24, 1990 |
| 2C4 | ATCC HB-12697 | Apr. 8, 1999 |

TABLE 1

TABLE OF SEQUENCES

| Description | SEQ ID NO | FIG. |
|---|---|---|
| HER2 domain I | 1 | 1 |
| HER2 domain II | 2 | 1 |
| HER2 domain III | 3 | 1 |
| HER2 domain IV | 4 | 1 |
| 2C4 variable light | 5 | 2A |
| 2C4 variable heavy | 6 | 2B |
| 574/pertuzumab variable light | 7 | 2A |
| 574/pertuzumab variable heavy | 8 | 2B |

TABLE 1-continued

TABLE OF SEQUENCES

| Description | SEQ ID NO | FIG. |
|---|---|---|
| human $V_L$ consensus framework | 9 | 2A |
| Human $V_H$ consensus framework | 10 | 2B |
| pertuzumab light chain | 11 | 3A |
| pertuzumab heavy chain | 12 | 3B |
| trastuzumab light chain | 13 | 4A |
| trastuzumab heavy chain | 14 | 4B |
| Variant pertuzumab light chain | 15 | 5A |
| Variant pertuzumab heavy chain | 16 | 5B |
| GFTFTDYTMX | 17 | |
| DVNPNSGGSIYNQRFKG | 18 | |
| NLGPSFYFDY | 19 | |
| KASQDVSIGVA | 20 | |
| SASYX$^1$X$^2$X$^3$ | 21 | |
| QQYYIYPYT | 22 | |

Further details of the invention are illustrated by the following non-limiting Examples. The disclosures of all citations in the specification are expressly incorporated herein by reference.

TABLE 2

LIST OF ABBREVIATIONS AND DEFINITIONs OF TERMS

| Abbreviation | Definition |
|---|---|
| ALP | alkaline phosphatase |
| ALT | alanine aminotransferase |
| ARDS | acute respiratory distress syndrome |
| ARR | administration-related reaction |
| AST | aspartate aminotransferase |
| ATA | anti-therapeutic antibody |
| AUC | area under the serum concentration-time curve |
| AUC$_{0-21\ day}$ | area under the serum concentration-time curve AUC from start of study treatment to Day 21 |
| AUC$_{0-inf}$ | area under the concentration-time curve from start of study treatment 0 to infinity |
| BMI | body mass index |
| BP | blood pressure |
| CHF | congestive heart failure |
| CL/F | mean apparent clearance |
| $C_{max}$ | maximum serum concentration |
| $C_{trough}$ | trough concentration |
| CTCAE | Common Terminology Criteria for Adverse Events |
| EBC | early breast cancer |
| EC | Ethics Committee |
| ECG | electrocardiogram |
| ECHO | echocardiography |
| eCRF | electronic Case Report Form |
| EDC | electronic data capture |
| EGFR | epidermal growth factor receptor |
| FDC | fixed-dose combination |
| FEC | fluorouracil, epirubicin, and cyclophosphamide |
| GLP | Good Laboratory Practice |
| HBcAb | total hepatitis B core antibody |
| HBsAg | hepatitis B surface antigen |
| HCG | human chorionic gonadotropin |
| HCV | hepatitis C virus |
| HER2 | human epidermal growth factor receptor 2 |
| HIV | human immunodeficiency virus |
| HMV | healthy male volunteer |

TABLE 2-continued

LIST OF ABBREVIATIONS AND DEFINITIONs OF TERMS

| Abbreviation | Definition |
|---|---|
| HR | heart rate |
| IB | Investigator's Brochure |
| ICH | International Conference on Harmonisation |
| Ig | immunoglobulin |
| IMP | investigational medicinal product |
| IND | Investigational New Drug Application |
| INN | International Non-Proprietary Name |
| IRB | Institutional Review Board |
| IRR | infusion-related reaction |
| IV | intravenous |
| IUD | intrauterine device |
| LPLV | last patient, last visit |
| LVEF | left ventricular ejection fraction |
| mAb | monoclonal antibody |
| MBC | metastatic breast cancer |
| MedDRA | Medical Dictionary for Regulatory Activities |
| MUGA | multi-gated acquisition (scan) |
| NCI | National Cancer Institute |
| NYHA | New York Heart Association |
| ORR | overall response rate |
| PK | pharmacokinetic(s) |
| popPK | population pharmacokinetics |
| Q3W | every 3 weeks |
| QTc | QT interval corrected for rate |
| QTcF | QT interval corrected using Fridericia's formula |
| RBC | red blood cell |
| rHuPH20 | recombinant human hyaluronidase |
| SC | subcutaneous |
| SD | standard deviation |
| SI | International System of Units |
| SID | single-use injection device |
| SYR | syringe |
| TBD | to be determined |
| $t_{max}$ | time of maximum serum concentration |
| $t_{1/2}$ | elimination half-life |
| TK | Toxicokinetic |
| ULN | upper limit of normal |
| WBC | white blood cell |

EXAMPLE 1

Phase I Pertuzumab Subcutaneous Dose-Finding Study in Combination with Trastuzumab This is a Phase I, open-label, two-part multicenter clinical pertuzumab subcutaneous dose-finding study in combination with trastuzumab in healthy male volunteers and female patients with early breast cancer.

The study is designed the safety and PK of pertuzumab SC for Q3W treatment by applying a PK-based approach to compare an SC formulation to the approved IV formulation. In this dose-finding study, it is intended to identify the SC dose that is comparable to IV with respect to serum concentrations. pertuzumab Q3W SC serum $C_{trough}$ concentrations are unknown.

Different types of pertuzumab SC injections will be assessed in the study:
  Separate administration of pertuzumab SC with or without trastuzumab SC as separate injections (co-administration)
  Simultaneous administration of pertuzumab SC and trastuzumab SC as single injection (co-mixed)
  Administration of pertuzumab and trastuzumab SC as a single injection (co-mixed)

Initially, in Part 1, Healthy Mail Volunteers (HMVs) will receive a single dose of IV or SC pertuzumab (with or without trastuzumab SC) to select the SC dose(s) of pertuzumab expected to result in serum concentrations comparable to IV pertuzumab, both when given as co-administration or co-mixed injection. The pertuzumab SC dose(s) will then be confirmed in patients with EBC.

Based on PK data in Part 1 (healthy volunteer cohorts), the pertuzumab popPK model will be used to identify the target dose(s) for Part 2. (See, Garg et al., *Cancer Chemother Pharmacol* (2014) 74:819-829.)

Upon selection of the target dose and on the basis of information about the feasibility of an FDC, patients with early breast cancer (EBC) who have completed their standard treatment will be enrolled in Part 2 to receive pertuzumab SC at the dose(s) identifies in Part 1. This identified dose of pertuzumab will be either co-administered with trastuzumab SC, co-mixed with trastuzumab SC, or co-formulated with trastuzumab SC in a fixed-dose combination (FDC). Part 2 will include pertuzumab SC dose confirmation as well as a comparison of PK from co-mixed and FDC.

In this study in which two monoclonal antibodies (mAbs) will be administered at a volume of up to approximately 15 mL, the concentration of rHuPH20 will also be evaluated. Previously, 2000 U/mL of the absorption enhancer has been used with trastuzumab SC and Rituximab SC, however, these are single antibodies and at volumes less than the pertuzumab/trastuzumab combination studied here.

In order to determine if less rHuPH20 would lead to adequate mAb absorption, the study has been designed to test an enzyme concentration of 2000 U/mL when both antibodies are given (15 mL volume) and an enzyme concentration of 667 U/mL (using pertuzumab that does not contain rHuPH20) when both antibodies are given (15 mL volume). If the PK parameters are approximately equivalent, the reduced amount of rHuPH20 may be potentially used in the development of the FDC co-formulated product.

Objectives and Endpoints
Primary Objectives
Part 1 (Dose Finding)
The primary objectives for Part 1 of this study are as follows:
 To select the subcutaneous (SC) loading and maintenance dose of pertuzumab that results in comparable exposure to intravenous (IV) pertuzumab when pertuzumab SC is given as a single-agent injections (for eventual use in co-administration with trastuzumab SC).
 To select the SC loading and maintenance dose of pertuzumab that results in comparable exposure to IV pertuzumab when pertuzumab SC is given mixed with trastuzumab SC as a single injection (co-mixed).
 To assess whether additional rHuPH20 is needed when pertuzumab SC and trastuzumab SC are co-mixed SC.
Part 2 (Dose Confirmation)
The primary objectives for Part 2 of this study are as follows:
 To confirm the maintenance dose of pertuzumab SC when given as a single-agent injection as part of co-administration with trastuzumab SC or
 To confirm the maintenance dose of pertuzumab SC when given mixed with trastuzumab SC in a single injection (co-mixed) or co-formulated with trastuzumab SC in a ready-to-use single injection (fixed-dose combination (FDC)).
Secondary Objectives
The secondary objectives of this study are as follows:
 To assess the safety and tolerability of pertuzumab SC give alone or in combination with trastuzumab SC (co-mixed or FDC) in healthy male volunteers (HMV) and female patients with early breast cancer (EBC) who have completed standard breast cancer therapy, on the basis of the following endpoints:
 Incidence, nature and severity of adverse events graded according to the National
 Cancer Institute Common Terminology Criteria for Adverse Events (NCI CTCAE) v4.03;
 Changes in vital sign, left ventricular ejection fraction (LVEF), and electrocardiogram (ECG) parameters;
 Changes in clinical laboratory results;
 Incidence of anti-therapeutic antibody (ATA) response.

Study Design
Description of the Study
Overview of Study Design
This is an open-label, two-part, multi-center study of pertuzumab SC.

Part 1 of the study is dose finding, in which the loading and maintenance dose of pertuzumab SC will be determined in HMVs. Two types of pertuzumab SC injections will be assessed: pertuzumab given as a single-agent injection (for eventual use in co-administration with trastuzumab SC single-agent injection) and pertuzumab SC co-mixed with trastuzumab SC in a single injection.

Part 2 of the study will confirm the pertuzumab SC dose(s) in patients with EBC who have completed standard breast cancer therapy. The dose of pertuzumab SC in Part 2 will be co-administered with trastuzumab SC, co-mixed with trastuzumab SC, or co-formulated with trastuzumab SC as an FDC. Part 2 will include pertuzumab SC dose confirmation as well as a comparison of PK from co-mixed and FDC before a Phase III study.

Figure 6:
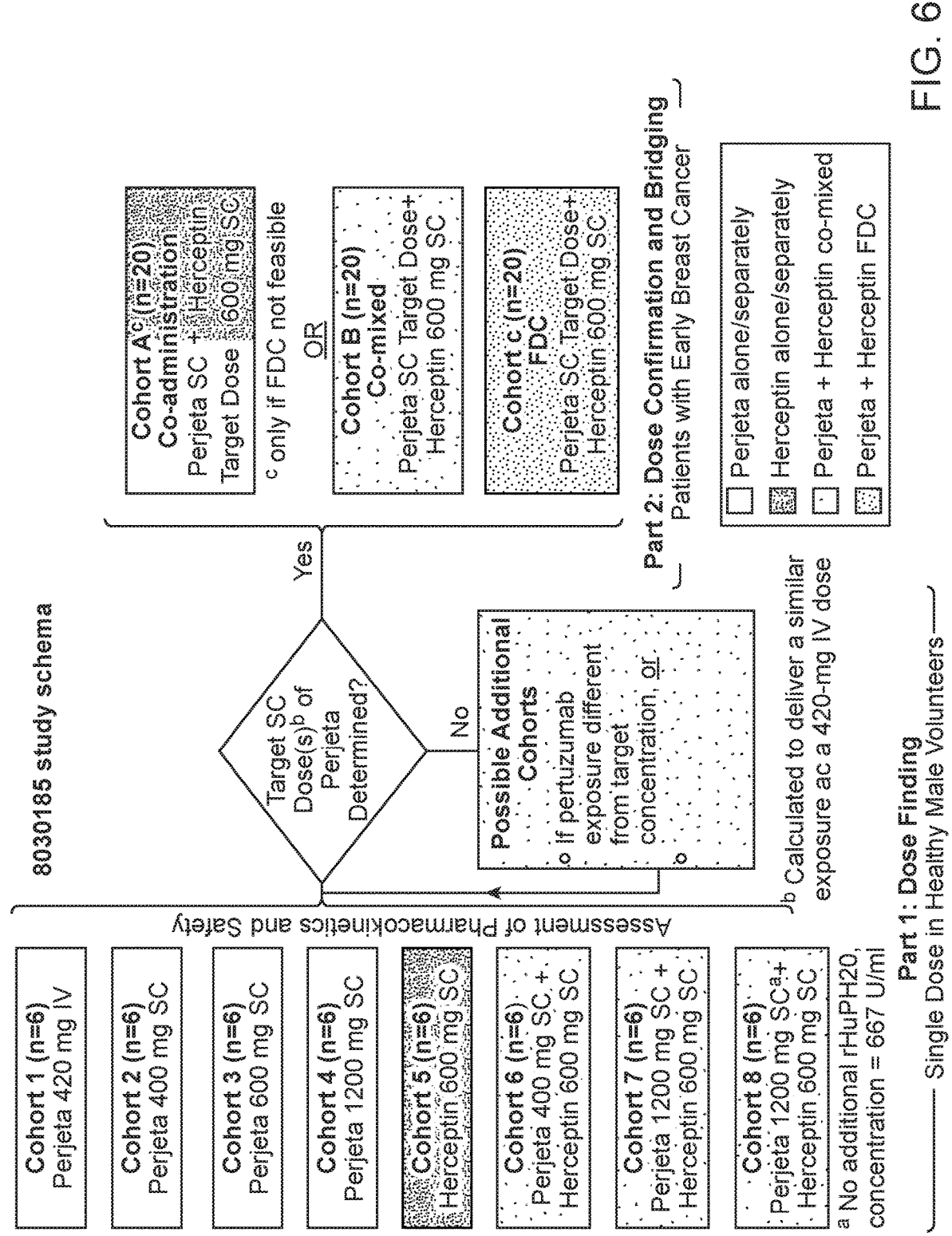
FIG. 6 shows the study schema of the dose finding study for subcutaneous administration of pertuzumab alone and in combination with trastuzumab.

See FIG. 6 for the study schema. Safety will be monitored and blood samples for PK assessment will be drawn according to the schedule of assessments.

Part 1 (Dose Finding)
HMVs were enrolled into Cohorts 1 to 8 (6 subjects per cohort). Each subject received a single injection. Cohorts 2-4 assessed different pertuzumab SC doses. Cohorts 5 to 8 assessed doses of pertuzumab+trastuzumab co-mixed. The doses evaluated within each cohort are as follows:
 Cohort 1: 420 mg pertuzumab IV (control)
 Cohort 2: 400 mg pertuzumab SC
 Cohort 3: 600 mg pertuzumab SC
 Cohort 4: 1200 mg pertuzumab SC
 Cohort 5: 600 mg trastuzumab SC (control)
 Cohort 6: 400 mg pertuzumab SC plus 600 mg trastuzumab SC (co-mixed)
 Cohort 7: 1200 mg pertuzumab SC plus 600 mg trastuzumab SC (co-mixed)
 Cohort 8: 1200 mg pertuzumab SC (without rHuPH20) plus 600 mg trastuzumab SC (co-mixed)

The different pertuzumab doses were administered by adjusting the dosing volume. The concentration of pertuzumab and trastuzumab was 120 mg/mL and rHuPH20 was 2,000 U/mL in the SC dosing solutions.

Cohorts 6 and 7 received pertuzumab SC and trastuzumab SC both containing rhuPH20 in a concentration of 2,000 U/mL, while HMVs in Cohort 8 were given pertuzumab SC containing no rHuPH20, co-mixed with trastuzumab SC containing rhuPH20 in a concentration of 2,000 U/mL, therefore the overall rhuPH20 concentration received by Cohort 8 was approximately 667 U/mL. Cohort 8 was planned to assess the impact of a lower concentration of rHuPH20 on the PK of pertuzumab and trastuzumab when administered in a co-mixed injection.

Time to Observe
To ensure safety during the trial, the first healthy volunteer in Cohort 2 was closely monitored for safety and tolerability after treatment with pertuzumab SC and until the end of Day 3. The 3-day monitoring was completed prior to expanding Cohort 2 and prior to commencing dosing in Cohort 3 or 4.

If the pertuzumab SC dose was deemed safe and tolerated in the first healthy volunteer in Cohort 2, subsequent healthy volunteers were treated in parallel in Cohorts 2, 3, and 4 without the addition of the 3-day time period to observe.

Similarly, 3 healthy volunteers in Cohort 6 were treated with pertuzumab and trastuzumab SC and closely monitored for safety and tolerability for 3 days post-dose, prior to expanding Cohort 6 and prior to commencing dosing in Cohort 7 or 8.

If the pertuzumab and trastuzumab SC dose was deemed safe and tolerated in the first 3 healthy volunteers in Cohort 6, subsequent healthy volunteers will be treated in parallel in Cohort 6 without the addition of the 3-day time period to observe.

Cohorts 7 and 8 were opened at the same time. Three HMVs were treated with pertuzumab and trastuzumab SC, and closely monitored for safety and tolerability for 3 days post-dose, prior to expanding the respective cohorts.

If the pertuzumab and trastuzumab SC dose was deemed safe and tolerated in the first 3 healthy volunteers in Cohorts 7 and 8, subsequent healthy volunteers will be treated in parallel in those cohorts without the addition of the 3-day time period to observe.

Healthy volunteers in Cohorts 1 and 5 can be dosed in parallel and may be enrolled prior to the first healthy volunteer in Cohort 2.

Dose Selection for Part 2

The selection of the pertuzumab SC doses in Part 1 (Cohorts 2, 3, and 4) is based on the pertuzumab IV population pharmacokinetics (popPK) model with the values of the trastuzumab SC PK parameters incorporated. Once the sufficient amount of data in Part 1 allows the estimation of fixed PK parameters (i.e., $C_{trough}$, AUC0-inf, maximum serum concentration $[C_{max}]$, time of maximum serum concentration $[T_{max}]$), the pertuzumab SC (maintenance) dose(s) will be selected for Part 2. This SC dose will be calculated to deliver a similar pertuzumab exposure to that of IV pertuzumab at 420 mg. Equally, based on PK parameters, one pertuzumab SC (loading) dose will be calculated to deliver a similar pertuzumab exposure to that of IV pertuzumab at 840 mg. The pertuzumab IV popPK model will be updated with pertuzumab SC parameters using the Part 1 data and will be used to correctly identify the SC maintenance and loading doses.

The trastuzumab SC 600-mg dose was determined in the Phase Ib dose-finding study BP22023 and confirmed in the Phase III HannaH study.

Additional dose-finding cohorts may be opened if doses from planned cohorts result in pertuzumab exposure different from the target concentration or if the variability in pharmacokinetics is too high to determine a dose for Part 2 of the study.

Using Part 1 data, a pertuzumab SC dose was calculated to deliver a similar pertuzumab exposure to that of pertuzumab IV at 420 mg (maintenance dose) and 840 mg (loading doses). The selected rHuPH20 concentration for the co-mixed administration of pertuzumab and trastuzumab in Cohort B was based on comparbility of safety and pertuzumab exposure in Cohorts 7 and 8.

Part 2 (Dose Confirmation)

Women with EBC who have completed standard (neo) adjuvant breast cancer therapy were enrolled in Part 2.

If the feasibility of an FDC product is confirmed, Cohorts B and C only (not Cohort A; co-administration) may be enrolled in Part 2. This would allow confirmation of the Part 1 dose and show comparability between a co-mixed injection and an FDC product. If there is a PK interaction between pertuzumab and trastuzumab when co-mixed or if the development of the FDC is not feasible, only Cohort A may be enrolled in Part 2, which would allow confirmation of the Part 1 dose. This study design will allow for the selection of a pertuzumab SC dose and formulation option for the Phase III study while enrolling the fewest number of patients. The overall schema for Part 2 shall therefore be Cohort A only or Cohort B and Cohort C (see 185H FIG. 2). Each cohort will enroll 20 patients and each patient will receive one dose of pertuzumab and trastuzumab.

Each Cohort enrolled 20 patients and each patient received one dose of pertuzumab and trastuzumab.

Cohort A: pertuzumab SC (dose determined in Part 1) with 600 mg trastuzumab SC; each agent administered separately (co-administration) or Cohort B: pertuzumab SC (dose determined in Part 1) with 600 mg trastuzumab SC; both agents administered in one injection (co-mixed) and Cohort C: pertuzumab SC (dose determined in Part 1) with 600 mg trastuzumab SC; both agents formulated together and administered in one injection (FDC)

The highest planned pertuzumab SC dose administered in Part 1 and Part 2 will not exceed 1200 mg.

Note: The pertuzumab and trastuzumab doses will be modified by adjusting the dosing volume. The concentration of pertuzumab and trastuzumab is 120 mg/mL and of rHuPH20 (when present) is 2000 U/mL in the SC dosing solutions.

Figure 7:
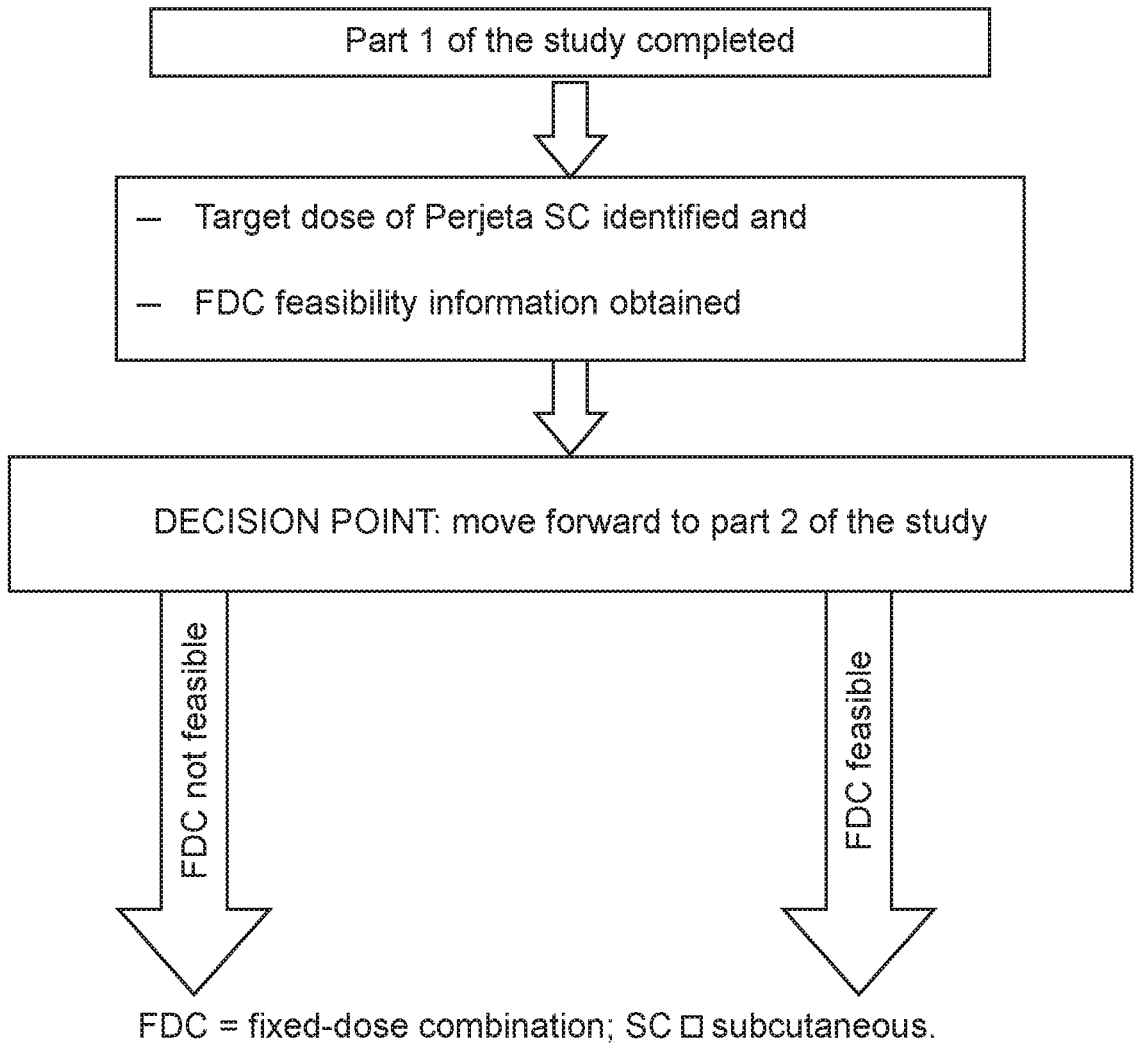
FIG. 7 Decision Diagram.

The decision diagram is shown in FIG. 7.

If there was a PK interaction between pertuzumab and trastuzumab wen administered in a co-mixed injection, or if the development of the FDC was not feasible, only Cohort A (co-administration) was to be enrolled in Part 2. This study design allowed for the selection of a pertuzumab SC dose and formulation option for further evaluation in the Phase III study while enrolling the fewest number of patients. The overall schema for Part 2 was therefore Cohort A only or Cohort B and Cohort C.

Criteria for Continuing or Stooping Dosing

Safety, tolerability, and PK data will be assessed continuously and prior to expanding cohorts or (if needed) adding cohorts. The starting doses will be pertuzumab 420 mg IV and 400, 600, and 1200 mg SC.

To allow informed decisions regarding dosing healthy volunteers in SC cohorts, the relevant safety and tolerability data of certain subjects will be reviewed after 3 days before dosing the next subject in the cohort or opening other cohorts.

The decision to continue dosing will be made jointly by the investigator and the Roche Medical Monitor and any other person that the investigator or Medical Monitor considers necessary to assist with this decision.

The dose will not be further administered in any other healthy volunteer or EBC if the tolerability or safety in a preceding healthy volunteer or EBC is not acceptable as judged by the Investigator and the Medical Monitor. Dosing should not be further administered in any other healthy volunteer or EBC if any of the events listed below occurs, unless it is obvious that the occurrence is not related to the administration of the treatment:

Severe drug-related adverse event

Hypersensitivity reactions according to the NCI CTCAE (Grades 3 to 5)

An LVEF drop of >10% points or to <50% (for HMV)

An LVEF drop of >10% points and to <50% (for EBC)

A repeat assessment must be carried out within 3 weeks of the first documented drop and the case must be reviewed by a Cardiologist. New York Heart Association (NYHA) class II congestive heart failure (CHF) or greater must be confirmed by a cardiologist.

It should be made clear that these are guidelines only and the Investigator together with the Medical Monitor can make an exception. However, when such an exception is made, the reasons for it should be clearly documented on the electronic Case Report Form (eCRF).

End and Length of the Study

The end of this study is defined as the date when the last patient, last visit (LPLV) occurs. LPLV is expected to occur 7 months after the last patient is enrolled. The total length of the study, from screening of the first patient to the end of the study, is expected to be approximately 16 to 24 months. There will be a maximum of 34 weeks for healthy volunteers/patients from screening to follow-up (up to 4 weeks for screening period and 30 weeks for the study conduct and follow-up).

For each study participant (HMV and EBC patients), the screening period was up to 4 weeks and the follow-up was performed approximately 7 months after the study drug administration.

Materials and Methods

Study Population

Part 1 Inclusion Criteria

HMVs must meet the following criteria for study entry:

Signed Informed Consent Form

Healthy male subjects, ages 18 to 45 years inclusive

Able to comply with the study protocol, in the investigator's judgment

LVEF≥55% measured by echocardiography (ECHO) or multi-gated acquisition (MUGA) scan A body mass index (BMI) between 18 and 32 kg/m² inclusive Agreement to remain abstinent (refrain from heterosexual intercourse) or use contraceptive measures and agreement to refrain from donating sperm, as defined below:

With female partners of childbearing potential, men must remain abstinent or use a condom plus an additional contraceptive method that together result in a failure rate of <1% per year during the treatment period and for at least 7 months after the administration of pertuzumab and/or trastuzumab. The reliability of sexual abstinence should be evaluated in relation to the duration of the clinical trial and the preferred and usual lifestyle of the patient. Periodic abstinence (e.g., calendar, ovulation, symptothermal, or postovulation methods) and withdrawal are not acceptable methods of contraception.

Men must refrain from donating sperm during this same period.

With pregnant female partners, men must remain abstinent or use a condom during the treatment period and for at least 7 months after the administration of pertuzumab and/or trastuzumab to avoid exposing the embryo.

No contraindications from detailed medical and surgical history and physical

Intact normal skin without potentially obscuring tattoos, pigmentation, or lesions in the area for intended injection in the thighs.

Part 1 Exclusion Criteria

HMVs who meet any of the following criteria will be excluded from study entry:

Positive urine test for drugs of abuse as per local standard

Positive result on hepatitis B virus (HBV), hepatitis C virus (HCV), or human immunodeficiency virus (HIV) 1 or 2 test History of exposure to HBV, HCV, or HIV Active viral hepatitis infection (hepatitis B or C) or HIV infection Systolic blood pressure (BP)≥140 mmHg or <90 mmHg, or diastolic BP>0 mmHg or <50 mmHg Use of prohibited medications or herbal remedies within 10 days or 5 times the elimination half-life (whichever is longer) prior to study drug administration Clinically significant abnormalities in laboratory test results (including hepatic and renal panels, complete blood count, chemistry panel, and urinalysis)

Clinically relevant ECG abnormalities on screening or baseline ECG, including but not limited to the following:

QTc interval (QTcB>450 msec)

Notable resting tachycardia (HR>100 bpm)

Difference between highest and lowest of any baseline QTc at a specific timepoint>30 msec Measurement of QT interval imprecise (e.g., flat T waves, arrhythmias, etc.)

Evidence of atrial fibrillation, atrial flutter, right or left bundle branch block, Wolf-Parkinson-White syndrome, or cardiac pacemaker Any other significant abnormality History of any cardiac condition or LVEF<55%

Participation in an investigational drug or device study within 90 days prior to screening Donation of blood>500 mL within 3 months prior to screening Known allergy to hyaluronidase, bee, or vespid venom, or any other ingredient in the formulation of rHuPH20 (Hylenex® recombinant [hyaluronidase human injection])

Known hypersensitivity to any of the study treatments or to excipients of recombinant human or humanized antibodies History of hypersensitivity or significant allergic reactions, spontaneous or following any prior drug administration Apparent clinically relevant family history of hypersensitivity, allergy, or severe cardiac diseases Lower extremity edema or pathology (e.g., cellulitis, lymphatic disorder or prior surgery, preexisting pain syndrome, previous lymph node dissection, etc.) that could interfere with any protocol-specified outcome assessment Any clinically relevant history of systemic disease (e.g., malignancy, diabetes mellitus, gastrointestinal, renal, hepatic, cardiovascular, rheumatological, or pulmonary disease)

History of breast cancer, treatment for breast cancer, or treatment with anthracylines or other cardiotoxic drugs Current disease or condition that could interfere with, or for which the treatment of might interfere with, the conduct of the study, or that would, in the opinion of the investigator, pose an unacceptable risk to the subject in this study Current chronic daily treatment (continuous for >3 months) with corticosteroids (dose≥10 mg/day methylprednisolone), excluding inhaled corticosteroids Receipt of IV antibiotics for infection within 7 days prior to enrollment into the study.

Study Entry Criteria: Part 2 (Female Patients with Early Breast Cancer)

Part 2 Inclusion Criteria

Patients must meet the following criteria for study entry:

Signed Informed Consent Form

Females age≥18 years

Able to comply with the study protocol, in the investigator's judgment

Eastern Cooperative Oncology Group performance status of 0

Current non-metastatic adenocarcinoma of the breast that meets the following criteria:
  a) Treated with adequate surgical procedure
  b) Completed standard anticancer (neo)adjuvant treatment (chemotherapy/biological)>7 months prior to study drug administration
  c) Treated with radiotherapy if applicable Baseline LVEF≥55% measured by ECHO or MUGA scan Negative pregnancy test in women of childbearing potential who are premenopausal or less than 12 months of amenorrhea post-menopause, and have not undergone surgical sterilization.

For women of childbearing potential: agreement to remain abstinent (refrain from heterosexual intercourse) or use non-hormonal contraceptive methods that result in a failure rate of <1% per year during the treatment period and for at least 7 months after the administration of pertuzumab and trastuzumab A woman is considered to be of childbearing potential if she is postmenarcheal, has not reached a postmenopausal state (≥12 continuous months of amenorrhea with no identified cause other than menopause), and has not undergone surgical sterilization (removal of ovaries and/or uterus).

Examples of contraceptive methods with a failure rate of <1% per year include bilateral tubal ligation, male sterilization and copper intrauterine devices (IUDs).

The reliability of sexual abstinence should be evaluated in relation to the duration of the clinical trial and the preferred and usual lifestyle of the patient. Periodic abstinence (e.g., calendar, ovulation, symptothermal, or postovulation methods) and withdrawal are not acceptable methods.

Part 2 Exclusion Criteria

Patients who meet any of the following criteria will be excluded from study entry:

Concurrent other malignancy requiring therapy of any modality that may interfere with PK investigations or result in unexpected toxicity Maximum cumulative dose of doxorubicin>360 mg/m$^2$ or maximum cumulative dose of epirubicin>720 mg/m$^2$ or any prior anthracyclines unrelated to the present breast cancer Serious, uncontrolled concomitant disease that would contraindicate the use of any of the investigational drugs used in this study or that would put the patient at high risk for treatment-related complications.

History of other malignancy within 5 years prior to screening, except for appropriately treated carcinoma in situ of the cervix, non-melanoma skin carcinoma, or Stage I uterine cancer Patients currently participating in other studies of investigational agents unless agreed by the investigator and Sponsor Serious cardiac illness or medical conditions Any previous or concurrent condition suggesting susceptibility to hypersensitivity or allergic reactions. Patients with mild or seasonal allergies may be included after discussion between the investigator and Sponsor.

Severe infusion-related reactions (IRRs) experienced during any previous therapy with pertuzumab or trastuzumab Known allergy to hyaluronidase, bee, or vespid venom, or any other ingredient in the formulation of Hylenex®

Any of the following abnormal laboratory tests on Day −1 prior to trastuzumab treatment:

Serum total bilirubin>1.25×upper limit of normal (ULN; with the exception of Gilbert's syndrome)

Alanine aminotransferase (ALT) or aspartate aminotransferase (AST)>1.25×ULN;

Albumin<25 g/L

Alkaline phosphatase (ALP)>2.5×ULN

Serum creatinine>1.5×ULN

Total white blood cell (WBC) count<2500 cells/mm3

Absolute neutrophil count<1500 cells/mm3

Platelets<100,000 cells/mm3
  Pregnant or lactating women, or women intending to become pregnant during the study
  Women of childbearing potential or less than 1 year after menopause (unless surgically sterile) who are unable or unwilling to use adequate contraceptive measures during study treatment and for 7 months after study drug administration Residual toxicity resulting from previous therapy (e.g., hematologic, cardiovascular or neurologic that is Grade≥2). Alopecia is permitted.

Uncontrolled hypertension (systolic BP>150 mmHg and/or diastolic BP>100 mmHg)

Clinically significant (i.e., active) cardiovascular disease, including but not limited to cerebrovascular accident/stroke or myocardial infarction within 6 months prior to first study treatment; unstable angina; CHF of NYHA Grade II or higher; serious cardiac arrhythmia requiring medication; or other cardiovascular problem that is uncontrolled or is currently controlled with medication Positive result on HBV, HCV, or HIV 1 or 2 test History of exposure to HBV, HCV, or HIV Active viral hepatitis infection (hepatitis B or C) or HIV infection Receipt of IV antibiotics for infection within 7 days prior to enrollment into the study Current chronic daily treatment (continuous for >3 months) with corticosteroids (dose equivalent to or greater than 10 mg/day methylprednisolone), excluding inhaled steroids Known hypersensitivity to any of the study treatments or to excipients of recombinant human or humanized antibodies.

Method of Treatment Assignment

Healthy volunteers and patients will be identified for potential recruitment using pre-screening enrollment logs, Institutional Review Board (IRB)/Ethics Committee (EC) ☐ approved newspaper/radio advertisements, and mailing lists prior to consenting to participate in the study.

Part 1 (Healthy Volunteers)

Approximately 48 healthy volunteers will be recruited initially for Part 1. Patient numbers will be allocated sequentially in the order in which they are enrolled. Additional dose-finding cohorts may be opened if necessary.

Part 2 (Patients with EBC)

Approximately 40 patients with EBC will be recruited for Part 2. Patient numbers will be allocated sequentially in the order in which they are enrolled.

Study Treatment

The investigational medicinal products (IMPs) for this study are pertuzumab and trastuzumab.

Formulation, Packaging and Handling

Study drug packaging will be overseen by the Roche clinical trial supplies department and bear a label with the identification required by local law, the protocol number, and drug identification and dosage. The packaging and labeling of the study drug will be in accordance with Roche standard and local regulations. Upon arrival of IMPs at the site, site personnel should check them for damage and verify proper identity, quantity, integrity of seals and temperature conditions and report any deviations or product complaints to the monitor upon discovery. The qualified individual responsible for dispensing the study drug will prepare the correct dose according to the schedule. This individual will write the date dispensed, date administered, and patient number and initials, as appropriate, on the label of the study drug vial and/or on the Drug Accountability Record. This individual will also record the study-drug batch or lot number received by each patient during the study.

Pertuzumab

Three formulations of pertuzumab were used:

Pertuzumab Formulation I is a sterile, colorless to slightly brownish concentrate for solution for infusion provided as single-use IV formulation containing 30 mg/mL pertuzumab in L-Histidine acetate buffer containing excipients sucrose and polysorbate 20. Each 20-mL vial contains 420 mg of pertuzumab (14.0 mL/vial).

Pertuzumab Formulation 2 is a sterile, colorless to slightly brownish solution for injection provided as single-use SC formulation containing 120 mg/mL pertuzumab in L-histidine acetate buffer containing excipients sucrose, polysorbate 20, methionine, and rHuPh20 (2000 U/mL). Each 10-mL vial contains 600 mg of pertuzumab (5.0 mL/vial).

Pertuzumab Formulation 3 is a sterile, colorless to slightly brownish solution for injection provided as single-use SC formulation containing 120 mg/mL pertuzumab in L-Histidine acetate buffer containing excipients sucrose, polysorbate 20, and methionine. Each 10-mL vial contains 600 mg of pertuzumab (5.0 mL/vial).

No preservative is used with pertuzumab since the vials are intended for single use only. The recommended storage conditions for the drug product are between 2° C. and 8° C., protected from light. The drug product must not be frozen.

Trastuzumab

Trastuzumab formulation is a sterile, colorless to slightly brownish concentrate solution for injection containing 120 mg/mL of trastuzumab in L-Histidine/Histidine-HCl buffer containing excipients trehalose, polysorbate 20, methionine, and rHuPh20 (2000 U/mL). Each 5-mL vial contains 600 mg of RO0452317 (5.0 mL/vial).

No preservative is used with trastuzumab since the vials are intended for single use only. The recommended storage conditions for the drug product are between 2° C. and 8° C., protected from light. The drug product must not be frozen.

Dosage, Administration and Compliance

Pertuzumab and Trastuzumab SC

The qualified individual responsible for dispensing the study drug will prepare the correct dose. This individual will write the date dispensed and subject number and initials on the study drug vial label and on the Drug Accountability Record. This individual will also record the study drug batch or lot number received by each subject during the study.

HMVs will receive a single dose of pertuzumab IV, pertuzumab SC, trastuzumab SC, or pertuzumab SC and trastuzumab SC mixed together (co-mixed). Patients will receive a single dose of pertuzumab and trastuzumab as two single-agent injections (co-administration) or one injection of pertuzumab and trastuzumab mixed together (co-mixed) or pertuzumab co-formulated with trastuzumab as one FDC injection.

Healthy volunteers and patients may also be administered a pre-medication (e.g., acetaminophen [paracetamol] and/or promethazine), prior to the administration of pertuzumab and/or trastuzumab SC, at the discretion of the investigator to reduce to risk of infusion- or injection-related reactions.

Any overdose or incorrect administration of study drug should be noted on the Study Drug Administration eCRF. Adverse events associated with an overdose or incorrect administration of study drug should be recorded on the Adverse Event eCRF.

Administered (Pertuzumab IV)

Healthy volunteers receiving pertuzumab IV (Cohort 1—control) were given a dose of 420 mg.

The dose of pertuzumab was administered over 60 (±10) minutes, and healthy volunteers were observed for a further 60 minutes. The infusion should be slowed or interrupted if the patient experiences infusion-related symptoms.

Administered Doses (Pertuzumab SC and Trastuzumab SC)

Healthy volunteers and patients receiving pertuzumab SC (Cohorts 2-8, A and B) were given doses between 400 and 1200 mg. Healthy volunteers and patients receiving trastuzumab SC (Cohorts 5-8, A and B) were given a dose of 600 mg (see Table 3).

TABLE 3

Doses and Cohorts

| Cohort | Agent | Dose (mg) | Injection Volume (mL) |
|---|---|---|---|
| HMV | | | |
| 1 | pertuzumab IV | 420 | |
| 2 | pertuzumab SC | 400 | 3.3 |
| 3 | pertuzumab SC | 600 | 5 |
| 4 | pertuzumab SC | 1200 | 10 |
| 5 | trastuzumab SC | 600 | 5 |
| 6 | pertuzumab SC + trastuzumab SC (co-mixed) | 400 + 600 | 8.3 |
| 7 | pertuzumab SC + trastuzumab SC (co-mixed) | 1200 + 600 | 15 |
| 8 | pertuzumab SC$^a$ + trastuzumab SC (co-mixed) | 1200 + 600 | 15 |
| 9$^b$ | pertuzumab IV/SC +/− trastuzumab SC | X +/− 600 | X |
| Patients | | | |
| A | pertuzumab SC + trastuzumab SC (co-admin) | TBD + 600 | TBD |

TABLE 3-continued

Doses and Cohorts

| Cohort | Agent | Dose (mg) | Injection Volume (mL) |
|---|---|---|---|
| B | pertuzumab SC + trastuzumab SC (co-mixed) | TBD + 600 | TBD |
| C | pertuzumab SC + trastuzumab SC (FDC) | TBD + 600 | TBD |

FDC = fixed-dose combination;
HMV = healthy male volunteer;
IV = intravenous;
rHuPH20 = recombinant human hyaluronidase;
SC = subcutaneous;
TBD = to be determined.
[a]rHuPH20 concentration = 667 U/mL only
[b]If additional cohort necessary SC injections were administered into the anterior thigh region. Patients in Cohort A will receive the two co-administration injections in opposite thighs, with the second injection administered immediately after the first.

The appropriate amount of solution should be withdrawn from the vials. Refer to the pharmacy manual for instruction.

The 27-gauge injection needle is inserted using sterile technique in the SC tissue of the thigh. The needle should be fully inserted, being careful that the tip of the needle is deeper than the dermis but not as deep as the underlying muscle. The goal of the placement angle and needle depth is to achieve uniform placement into every patient's SC tissue. Study drug should not be injected into moles, scars, or bruises. The skin should be pinched and needle inserted before the skin is released and the pressure on the syringe can be applied.

The injection should be manually pushed at a flow rate of no more than 2 mL/min, therefore administration should take approximately 2-8 minutes depending on the dose being administered. If there is a request by the subject to interrupt the injection, the pressure on the syringe should initially be eased to alleviate the pain. If the pain is not alleviated, the injection should be stopped and th subject should be asked when they are comfortable to resume the injection.

Timing in Relation to Meals, Physical Activities, and Procedures

Meals were similar in composition and time of administration across all cohorts. The consumption of foods and beverages containing caffeine (e.g., tea, coffee, chocolate, and soft drinks) or alcohol will not be permitted from Day −1 to Day 2. The use of tobacco is not permitted during the in-clinic portion of the study.

Light ambulatory activities will be permitted, with the level of activities kept as similar as possible on all days in the clinical research unit.

Concomitant Therapy, Prohibited Food, and Additional Restrictions

Concomitant therapy includes any medication (e.g., prescription drugs, over-the-counter drugs, vaccines, herbal or homeopathic remedies, nutritional supplements) used by a healthy volunteer/patient within 30 days of study screening. All such medications should be reported to the investigator and recorded on the Concomitant Medications eCRF.

Permitted Therapy

For the healthy volunteers, no concomitant medication will be permitted, with the exception of medications to treat adverse events, unless the rationale for exception is discussed between the investigator and Medical Monitor and clearly documented.

For patients with EBC, the following treatments are permitted during the study:

Acceptable methods of contraception must be used when the female patient or male partner is not surgically sterilized or does not meet the study definition of postmenopausal (≥12 months of amenorrhea)

$H_1$ and $H_2$ antagonists (e.g., diphenhydramine, cimetidine)

Cardiovascular medications: angiotensin-converting enzyme (ACE) inhibitors, angiotensin receptor blockers, β blockers, calcium-channel blockers and diuretics (for treatment of arterial hypertension with a goal to reduce blood pressure to <140/90 mmHg), β blockers, calcium-channel blockers, and digoxin (for heart rate control), and thrombocyte aggregation inhibitors Analgesics/anti-inflammatories (e.g., paracetamol/acetaminophen, meperidine, opioids)

Short-term use of corticosteroids to treat or prevent allergic or infusion reactions Anti-emetics (approved prophylactic serotonin antagonists, benzodiazepines, dopamine antagonists, etc.)

Medication to treat diarrhea (e.g., loperamide)

Estrogen-receptor antagonists (e.g., tamoxifen), aromatase inhibitors (e.g., anastrazole, exemestane), and gonadotrophin hormone-releasing hormone agonists (e.g., buserelin, triptorelin) after surgery, as per local practice and guidelines Ovarian suppression (luteinizing hormone-releasing hormone [LHRH] analog)

Bisphosphonates (to be used in accordance with the approved labeled indication and/or nationally recognized treatment guidelines)

At the discretion of the investigator, healthy volunteers and patients may also be administered a pre-medication (e.g., acetaminophen [paracetamol] and/or promethazine) prior to the administration of pertuzumab and/or trastuzumab SC to reduce the risk of IRRs or injection-related reactions.

Prohibited Therapy

Use of the following therapies is prohibited during the study and for at least 10 days prior to initiation of study treatment:

Anti-cancer therapies other than those administered in this study or listed in permitted therapies above, including cytotoxic chemotherapy, radiotherapy, immunotherapy, and biological anti-cancer therapy Any targeted therapy, other than those used in this study Any investigational agent, except for those used for this study Initiation of herbal remedies: Herbal remedies initiated prior to study entry and continuing during the study are not permitted and must be reported on the appropriate eCRF.

Any systemically active, oral, injected, or implanted hormonal method of contraception, except for progesterone-coated IUDs that had been previously implanted Estrogen-replacement therapy (hormone-replacement therapy)

No prescription medicines, over-the-counter medicines, or herbal remedies are allowed for at least 10 days before study drug dose, through the end of the study unless either agreed by study doctor.

Prohibited Food

The consumption of foods and beverages containing caffeine (e.g., tea, coffee, chocolate, and soft drinks) or alcohol will not be permitted from Day −1 to Day 2.

Additional Restrictions

Meals will be similar in composition and time of administration across all cohorts. The use of tobacco is not permitted during the in-clinic portion of the study. Light ambulatory activities will be permitted, with the level of activities kept as similar as possible on all days in the clinical research unit.

Study Assessments

Part 1 (Male Healthy Volunteers)

Healthy volunteers will report to the unit on Day −1 for pre-dose assessments and will stay overnight (for 3 nights) at the unit. Healthy volunteers may be discharged on the morning of Day 2 at the discretion of the investigator and return to the clinic on Day 3.

On Day 1, healthy volunteers will be given pertuzumab by IV infusion or a SC injection of pertuzumab, trastuzumab SC, or pertuzumab and trastuzumab SC (co-mixed) into the anterior thigh region. Injection sites will be digitally photographed after a SC injection if a severe adverse reaction is observed at the injection site.

Safety and pharmacokinetic assessments will be performed at regular intervals during the study according to the schedule of assessments. Healthy volunteers will remain in the unit until the 48-hour pharmacokinetic assessment is complete. They will return for PK and safety assessments on specified days afterwards.

A follow-up visit will be performed 7 months after study drug administration. Healthy volunteers will be discharged from the study by a responsible physician upon completion of the follow-up visit.

Part 2 (Female Patients with EBC)

Patients will report to the unit on Day −1 for pre-dose assessments. Patients will return to the unit on Day 1 and will be given pertuzumab and trastuzumab as an SC injection into the anterior thigh region. Patients in Cohort A will receive the 2 injections in opposite thighs, with the second injection administered immediately after the first. Injection sites will be digitally photographed after a SC injection if a severe adverse reaction at the injection site is observed.

Safety and PK assessments will be performed at regular intervals during the study as per the schedule of assessments. Patients will remain in the unit until 12 hours post-dose. They will return for pharmacokinetic and safety assessments on specified days afterwards.

A follow-up visit will be performed 7 months after study drug administration. Patients will be discharged from the study by a responsible physician upon completion of the follow-up visit.

Follow-Up Visit

For HMVs or EBC patients with ongoing cardiac adverse events (regardless of cause) or study treatment-related adverse events, serious adverse events, or events of special interest on Day 85 or adverse events, serious adverse events, or events of special interest occurring between the Day 85 and the follow-up visit, all assessments in the follow-up visit will be performed and PK/ATA samples taken.

For HMVs with no cardiac adverse events (regardless of cause) or study treatment-related adverse events, serious adverse events, or adverse events of special interest ongoing on Day 85 and none occurring between the Day 85 and the follow-up visit, only the pregnancy follow-up of female partners is required. This visit may be performed by phone call.

For EBC patients with no cardiac adverse events (regardless of cause) or study treatment-related adverse events, serious adverse events, and adverse events of special interest ongoing on Day 85 and none occurring between the Day 85 and the follow-up visit, only the pregnancy test (for patients of childbearing potential) is required at this visit.

For postmenopausal EBC patients (≥12 months of amenorrhea) with no cardiac adverse events (regardless of cause) or study treatment-related adverse events, serious adverse events, and adverse events of special interest ongoing on Day 85 and none occurring between the Day 85 and the follow-up visit, the follow up visit may be performed by phone call.

Safety Parameters and Adverse Events

Safety assessments will consist of monitoring and recording adverse events, including serious adverse events and adverse events of special interest, performing protocol-specified safety laboratory assessments, measuring protocol-specified vital signs, and conducting other protocol-specified tests that are deemed critical to the safety evaluation of the study.

Adverse Events

According to the Guidelines for Good Clinical Practice, an adverse event is any untoward medical occurrence in a clinical investigation subject administered a pharmaceutical product, regardless of causal attribution. An adverse event can therefore be any of the following:

Any unfavorable and unintended sign (including an abnormal laboratory finding), symptom, or disease temporally associated with the use of a medicinal product, whether or not considered related to the medicinal product.

Any new disease or exacerbation of an existing disease (a worsening in the character, frequency, or severity of a known condition).

Recurrence of an intermittent medical condition (e.g., headache) not present at baseline.

Any deterioration in a laboratory value or other clinical test (e.g., ECG, X-ray) that is associated with symptoms or leads to a change in study treatment or concomitant treatment or discontinuation from study drug.

Adverse events that are related to a protocol-mandated intervention, including those that occur prior to assignment of study treatment (e.g., screening invasive procedures such as biopsies).

Serious Adverse Events (Immediately Reportable to the Sponsor)

A serious adverse event is any adverse event that meets any of the following criteria:

Is fatal (i.e., the adverse event actually causes or leads to death)

Is life threatening (i.e., the adverse event, in the view of the investigator, places the patient at immediate risk of death). This does not include any adverse event that had it occurred in a more severe form or was allowed to continue might have caused death.

Requires or prolongs inpatient hospitalization.

Results in persistent or significant disability/incapacity (i.e., the adverse event results in substantial disruption of the patient's ability to conduct normal life functions.

Is a congenital anomaly/birth defect in a neonate/infant born to a mother exposed to study drug.

Is a significant medical event in the investigator's judgment (e.g., may jeopardize the patient or may require medical/surgical intervention to prevent one of the outcomes listed above).

The terms "severe" and "serious" are not synonymous. Severity refers to the intensity of an adverse event (e.g., rated as mild, moderate, or severe, or according to NCI CTCAE v4.03; the event itself may be of relatively minor medical significance (such as severe headache without any further findings).

TABLE 4

Adverse Event Severity Grading Scale for Events Not Specifically Listed in NCI CTCAE

| Grade | Severity |
|---|---|
| 1 | Mild; asymptomatic or mild symptoms; clinical or diagnostic observations only; or intervention not indicated |
| 2 | Moderate; minimal, local, or non-invasive intervention indicated; or limiting age-appropriate instrumental activities of daily living[a] |
| 3 | Severe or medically significant, but not immediately life-threatening; hospitalization or prolongation of hospitalization indicated; disabling; or limiting self-care activities of daily living[b,c] |
| 4 | Life-threatening consequences or urgent intervention indicated[d] |
| 5 | Death related to adverse event[d] |

NCI CTCAE = National Cancer Institute Common Terminology Criteria for Adverse Events.
Note:
Based on the most recent version of NCI CTCAE (v4.03)
[a]Instrumental activities of daily living refer to preparing meals, shopping for groceries or clothes, using the telephone, managing money, etc.
[b]Examples of self-care activities of daily living include bathing, dressing and undressing, feeding oneself, using the toilet, and taking medications, as performed by patients who are not bedridden.
[c]If an event is assessed as a "significant medical event," it must be reported as a serious adverse event, per the definition of serious adverse event.
[d]Grade 4 and 5 events must be reported as serious adverse events, per the definition of serious adverse event.

Adverse Events of Special Interest (Immediately Reportable to the Sponsor)

Adverse events of special interest are required to be reported by the investigator to the Sponsor immediately (i.e., no more than 24 hours after learning of the event. Adverse events of special interest for this study include the following:

Cases of potential drug-induced liver injury that include an elevated ALT or AST in combination with either an elevated bilirubin or clinical jaundice, as defined by Hy's law.

Suspected transmission of an infectious agent by the study drug, as defined: Any organism, virus, or infectious particle (e.g., prion protein transmitting transmissible spongiform encephalopathy), pathogenic or non-pathogenic, is considered an infectious agent. A transmission of an infectious agent may be suspected from clinical symptoms or laboratory findings that indicate an infection in a patient exposed to a medicinal product. This term applies only when a contamination of the study drug is suspected.

An asymptomatic decline in LVEF requiring treatment. Note: In general, asymptomatic declines in LVEF should not be reported as adverse events since LVEF data are collected separately on the eCRF. Exceptions to this rule are as follows:

An asymptomatic decline in LVEF to a value of 10-percentage points below baseline or lower and <50% must be reported as an adverse event.

An asymptomatic decline in LVEF that requires treatment or that leads to discontinuation of study treatment must be reported in an expedited manner using the Adverse Event eCRF and classifying the event as a non-serious event of special interest that is immediately reportable.

Selected Adverse Events

Heart Failure

Symptomatic LVSD (referred to as heart failure) should be reported as a serious adverse event. If the diagnosis is heart failure, it should be reported as such, and not as individual signs and symptoms of heart failure. On the eCRF, signs and symptoms should be recorded. A cardiac consultation is recommended for patients who develop symptomatic LVSD (heart failure). Heart failure should be graded according to NCI CTCAE v4.03 (Grade 2, 3, 4, or 5), as well as according to the NYHA classification (Class II, III, and IV). Left ventricular systolic dysfunction should not be used to describe symptomatic dysfunction, as per NCI CTCAE v4.03.

Heart failure occurring during the study and up to 5 years after the last patient enrolled must be reported irrespective of causal relationship and followed until one of the following occurs: resolution or improvement to baseline status, no further improvement can be expected, or death.

Asymptomatic Declines in Left Ventricular Ejection Fraction

Asymptomatic declines in LVEF should not be reported as adverse events because LVEF data are collected separately on the eCRF. Exceptions to this rule are as follows:

An asymptomatic decline in LVEF of ≥10-percentage points from baseline to an LVEF<50% must be reported as an adverse event with the term of ejection fraction decreased, as per NCI CTCAE v4.03. In addition, a comment in the adverse events comments field should confirm that the event was asymptomatic.

An asymptomatic decline in LVEF requiring treatment or leading to discontinuation of pertuzumab and trastuzumab must also be reported. This adverse event should also be captured as a non-serious event of special interest on the serious adverse event form, and a comment should be added to the adverse events comments field, confirming that the event was asymptomatic.

Table 5 shows the New York Heart Association Classification and Left Ventricular Systolic Dysfunction National Cancer Institute Common Terminology Criteria for Adverse Events, Version 4.03 grading.

TABLE 5

| Class I | Patients with cardiac disease but without resulting limitations of physical activity. Ordinary physical activity does not cause undue fatigue, palpitation, dyspnea or anginal pain. |
|---|---|
| Class II | Patients with cardiac disease resulting in slight limitations of physical activity. They are comfortable at rest. Ordinary physical activity results in fatigue, palpitation, dyspnea or anginal pain. |
| Class III | Patients with cardiac disease resulting in marked limitations of physical activity. They are comfortable at rest. Less than ordinary physical activity causes fatigue, palpitation, dyspnea or anginal pain. |
| Class IV | Patients with cardiac disease resulting in inability to carry on any physical activity without discomfort. Symptoms of cardiac insufficiency or of the angina syndrome may be present even at rest. If any physical activity is undertaken, discomfort is increased. |

Weatherall D J, Lendingham J G G, editors. Oxford Rextbook of Medicine. Third Edition. New York: Oxford University Press, 1996.

Table 6 summarizes the reporting conventions for LVSD and Heart Failure:

TABLE 6

Reporting Conventions for left Ventricular Systolic Dysfunction/Heart Failure

| Observation | How to Report | Term to be Reported | Grading |
|---|---|---|---|
| Asymptomatic decline in LVEF of <10% points from baseline or to an LVEF of ≥50% | No additional reporting required; LVEF results to be reported on eCRF. | NA | NA |
| Asymptomatic decline in LVEF of ≥10% points from baseline to an LVEF of <50% | AE[a] (eCRF AE eForm) | Ejection fraction decreased[a] | NCI CTCAE for "ejection fraction decreased" |
| Asymptomatic decline in LVEF requiring treatment or leading to discontinuation of pertuzumab and/or trastuzumab | AE (eCRF AE eForm) and report as a non-serious AESI (reported on an SAE form) | Ejection fraction decreased[a] | NCI CTCAE for "ejection fraction decreased" |
| Heart failure/CHF (symptomatic LVSD)[b] | AE (eCRF AE eForm) and SAE (SAE form) | "Heart failure" | NCI CTCAE for "heart failure" and NYHA class |

AE = adverse event;
AESI = adverse event of special interest;
CHF = congestive heart failure;
eCRF = electronic Case Report Form;
LVEF = left ventricular ejection fraction;
LVSD = left ventricular systolic dysfunction;
NA = not applicable;
NCI CTCAE = National Cancer Institute Common Terminology Criteria for Adverse Events;
NYHA = New York Heart Association;
SAE = serious adverse event.
Note:
Any symptomatic LVSD event must be reported as heart failure.
[a]Report the status as asymptomatic and provide the LVEF value in the comments field as appropriate.
[b]Any symptomatic LVSD event must be reported as "heart failure."

The adverse event severity grading scale for the NCI CTCAE (v4.03) will be used for assessing adverse event severity. See Table 4 above for assessing severity for adverse events that are not specifically listed in the NCI CTCAE.

Assessment of Casualty of Adverse Events

Investigators should use their own knowledge of the patient, the circumstances surrounding the event, and an evaluation of any potential alternative causes to determine whether an adverse event is considered to be related to the study drug, indicating "yes" or "no" accordingly. The following guidance should be taken into consideration:
  Temporal relationship of event onset to the initiation of study drug
  Course of the event, considering especially the effects of dose reduction, discontinuation of study drug, or reintroduction of study drug (as applicable)\
  Known association of the event with the study drug or with similar treatments
  Known association of the event with the disease under study
  Presence of risk factors in the patient or use of concomitant medications known to increase the occurrence of the event
  Presence of non-treatment-related factors that are known to be associated with the occurrence of the event For patients receiving combination therapy, causality will be assessed individually for each protocol-mandated therapy.

Infusion-Related Reactions, Injection Reactions, and Local Injection Site Reactions Adverse events that occur during or within 24 hours after study drug administration and are judged to be related to study drug infusion or injection should be captured as a diagnosis (e.g., "infusion-related reaction," "injection reaction," "injection-site reaction") on the Adverse Event eCRF. If possible, avoid ambiguous terms such as "systemic reaction."

Associated signs and symptoms should be recorded on the dedicated Infusion-Related Reaction eCRF, Injection Reaction eCRF, or Injection-Site Reaction eCRF. If a patient experiences both a local and systemic reaction to the same dose of study drug, each reaction should be recorded separately on the Adverse Event eCRF with signs and symptoms also recorded separately on the dedicated Infusion-Related Reaction eCRF, Injection Reaction eCRF, or Injection-Site Reaction eCRF.

Adverse Events that are Secondary to Other Events

In general, adverse events that are secondary to other events (e.g., cascade events or clinical sequelae) should be identified by their primary cause, with the exception of severe or serious secondary events. A medically significant secondary adverse event that is separated in time from the initiating event should be recorded as an independent event on the Adverse Event eCRF. For example
  If vomiting results in mild dehydration with no additional treatment in a healthy adult, only vomiting should be reported on the eCRF
  If vomiting results in severe dehydration, both events should be reported separately on the eCRF
  If a severe gastrointestinal hemorrhage leads to renal failure, both events should be reported separately on the eCRF
  If dizziness leads to a fall and consequent fracture, all three events should be reported separately on the eCRF.

If neutropenia is accompanied by an infection, both events should be reported separately on the eCRF.

All adverse events should be recorded separately on the Adverse Event eCRF if it is unclear as to whether the events are associated.

Persistent of Recurrent Adverse Events

A persistent adverse event is one that extends continuously, without resolution, between patient evaluation timepoints. Such events should only be recorded once on the Adverse Event eCRF. The initial severity (intensity or grade) of the event will be recorded at the time the event is first reported. If a persistent adverse event becomes more severe, the most extreme severity should also be recorded on the Adverse Event eCRF. If the event becomes serious, it should be reported to the Sponsor immediately (i.e., no more than 24 hours after learning that the event became serious. The Adverse Event eCRF should be updated by changing the event from "non-serious" to "serious," providing the date that the event became serious, and completing all data fields related to serious adverse events.

A recurrent adverse event is one that resolves between patient evaluation timepoints and subsequently recurs. Each recurrence of an adverse event should be recorded as a separate event on the Adverse Event eCRF.

Abnormal Laboratory Values

Not every laboratory abnormality qualifies as an adverse event. A laboratory test result must be reported as an adverse event if it meets any of the following criteria:

Is accompanied by clinical symptoms

Results in a change in study treatment (e.g., dosage modification, treatment interruption, or treatment discontinuation)

Results in a medical intervention (e.g., potassium supplementation for hypokalemia) or a change in concomitant therapy Is clinically significant in the investigator's judgment. Note: For oncology trials, certain abnormal values may not qualify as adverse events.

It is the investigator's responsibility to review all laboratory findings. Medical and scientific judgment should be exercised in deciding whether an isolated laboratory abnormality should be classified as an adverse event.

If a clinically significant laboratory abnormality is a sign of a disease or syndrome (e.g., ALP and bilirubin 5×ULN associated with cholestasis), only the diagnosis (i.e., cholestasis) should be recorded on the Adverse Event eCRF.

If a clinically significant laboratory abnormality is not a sign of a disease or syndrome, the abnormality itself should be recorded on the Adverse Event eCRF, along with a descriptor indicating whether the test result is above or below the normal range (e.g., "elevated potassium," as opposed to "abnormal potassium"). If the laboratory abnormality can be characterized by a precise clinical term per standard definitions, the clinical term should be recorded as the adverse event. For example, an elevated serum potassium level of 7.0 mEq/L should be recorded as "hyperkalemia."

Observations of the same clinically significant laboratory abnormality from visit to visit should only be recorded once on the Adverse Event eCRF.

Abnormal Vital Sign Values

Not every vital sign abnormality qualifies as an adverse event. A vital sign result must be reported as an adverse event if it meets any of the following criteria:

Is accompanied by clinical symptoms

Results in a change in study treatment (e.g., dosage modification, treatment interruption, or treatment discontinuation)

Results in a medical intervention or a change in concomitant therapy

Is clinically significant in the investigator's judgment

It is the investigator's responsibility to review all vital sign findings. Medical and scientific judgment should be exercised in deciding whether an isolated vital sign abnormality should be classified as an adverse event.

If a clinically significant vital sign abnormality is a sign of a disease or syndrome (e.g., high BP), only the diagnosis (i.e., hypertension) should be recorded on the Adverse Event eCRF.

Observations of the same clinically significant vital sign abnormality from visit to visit should only be recorded once on the Adverse Event eCRF.

Results of Pk Studies and Dose Selection

Part 1 SC PK Analyses and Dose Selection

The selection of the pertuzumab SC doses in Part 1 (Cohorts 2, 3, and 4) was based on the pertuzumab IV popPK model with the values of the trastuzumab SC PK parameters incorporated. For better accuracy, IV popPK from historical model parameter estimates was also relied on in the SC dose selection analyses. Following the estimation of fixed PK parameters (i.e., $C_{trough}$, AUC0-inf, maximum serum concentration $[C_{max}]$, time of maximum serum concentration $[T_{max}]$), the pertuzumab SC (maintenance) dose(s) was selected for Part 2. This SC dose was calculated to deliver a similar pertuzumab exposure to that of IV pertuzumab at 420 mg. Equally, based on PK parameters, one pertuzumab SC (loading) dose was calculated to deliver a similar pertuzumab exposure to that of IV pertuzumab at 840 mg. The pertuzumab IV popPK model was updated with pertuzumab SC parameters using the Part 1 data and was used to correctly identify the SC maintenance and loading doses.

FIG. 8 shows the study overview, including the antibody dosages, injections volumes, and rHuPH20 (Halozyme) concentrations and amounts for cohorts 1-8.

Figure 9:
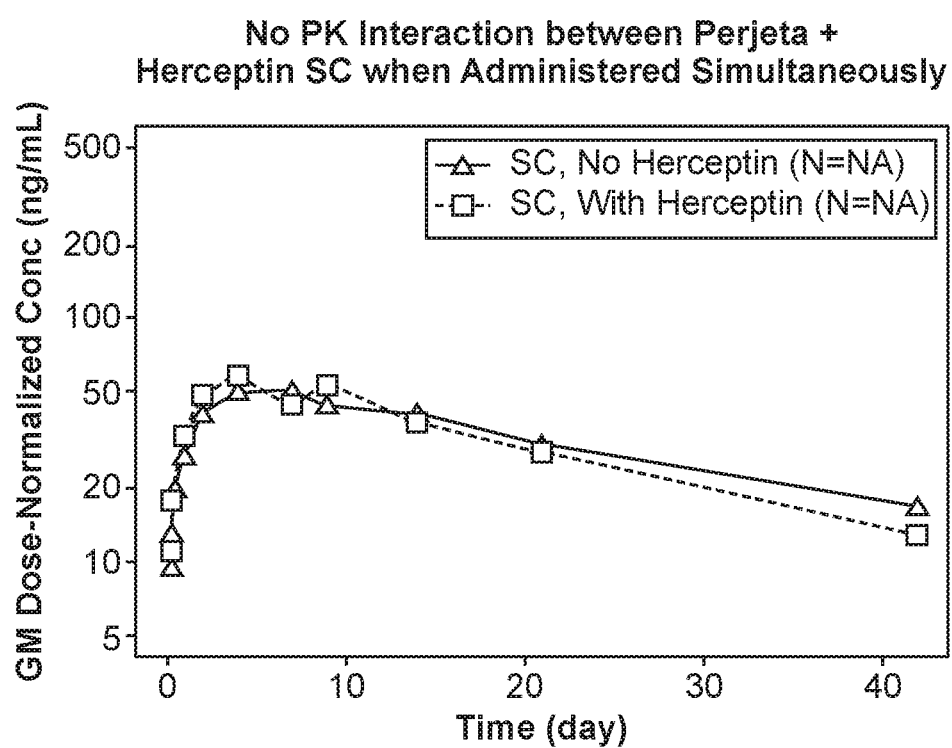
FIG. 9 shows dose normalized concentrations (μg/mL) of subcutaneously administered pertuzumab, with and without trastuzumab, as a function of time (days).

FIG. 9 shows dose normalized concentrations (µg/mL) of subcutaneously administered pertuzumab, with and without trastuzumab, as a function of time (days). The data show that there is no PK interaction between pertuzumab SC and trastuzumab SC when administered simultaneously. No differences were seen between the PK of trastuzumab SC administered as monotherapy or with pertuzumab SC.

Figure 10:
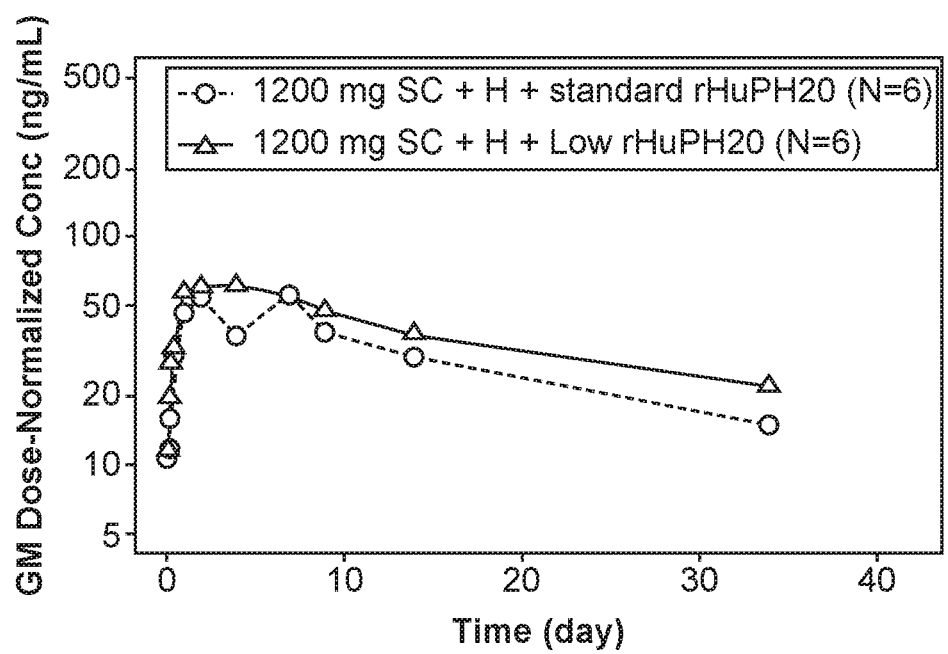
FIG. 10 shows dose-normalized concentrations (μg/mL) of pertuzumab as a function of time (days) with different concentrations of rHuPH20.

FIG. 10 shows dose normalized concentrations (µg/mL) of pertuzumab as a function of time (days). There were no significant differences in pertuzumab PK or trastuzumab PK (not shown) when administered with 2,000 U/mL or 667 U/mL rHuPH20.

Figure 11:
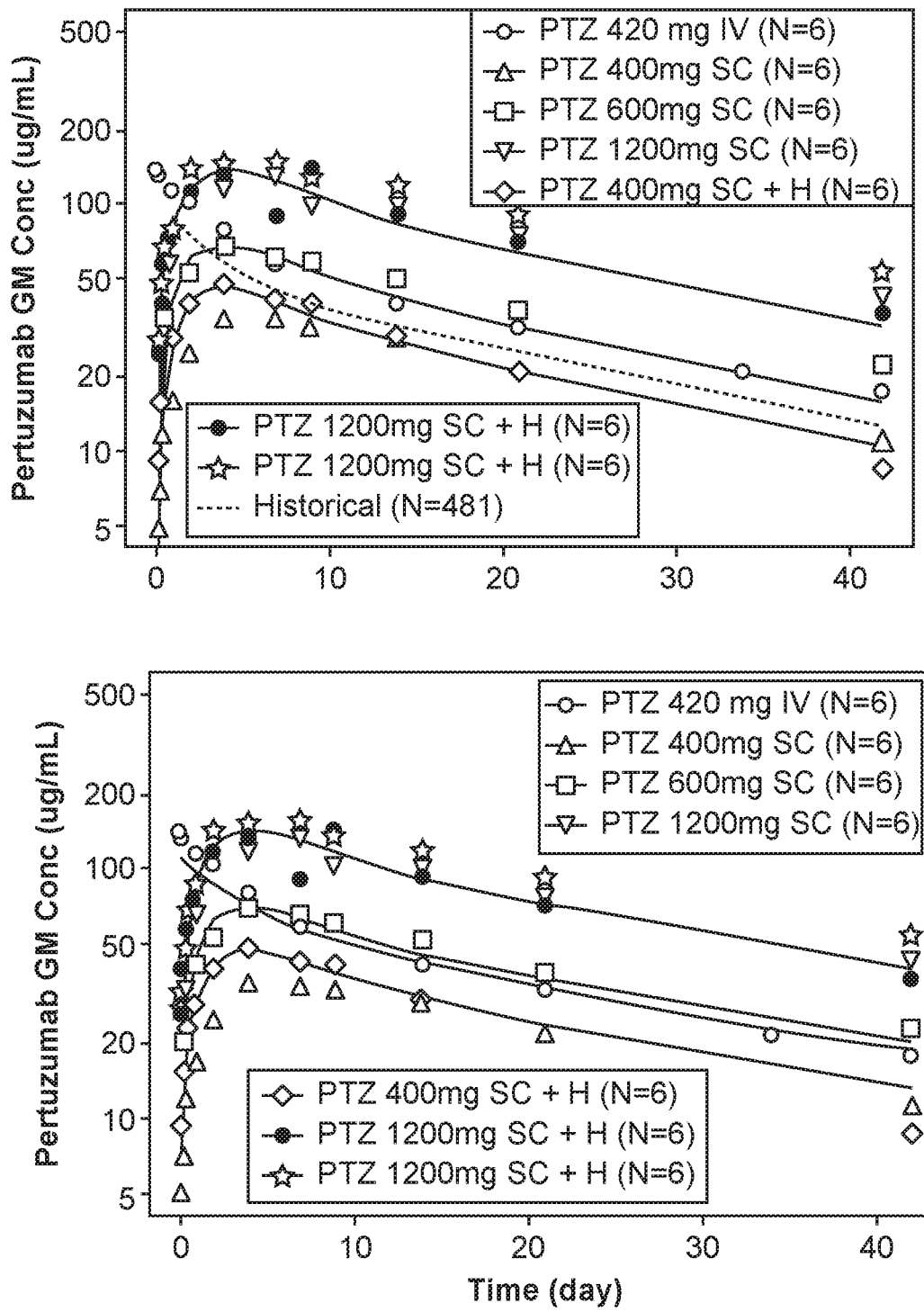
FIG. 11 shows the parameter estimations using the pertuzumab and the historical population PK (popPK) IV models in comparison.

FIG. 11 shows the parameter estimations using the pertuzumab and the historical population PK (popPK) IV models in comparison at different pertuzumab concentrations administered IV or SC, with and without trastuzumab.

Characterization of Pertuzumab Pharmacokinetics—Part 1

Figure 24:
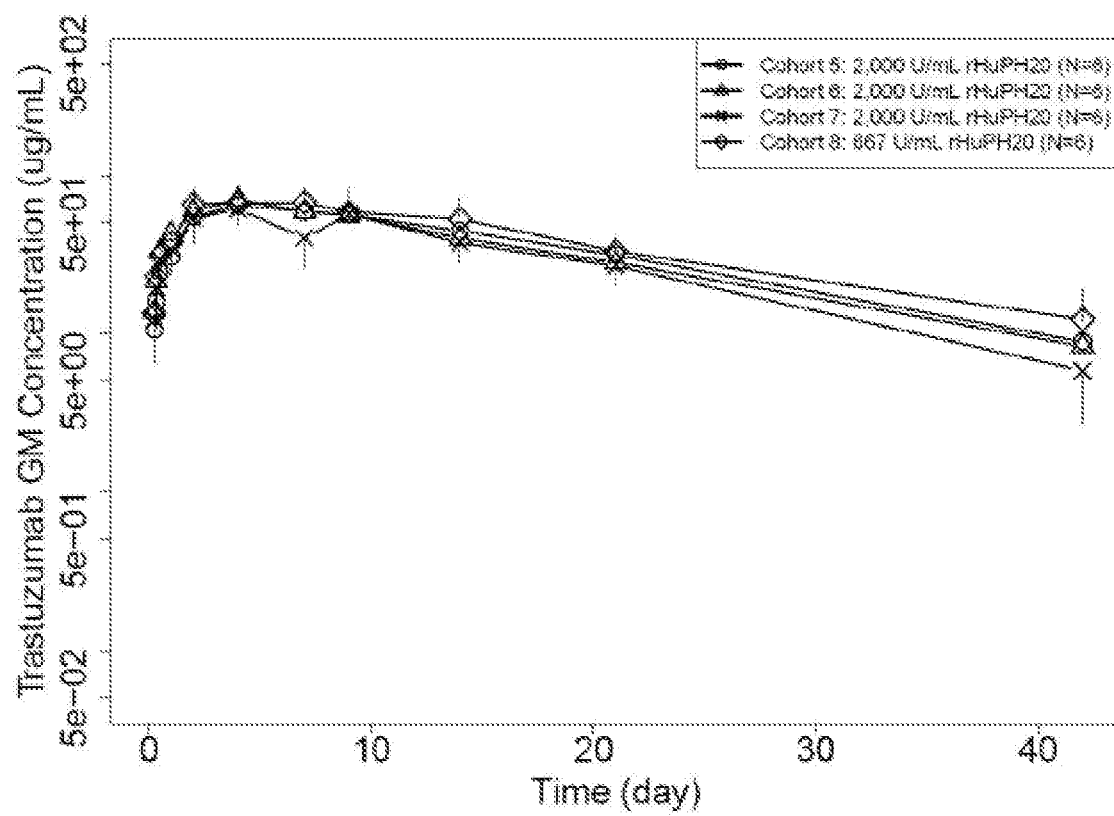
FIG. 24 Geometric Mean Serum Trastuzumab Concentration-Time Profile With 667 U/mL or 2,000 U/mL rHuPH20 (HMV).

Mean pertuzumab concentration-time profiles for Cohorts 1-4 and 6-8 are shown in FIG. 24. The pertuzumab concentrations after an intravenously administered dose of 420 mg followed a biphasic pattern with a distinct distribution and elimination phase. Subcutaneously administered pertuzumab resulted in a time to reach maximum concentration ($T_{max}$) between 4-7 days and dose-related increases in exposure. Variability within some of the 1200 mg SC cohorts was observed, likely due to a small sample size.

Figure 22:
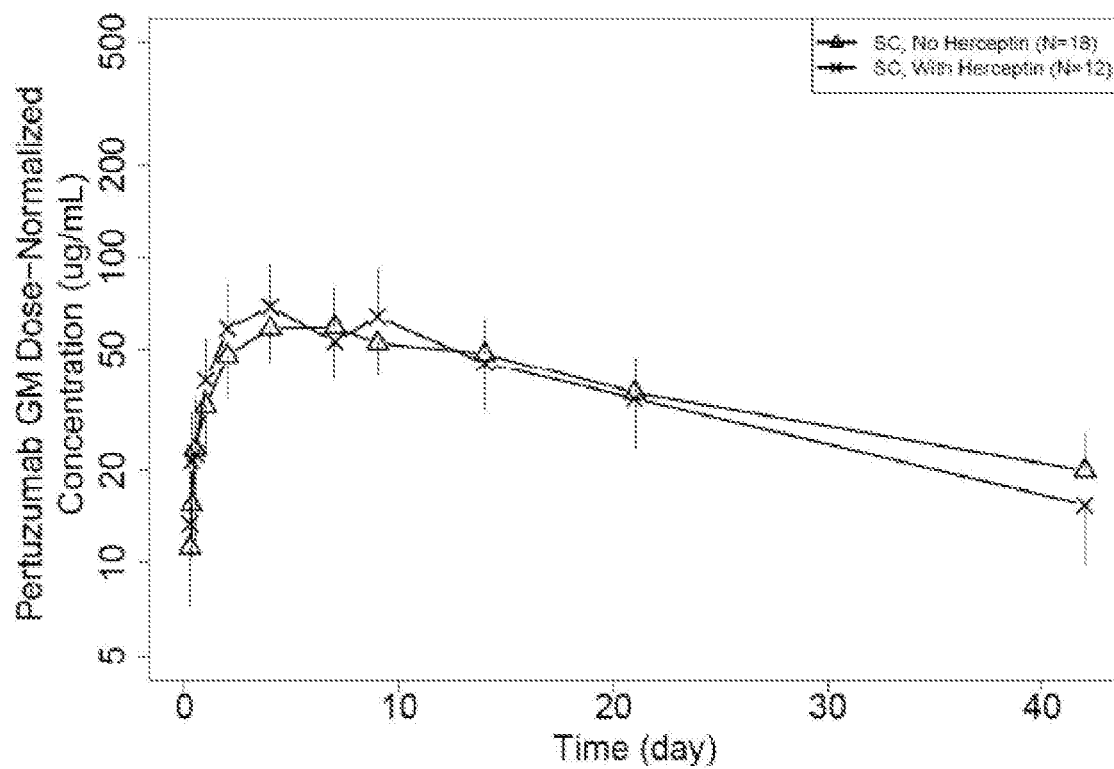
FIG. 22 Geometric Mean Dose-Normalized Serum Pertuzumab Concentration-Time Profile. With and Without Concomitant Herceptin FIG. 23 Geometric Mean Serum Pertuzumab Concentration-Time Profile With 667 U/mL or 2,000 U/mL rHuPH20 (HMV)

Pertuzumab geometric mean dose-normalized concentrations when administered with and without trastuzumab were compared to assess the potential impact of trastuzumab on the PK of pertuzumab. As shown in FIG. 22, there was no apparent impact of trastuzumab on the PK of pertuzumab when the two antibodies were delivered SC co-mixed. This is consistent with PK data from previous studied where the two antibodies were administered sequentially.

Figure 20:
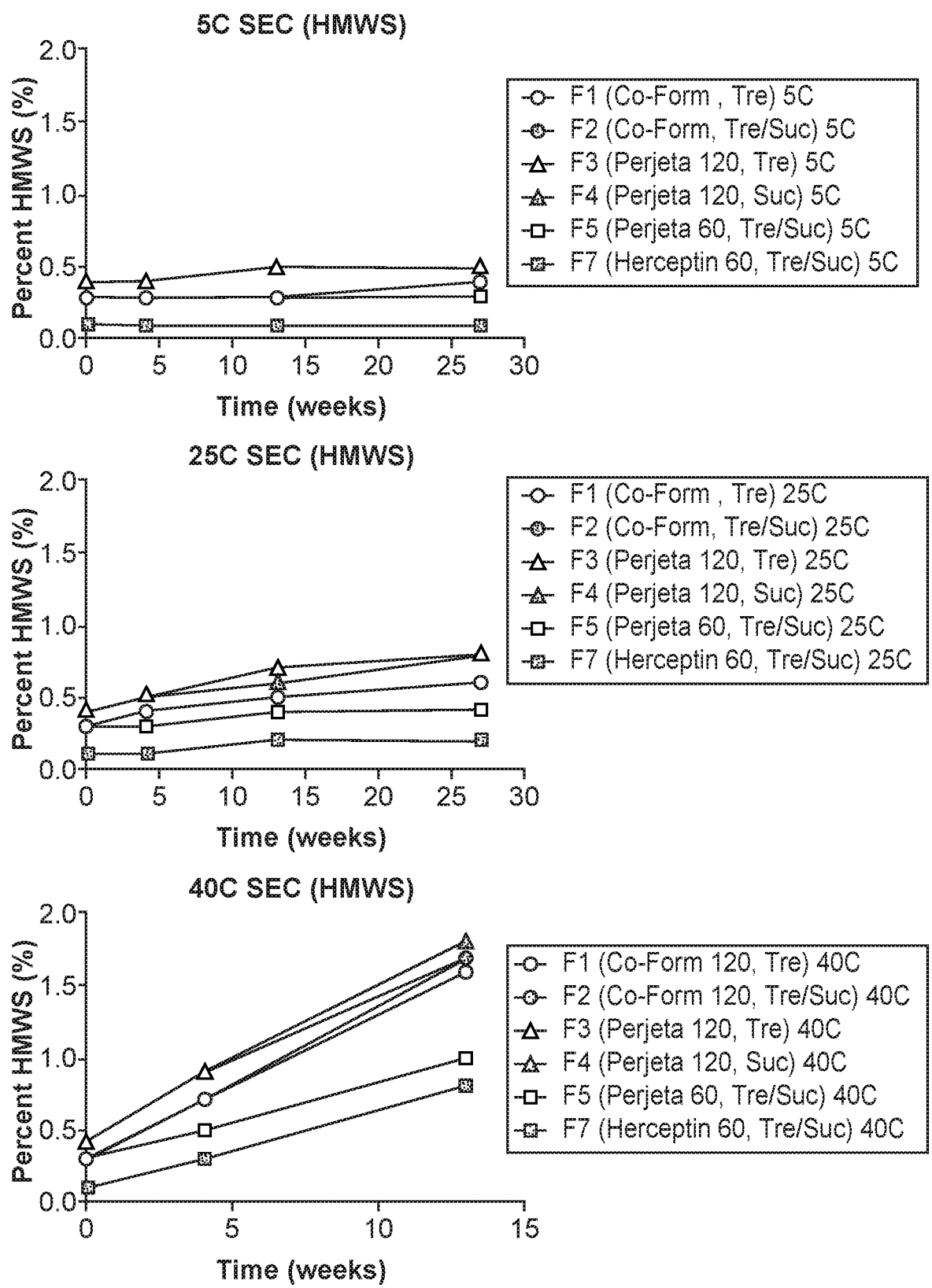
FIG. 20 shows the amount (%) of high molecular weight species (HMWS) in various subcutaneous pertuzumab and trastuzumab formulations, and pertuzumab/trastuzumab co-formulations at 5° C. and 25° C., respectively.
Figure 21:
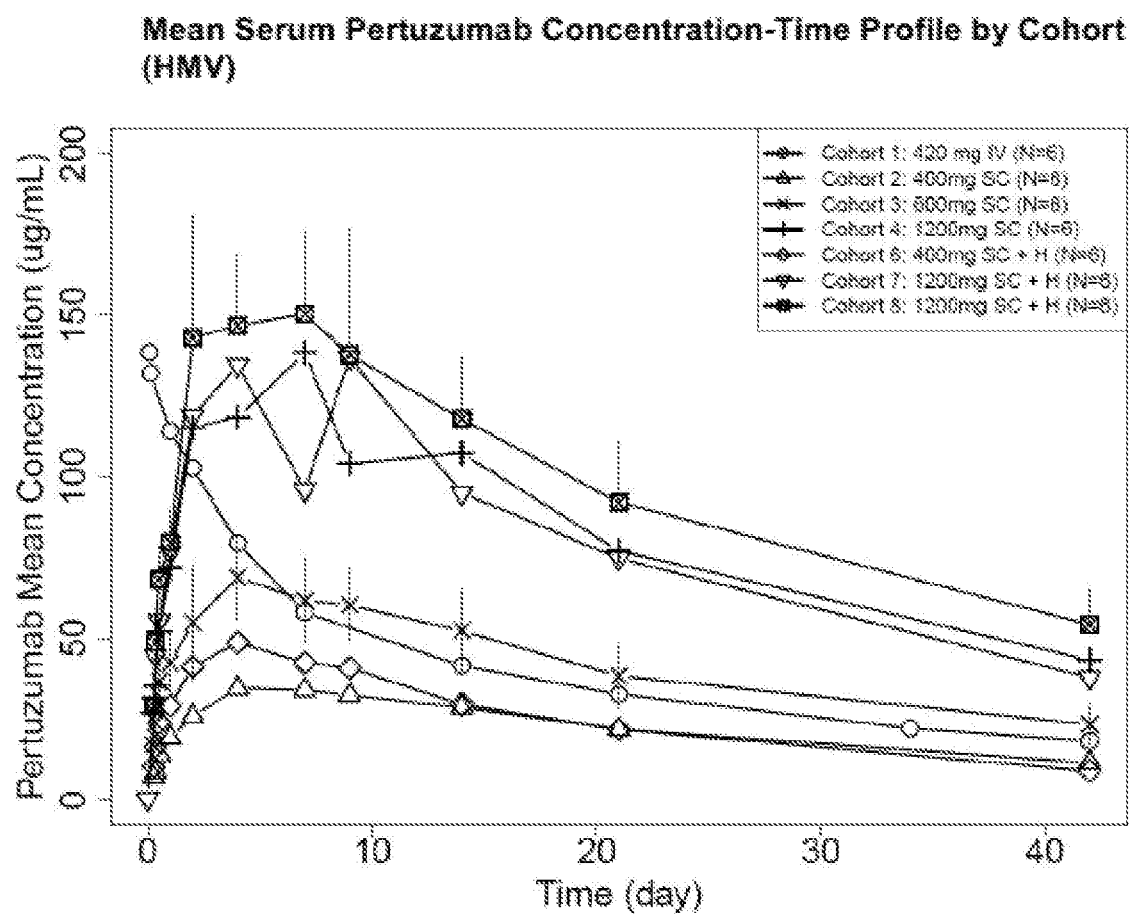
FIG. 21 Mean Serum Pertuzumab Concentration-Time Profile by Cohort

Pertuzumab geometric mean concentrations when administered with 667 U/mL or 2,000 U/mL rHuPH20 were compared to assess the potential impact of the absorption enhancing enzyme rhuPH20 on pertuzumab PK. There was no apparent impact of lowering the rHuPH20 concentration from 2,000 U/mL to 667 U/mL on the PK of pertuzumab or trastuzumab, as shown in FIGS. 20 and 21, respectively.

The characterization of pertuzumab PK indicated that trastuzumab (resulting from simultaneous trastuzumab SC administration) has no apparent impact on pertuzumab. Pertuzumab PK appeared mainly unaltered by lowering the rHuPH20 concentration from 2,000 U/mL to 667 U/mL, however, as only a small number of subjects were exposed to each concentration (n=6 per cohort), it was difficult to rule out possible differences particularly in the terminal phase and $C_{trough}$. These observations supported further analyses to determine the pertuzumab SC dose that was non-inferior to pertuzumab IV 420 mg.

Population PK Model Development to Select Pertuzumab SC Dose

A pertuzumab SC 1200 loading dose was selected based on pertuzumab dose-proportionality and linear pharmacokinetics suggested by the popPK model developed. Model-based simulations confirmed comparable exposures between pertuzumab 1200 SC and 840 mg IV. Observed pertuzumab exposures from the 1200 mg SC cohorts from Part 1 further confirmed the loading dose selection when compared with IV exposures observed in historical studies.

Characterization of Pertuzumab Pharmacokinetics—Part 2

Given no apparent pharmacokinetic (PK) drug-drug interaction (DDI) between pertuzumab and trastuzumab when co-mixed in Part 1, and technical development of the fixed-dose co-formulation (FDC) was e feasible, Cohort A (co-administration of 600 mg pertuzumab with 600 mg trastuzumab) was not enrolled in part 2. Cohort B investigated a co-mixed injection of pertuzumab SC and trastuzumab SC with 1,000 U/mL rHuPH20 to confirm the pertuzumab dose selected in Part 1 of the study. The co-mixed material in Cohort B serves as a surrogate for FDC (described in Example 2), which will be tested in Cohort C.

Non-compartmental and population PK analyses of PK data in Part 2 were conducted:
  to confirm the lack of PK drug-drug interaction (DDI) between pertuzumab and trastuzumab when both were administered co-mixed SC,
  to investigate the impact of 1,000 U/mL rHuPH20 on pertuzumab and trastuzumab PK, and
  to confirm the pertuzumab SC maintenance dose of 600 mg was non-inferior when compared to pertuzumab IV 420 mg (administered to HMVs) in terms of steady state $C_{trough}$ in 20 EBC patients.

Pertuzumab geometric mean concentrations following a co-mixed dose of pertuzumab SC 500 mg, trastuzumab SC 600 mg and rHuPH20 1,000 U/mL to 20 EBC patients in Part 2 Cohort B were compared to pertuzumab geometric mean concentrations following a dose of pertuzumab IV 420 mg to 6 HMVs in Part 1 Cohort 1. As shown in FIG. 22, pertuzumab exposures ($C_{trough}$ and AUC) are similar between 600 mg SC (EBC patients) and 420 mg IV (HMVs).

Figure 23:
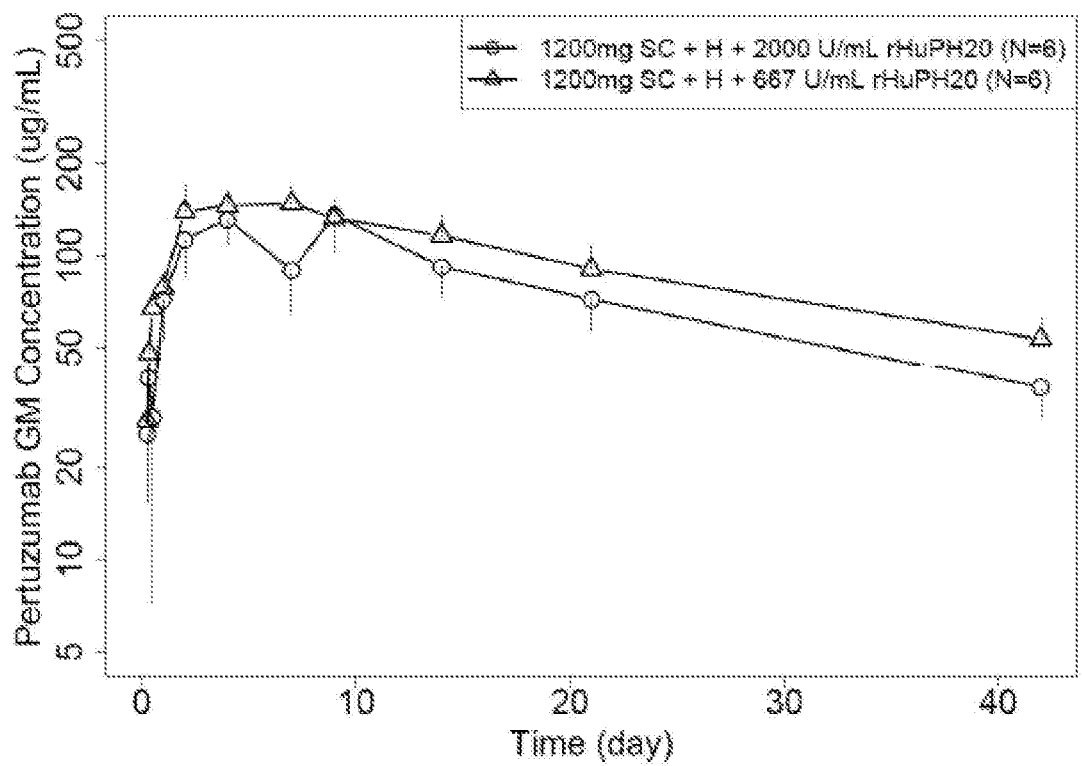

Pertuzumab geometric mean dose-normalized concentrations following a co-mixed dose of pertuzumab SC 600 mg, trastuzumab SC 600 mg and rHuPH20 1,000 U/mL to 20 EBC patients in Part 2 Cohort B were also compared to pertuzumab geometric mean concentrations following a dose of pertuzumab SC 600 mg and rHuPH20 2,000 U/mL to 6 HMVs in Part 1 Cohort 3. As shown in FIG. 23, the pertuzumab PK profiles are very similar between EBC patients (Part 2 Cohort B) and HMVs following a partuzumab SC 600 mg dose (Part 1 Cohort 3).

Comparing pertuzumab and trastuzumab geometric mean dose-normalized concentrations when administered with 667 U/mL, 1,000 U/mL or 2,000 U/mL rHuPH20 can assess the potential impact of the absorption enhancing enzyme rHuPH20 on pertuzumab and trastuzumab PK. As shown in FIG. 24, there was no apparent impact of lowering the rHuPH20 concentration from 2,000 U/mL to 1,000 U/mL or 667 U/mL on the PK of pertuzumab. The comparison of pertuzumab PK data from EBC patients to HNVs further confirms the lack of interaction between pertuzumab and trastuzumab when pertuzumab and trastuzumab are administered co-mixed subcutaneously.

Figure 25:
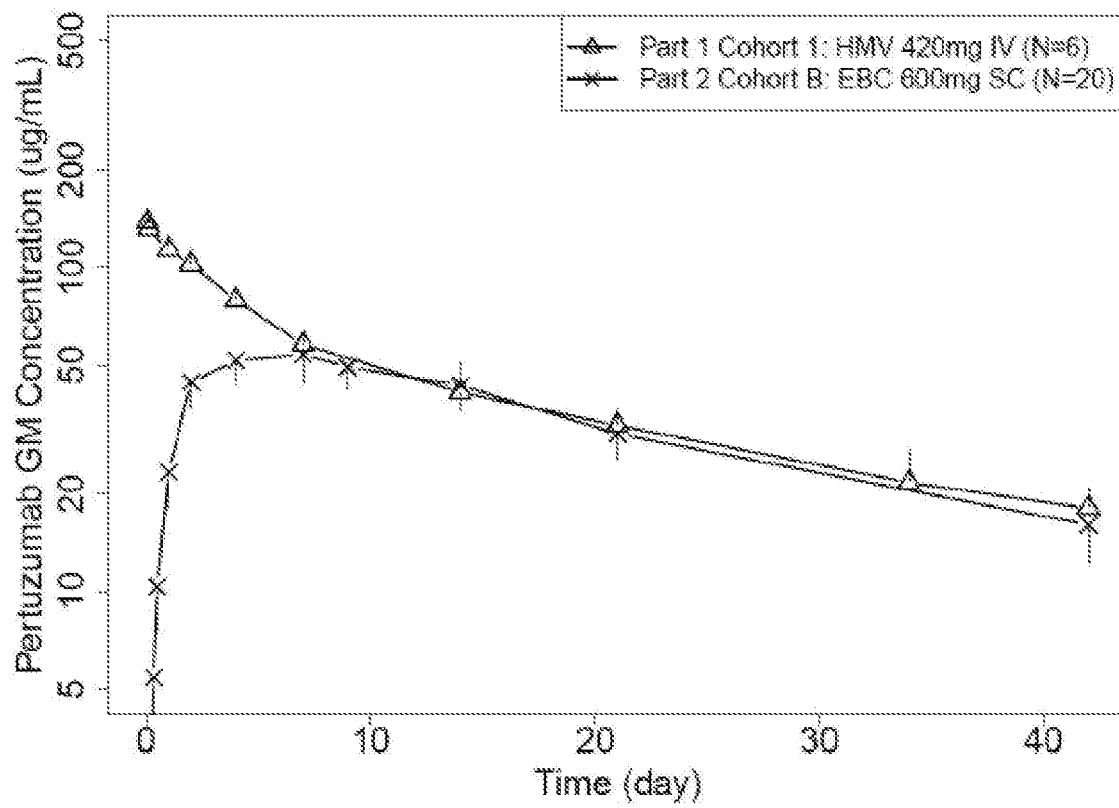
FIG. 25 Geometric Mean Serum Pertuzumab Concentration-Time Profile following Perjeta 600 mg SC and Perjeta 420 mg IV Doses.
Figure 26:
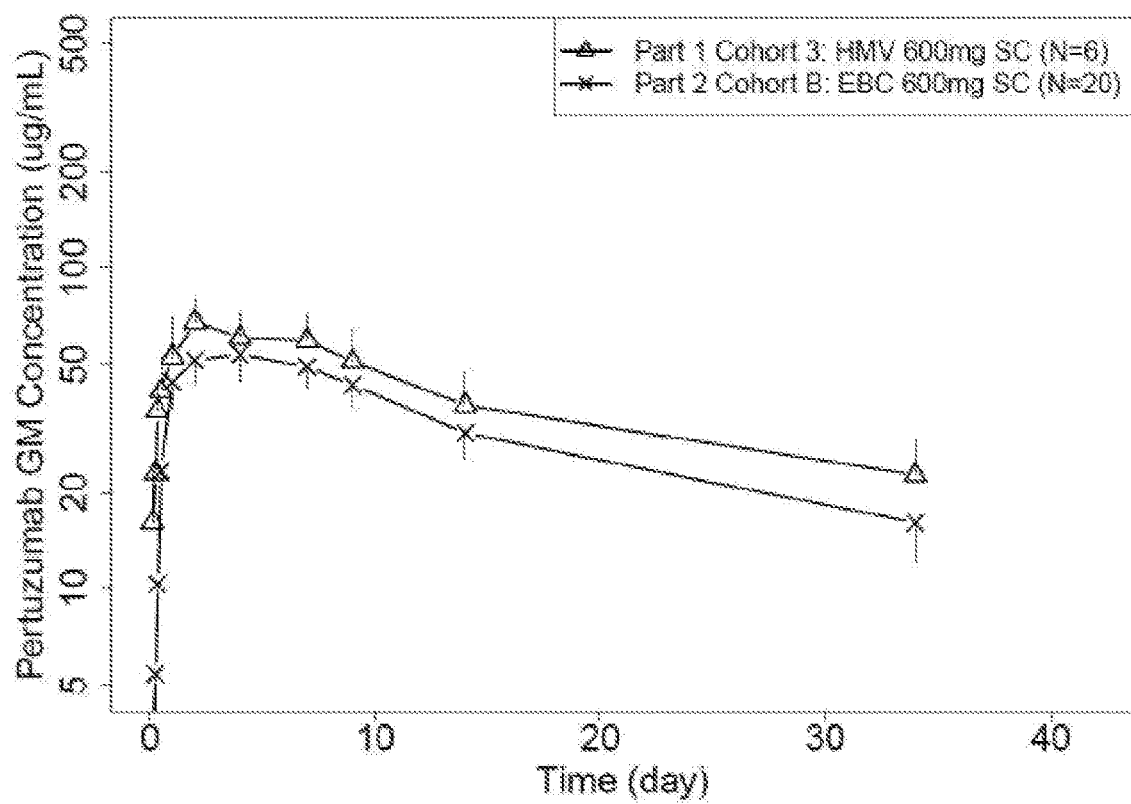
FIG. 26 Geometric Mean Serum Pertuzumab Concentration-Time Profile in HMV or EBC Patients.
Figure 27:
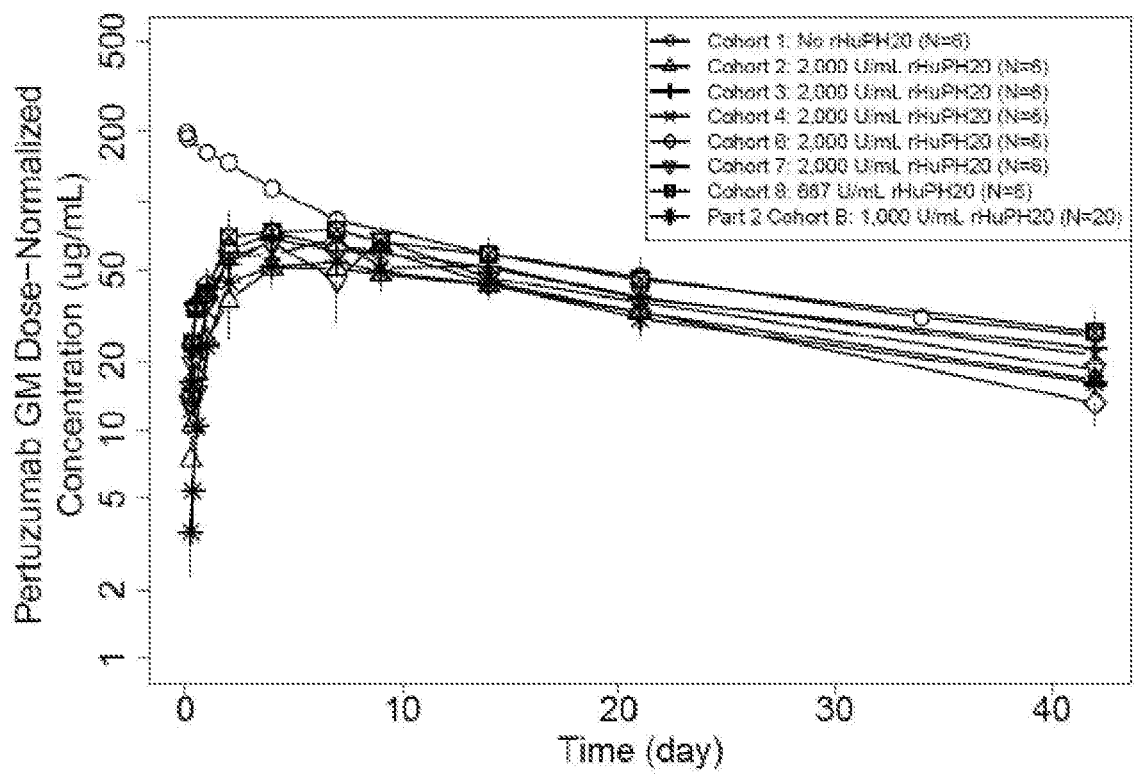
FIG. 27 Geometric Mean Dose-Normalized Serum Pertuzumab Concentration-Time Profile. With 667 U/mL, 1,000 U/mL or 2,000 U/mL rHuPH20.
Figure 28:
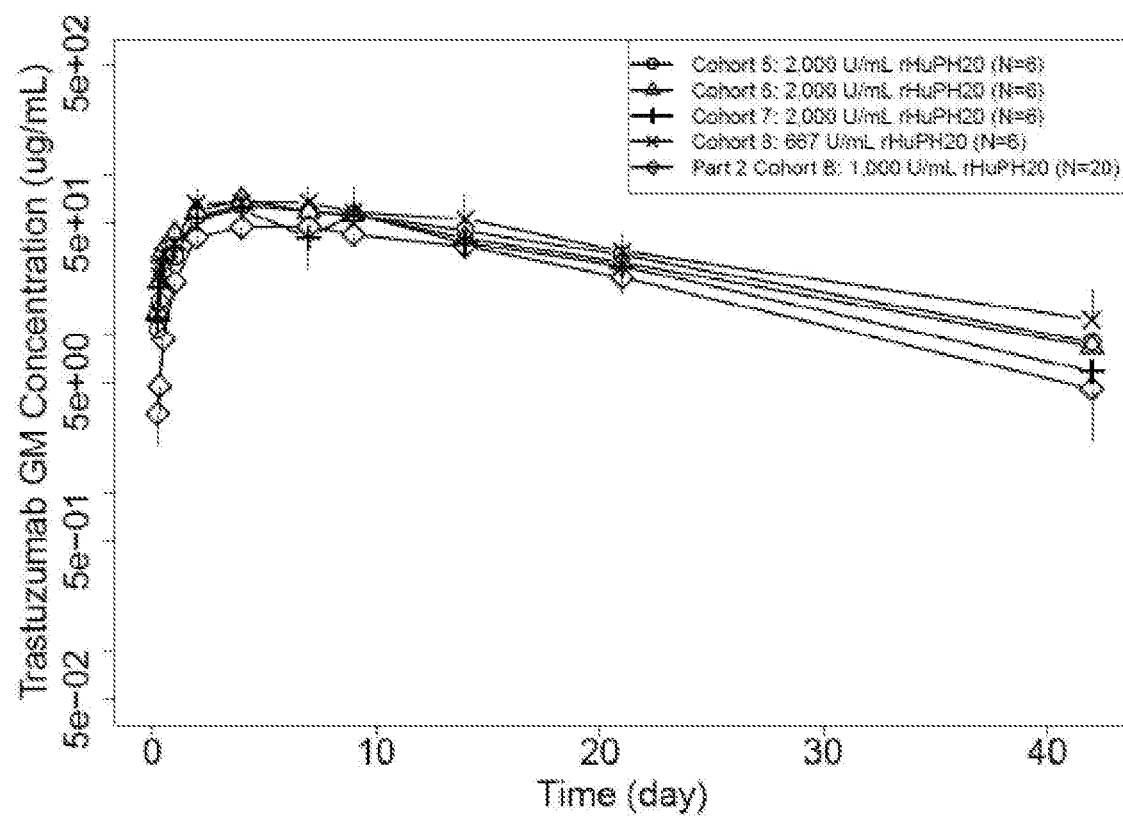
FIG. 28 Geometric Mean Serum Trastuzumab Concentration-Time Profile With 667 U/mL, or 1,000 U/mL, or 2,000 U/mL rHuPH20.

As shown in FIG. 25, there were no apparent differences in trastuzumab PK when administered with 667 U/mL, 2,000 U/mL or 2,000 U/mL rHuPH20. The characterization of pertuzumab PK in Part 2 Cohort B confirmed the results in Part 1 of the study. Part 2 Cohort B indicated that trastuzumab (resulting from simultaneous trastuzumab SC administration) had no apparent impact on pertuzumab PK, and pertuzumab and trastuzumab PK are similar at rhuPH20 concentrations from 2,000 U/mL to 1,000 U/mL.

Observed PK data, model simulations using the popPK model refreshed with additional PK data collected in Part 2 Cohort B and resulting probabilities in Part 2 Cohort B were nearly identical to the data obtained in Part 1. These data were further supported after a second popPK model was built using SC data from Parts 1 and 2 of the current Phase I study and IV data from the historical pertuzumab IV popPK model (Garg et al., Cancer Chemother Pharmacol. 2014; 74:819-829). The addition of a robust pertuzumab IV dataset in patients coupled with the SC data in HMVs confirmed the PK parameter estimates and simulations and provided agreement with selection of a pertuzumab SC loading and maintenance dose of 1200 mg and 600 mg, respectively.

rHuPH20 Pharmacokinetics

Plasma rHuPH20 concentrations w4ere measured at pre-dose and at 0.5 and 24 hours postdose for patients in Cohorts 2-8 of Part 1 and Cohort B of Part 2. A validated sandwich immunoassay using an electroluminescence (ECL) readout, was used to measure the plasma rHuPH20 concentrations. The minimum quantifiable concentration was 0.061444 ng/mL.

Plasma rHuPH20 concentrations were below the limit of quantification for all sampling time points, indicating no quantifiable systemic exposure to the enzyme at the rHuPH20 doses used in this study.

Conclusions

The PK of subcutaneously administered pertuzumab has been consistent with the PK of subcutaneously administered trastuzumab. The tested lowed and higher amounts/concentrations of rHuPH20 showed no impact on the PK of subcutaneously administered pertuzumab. Thus, both of the tested rHuPH20 concentrations (667 U/mL and 1,000 U/mL) are suitable for use in the methods described herein.

Similar pertuzumab and trastuzumab PK were observed when using 2,000-, 1,000-, or 667-U/mL rHUPH20. The safety profiles were comparable in co-mixed cohorts receiving 1,000-, 1,000-. Or 667-U/mL rHuPH20. However, since different concentrations of rHuPH20 were assessed in two groups of populations (HMVs and EBC patients) each with a small number of subjects, a potential impact of a lower concentration (e.g., 1,000 U/mL) on pertuzumab PK and/or safety in these different subject populations cannot be ruled out, and the recommended concentration of rHuPH20 in the FDC (2,000 U/mL) was determined with the totality of other available clinical experience.

Safety Results

Part 1 Safety Data

Figure 12:
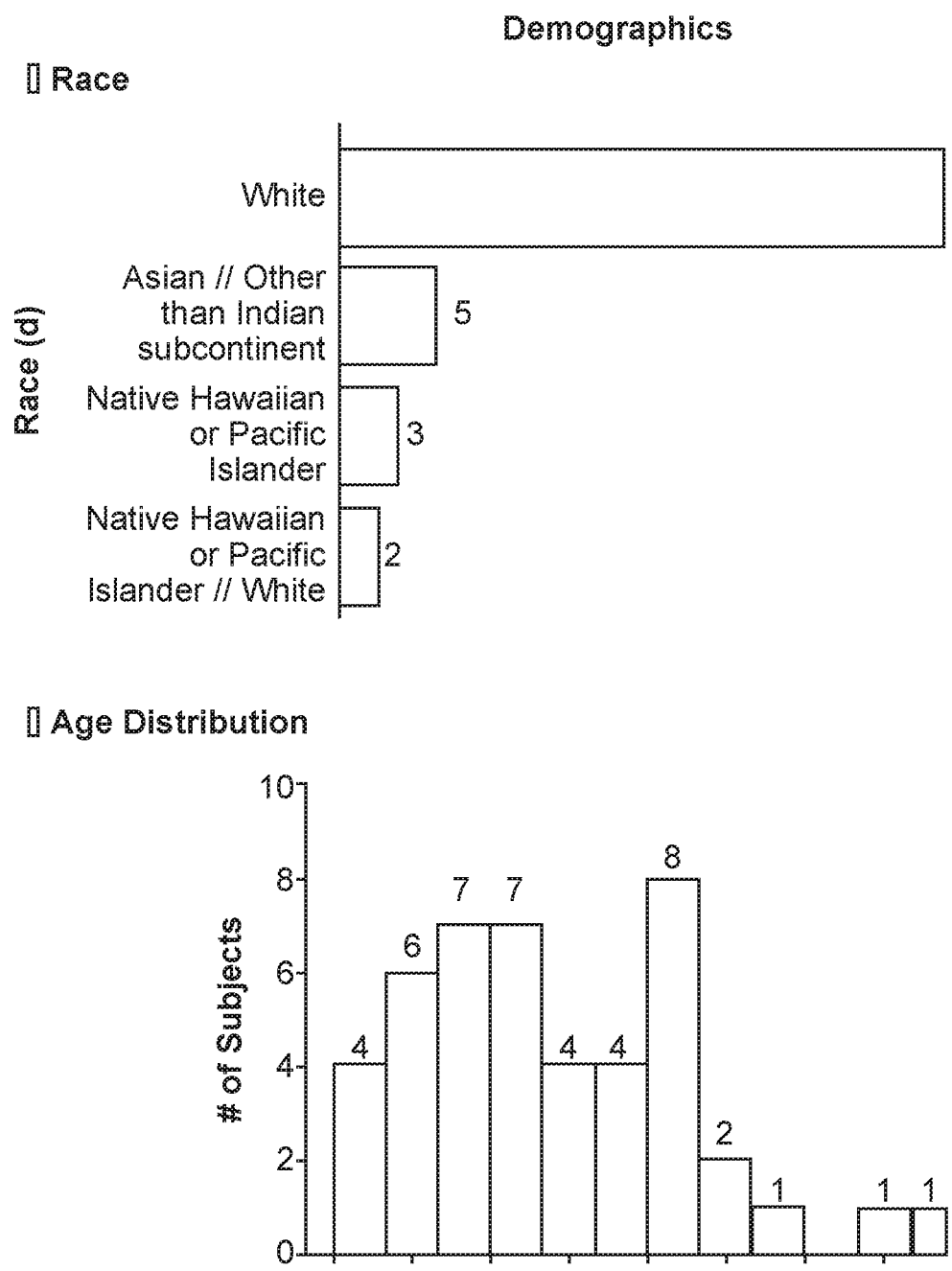
FIG. 12 Demographics and Age Distribution.

The demographics and age distribution of the study population is shown in FIG. 12.

FIG. 13 shows an overview of Adverse Events in Part 1 of the study. The total number of adverse events was 145, and the % of the Grade 1, Grade 2 and ≥Grade 3 adverse events for the various cohorts is listed in parenthesis. The observed one Grade 3 AE of diarrhea on day 32 was an unrelated concurrent illness, a possible viral infection assessed as concurrent upper respiratory tract infection (URTI). There was no Serious Adverse Event (SAE), Adverse Event of Special Interest (AESI), or Adverse Event (AE) leading to discontinuation, or AE leading to death. At the time of evaluation some AEs were ongoing, therefore no final Extreme Grade can be provided.

FIG. 14 shows an overview shows a summary of the Adverse Events in Part 1 of the study, listing the number of subjects for each cohost and adverse event.

FIG. 15 is a tabulation of the most common Adverse Events (all grades) with an overall incidence of ≥5% in the study No. of subjects for Cohorts 18.

FIG. 16 shows the EGF related toxicities, i.e. diarrhea, mucositis and EGFR associated rash.

FIG. 17 summarizes the injection related reactions and injection site reactions, including systemic and local reactions, for Cohorts 1 to 8. There was one injections site reaction in Cohort 7 (1200 mg pertuzumab (P) SC+600 mg trastuzumab (H) SC with rHuPH20. The symptoms were discomfort, pain, tightness and numbness at the injection site. The systemic injection Related Reactions included fever, chills, nausea, stiffness, lightheadedness, skin sensitivity, photophobia, temperature fluctuation, and headache.

FIG. 18 shows the results of LVEF—Echo assessments in cohorts 1-8. In cohort 3 (600 mg pertuzumab (P) SC), one Healthy Male Volunteer (HMV) has a drop of >10% from 67% at Baseline to 56% at Day 22. Follow up Ejection Fraction (EF) at Day 85 was 60%. The cardiologist confirmed no evidence of cardiotoxicity. The drop is believed to be due to variability of the imaging method.

Common Adverse Events

In Part 1 (Cohorts 1-8), a total of 148 AEs were reported in 44 out of 48 (91.7%) healthy kale volunteers (HMVs). The majority of AEs were reported to be of low intensity (Grade 1 or 2). The most common SOC was infections and infestations, with 22 (45.8%) HMVs experiencing a total of 33 AEs in this category, of which a majority of events were considered not related to study drug by the investigator. The most commonly observed AEs (by PT) across different cohorts were: upper respiratory tract infection (13 HMVs [27.1%]), headache (9 HMVs [18.8%]), drug eruption (9 HMVs [18.8%]), and diarrhea (9 HMVs [18.8%]). Among these common AEs, study drug related AEs (assessed by the investigator) were reported in 4 (8.3%), 8 (18.8%), and 7 (14.6%) HMVs, respectively. All AEs in Part 1 resolved by the end of Part 1.

In Cohort 1 (control), in which HMVs received a single IV injection of 420 mg pertuzumab, commonly observed AEs (by patient) included: diarrhea (3 out of 6 HMVs [50%]), upper respiratory tract infection (2 HMVs [33.3%]), and angular cheilitis (2 HMVs [33.3%]).

In Cohorts 2-4, in which HMVs received a single SC injection of pertuzumab at 400 mg, 600 mg, and 1200 mg, respectively, the most commonly observed AEs (by patient) were respiratory tract infection, rash, and diarrhea, each occurred in 4 out of 18 (22.2%) HMVs.

In Cohort 5 (control), in which HMVs received a single SC injection of 600 mg trastuzumab, the most commonly observed AEs (by patient) was pain in extremity (at buttocks and upper thighs, not at injection site) (2 out of 6 HMVs [33.3%]). All other AEs were reported in 1 HMV only.

In Cohorts 6-8, in which HMVs received a SC injection of 600 mg trastuzumab co-mixed with pertuzumab at 400 mg, 1200 mg (with 2000 U/mL rHuPH20), and 1200 mg (with 667 U/mL rHuPH20), respectively, the incidence of AEs was similar to that in HMVs who received pertuzumab alone (Cohorts 2-4). The most commonly observed AEs were upper respiratory tract infection and drug eruption, each occurring in 7 out of 18 (38.9%) HMVs. Other common AEs reported in at least 20% of HMVs were angular cheilitis (4 HMVs [22.2%]) and headache (4 HMVs [22.2%]).

The incidence of overall AEs was similar between HMVs receiving a concentration of 2.000 U/mL rHuPH20 (Cohort 7) and those receiving a concentration of 667 U/mL rHuPH20 (Cohort 8) as part of a co-mixed injection of pertuzumab and trastuzumab.

Regarding additional safety objectives there were:
No significant overall changes in blood pressure (BP), heart rate (HR) or in beat-to-beat intervals (RR)
Four subjects had a rise in temperature post-dose on Day 1 associated with Injection Related Reaction
No clinically significant ECG changes were reported
Regarding laboratory changes there was:
No significant AE laboratory abnormality
One subject had Grade 4 Urate increase (Day 22), which was confirmed by site as Not Clinically Significant and probably exercise related, the result was normal at Day 85.
Four subjects had Grade 3 Urate increase, which were all confirmed by site as Not Clinically Significant and Grade 1.

Part 2 Safety Data

In Part 2, all 20 [1005] female EBC patients received a co-mixed SC injection of 600 mg pertuzumab and 600 mg trastuzumab (with 1.000 U/mL rHuPH20). All patients experienced at least one AE, with a total of 102 AEs reported by the time of clinical trial cut-off. The majority of AEs were reported of low intensity (Grade 1 or 2).

The SOCs in which the most common AEs (reported in 50% patients) occurred included the following:
Nervous System Disorders (14 patients [70%])
Gastrointestinal Disorders (10 [50%]), study drug related AEs (10 [50%])
Musculoskeletal and Connective Tissue Disorders (10 [50%])

The most commonly observed AEs (by patient) reported in at least 20% of patients were: headache (13 patients [65%]), myalgia (7 patients [35%]), diarrhea (6 patients [30%]), injection site reaction (6 patients [30%]), and nausea (4 patients [20%]). Among these common AEs, study drug related AEs (assessed by the investigator) were reported in 9 (45%), 6 (30%), 4 (20%), 6 (30%), and 1 (5%) patients, respectively.

Both Cohort B (EBC patients) or Part 2 and Cohorts 6-8 (HMVs) of Part 1 received a co-mixed injection of pertuzumab and trastuzumab, and the type of AEs that were reported (by patient) with pertuzumab SC and trastuzumab SC in EBC patients are consistent with known risks associated with the combination therapy. Injection site reaction, all of Grade 1 or 2, occurred with higher frequency in EBC patients compared to HMVs (6 [30%] vs. 1 [5.6%]).

Conclusions

In Part 1, all adverse events (AEs) in subcutaneously dose cohorts were Grade 1 or Grade 2.

There were no Serious Adverse Events (SAEs), Adverse Events of Special Interest (AESI(, or >G3 AEs leading to discontinuation, or fatal events.

No significant cardiac events were observed.

There were higher numbers of AEs in most P SC and P+H SC cohorts compared to control cohort (P IV, H SC), however, no consistent pattern was observed with increasing dose or addition trastuzumab (H).

The most common AEs (occurring in >5% of subjects) were upper respiratory tract infection, diarrhea, headache and drug eruption. There was no difference between Cohorts 7 and 8 (with lower rHuPH20 concentration).

Four Injection Related Reactions (1 in H SC) and one Injection Site Reaction (Cohort 7) were observed. All reactions were Grade 1/2 and comparable to the subcutaneously administered trastuzumab (H SC) profile.

In conclusion, the safety profile of subcutaneously administered pertuzumab (P), and the results in general were consistent with the known safety profile of intravenously administered pertuzumab and subcutaneously administered trastuzumab. Accordingly, it was safe to continue the study and move to Part 2.

Pertuzumab SC, given as a loading dose of 1200 mg and maintenance dose of 600 mg provides similar $C_{trough}$ and AUC as pertuzumab IV 840 mg and 420 mg, respectively, as determined in HMVs. Pertuzumab SC 600 mg dose in EBC patients provides similar $C_{trough}$ and AUC to the 420 mg IV and 600 mg SC cohorts in HMVs in Part 1 and ose proportionality through PK linearity confirms a pertuzumab SC 1200 loading dose. Therefore, pertuzumab SC doses (1200 mg loading, 600 mg maintenance) are confirmed in EBC patients.

In general, the safety profile of pertuzumab SC is consistent with the known safety profile of pertuzumab IV, and is well tolerated when given in combination with trastuzumab SC. There were no new safety signals identified. The majority of HMVs in Part 1 and all EBC patients in Part 2 Cohort B experienced at least one AE. There were 2 Grade 3 AEs in Part 1 and 1 Grade 3 AE in Part 2 during the study. The remainder of the AEs were of low intensity (Grade 1 or 2). There were no SAEs, deaths, or AEs leading to withdrawals during the study. Following a co-mixed SC injection of pertuzumab and trastuzumab, female EBC patients experienced higher incidences of injection site reactions compared to HMVs.

In view of the PK and safety findings in the current study (Parts 1 and 2), the safety, tolerability and PK results of this Phase I study support the continuation of the study and enrollment of Cohort C to receive pertuzumab+trastuzumab fixed-dose co-formulation (FDC).

EXAMPLE 2

Stable Subcutaneous Fixed-Dose Co-Formulations (SC FDC) of Pertuzumab and Trastuzumab Stable fixed-dose co-formulations (FDC) of pertuzumab and trastuzumab were developed for subcutaneous (SC) administration.

The co-formulation studies used the pertuzumab and trastuzumab SC Drug Substance (DS) compositions and rHuPH20 composition shown in FIG. 19.

The amount (%) of high molecular weight species (HMWS) in various subcutaneous pertuzumab and trastuzumab formulations, and pertuzumab/trastuzumab co-formulations containing trehalose and/or sucrose as stabilizer at 5° C. and 25° C. are shown in FIG. 23.

The following SC FDS loading and maintenance formulations were found to be stable and suitable for subcutaneous administration of a single co-formulation of pertuzumab and trastuzumab to human patients:

Loading Dose
Pertuzumab
Dose: 1,200 mg
Concentration: 80 mg/mL
Trastuzumab
Dose: 600 mg
Concentration: 40 mg/mL
rHuPH20
Concentration: 1,000 U/mL or 2,000 U/mL
pH: 5.5
20 mM L-Histidine/HCl
Trehalose: 70 mM
Sucrose: 133 mM
Polysorbate 20 (PS20): 0.04%; 0.4 mg/mL
10 mM Methionine
Nominal fill volume 15 mL
Vial: 20 mL/20 mm
Maintenance Dose:
Pertuzumab
Dose: 600 mg
Concentration: 60 mg/mL
Trastuzumab
Dose: 600 mg
Concentration: 60 mg/mL
rHuPH20
Concentration: 1,000 U/mL or 2,000 U/mL
pH: 5.5
20 mM L-Histidine/HCl
Trehalose: 105 mM
Sucrose: 100 mM
Polysorbate PS20: 0.04%; 0.4 mg/mL
10 mM methionine
Nominal fill volume: 10 mL
Vial: 15 mL/20 mm
Pertuzumab Drug Substance Stability
Scratch & Sprinkle Test Protein aggregation can occur due to excipient (sugar) crystallization in the frozen state under storage conditions of the drug substance. In the scratch and sprinkle test, vials of drug substance are frozen and some sugar (trehalose or sucrose) is added to top of frozen formulation, then scratched with a metal spatula to accelerate any potential sugar crystallization in the formulation while frozen. At predetermined time points the formulations are thawed and analyzed by Size Exclusion Chromatography (SEC).

Figure 29:
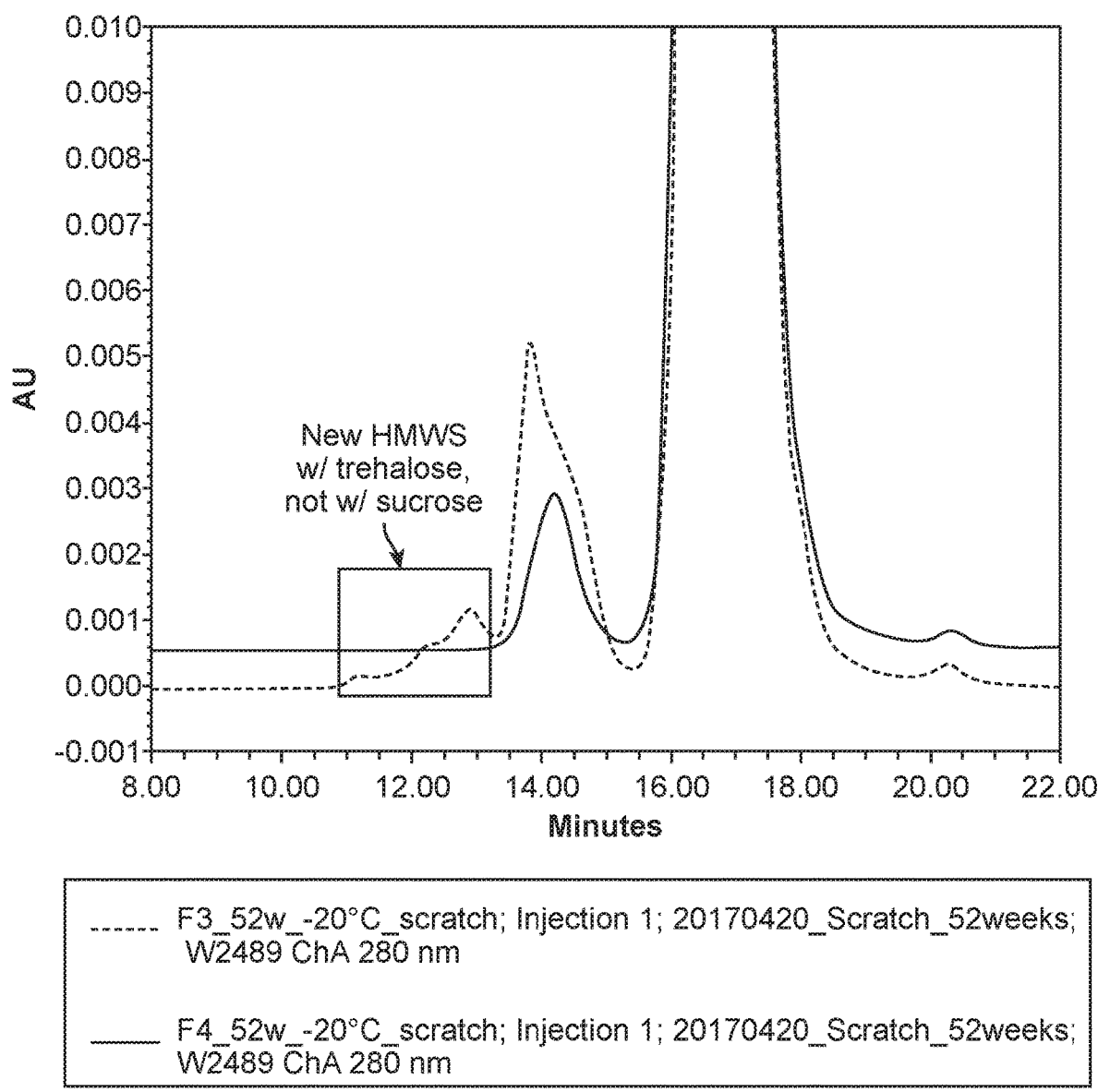
FIG. 29 Pertuzumab Drug Substance Stability Scratch & Sprinkle Test: SEC Data

The SEC data shown in FIG. 29 demonstrate that sucrose is superior excipient for pertuzumab drug substance stored at −20° C.

The effect of formulation differences in the following pertuzumab-trastuzumab fixed-dose combinations (FDCs) on turbidity and amount of high molecular weight species (HMWS) was tested.

| | Code | | | |
|---|---|---|---|---|
| | F1 | F2 | F3 | F4 |
| Fixed Dose Combination | Maintenance Dose | Maintenance Dose | Loading Dose | Loading Dose |
| Buffer (20 mM) | His-HCl pH 5.5 | His-HCl pH 5.5 | His-HCl pH 5.5 | His-HCl pH 5.5 |
| Trastuzumab (mg/mL) | 60 | 60 | 40 | 40 |
| Pertuzumab (mg/mL) | 60 | 60 | 80 | 80 |
| rHuPH20 (EU/mL) | 2000 | 2000 | 2000 | 2000 |
| PS20 (%) | 0.04 | 0.04 | 0.04 | 0.04 |
| Met (mM) | 10 | 10 | 10 | 10 |
| Sucrose (mM) | 100 | — | 133 | — |
| Trehalose (mM) | 105 | — | 70 | — |
| NaCl (mM) | — | 130 | — | 130 |

Figure 30:
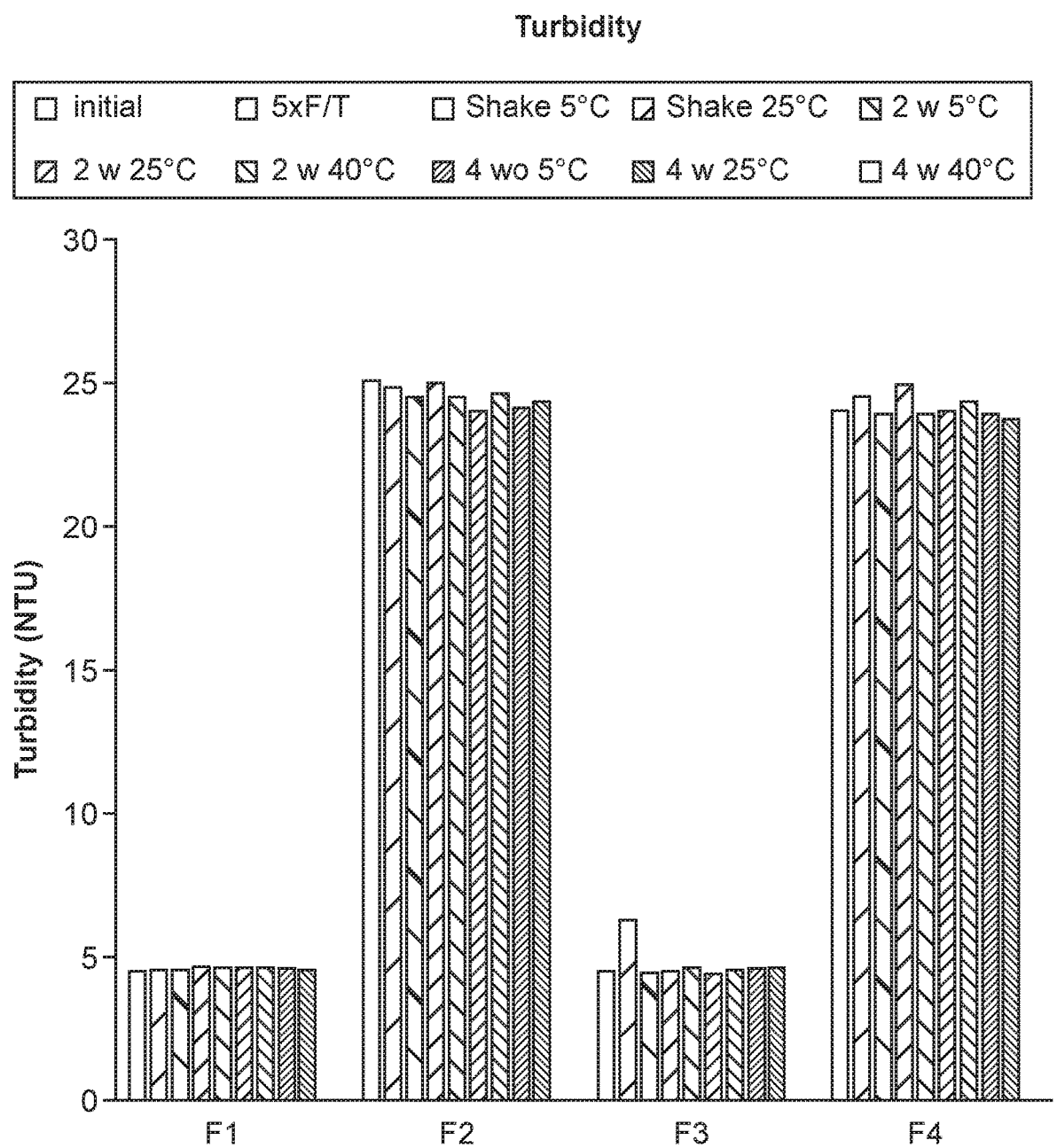
FIG. 30 FDC Formulation Differences—Turbidity
Figure 31:
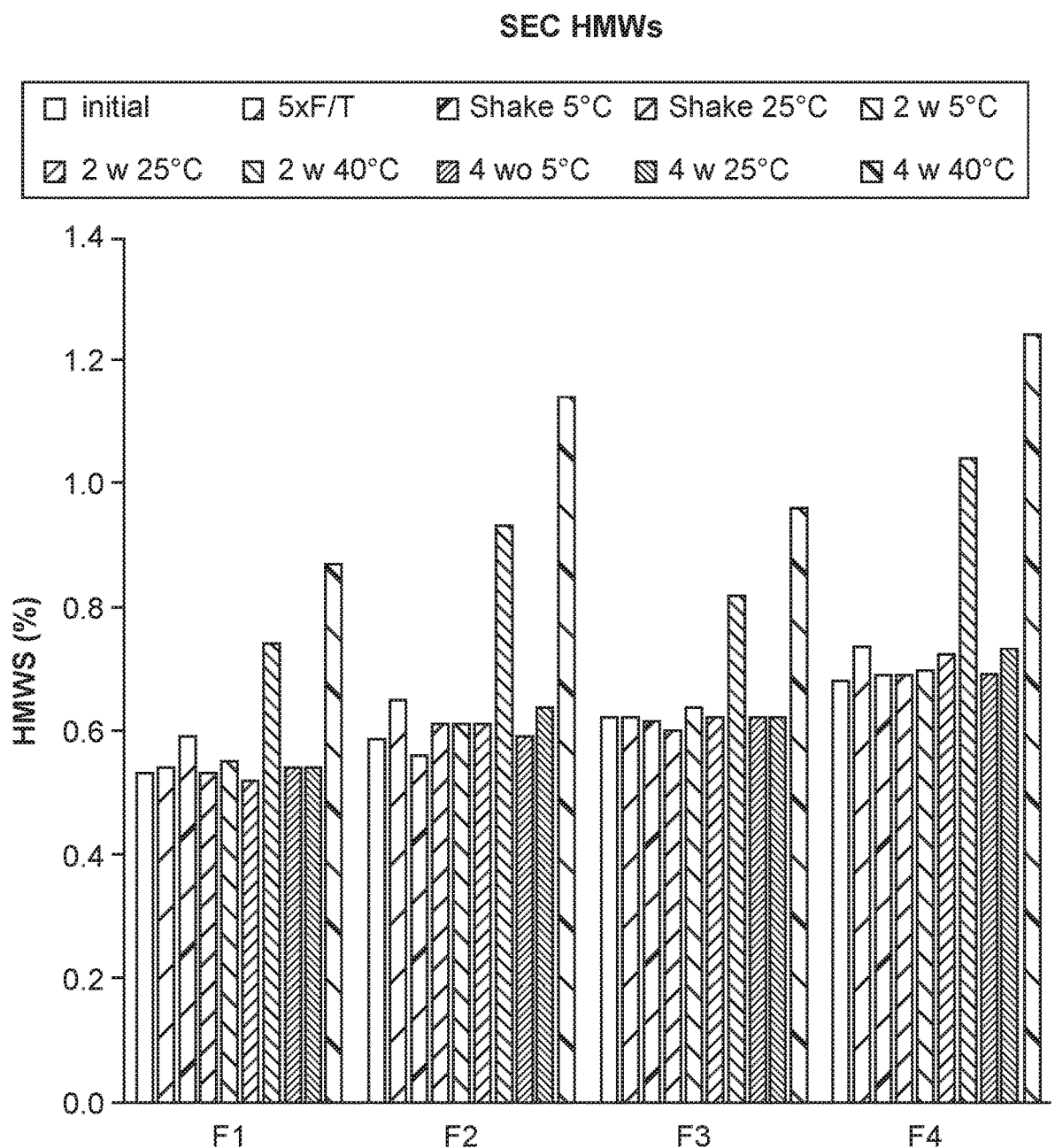
FIG. 31 FDC Formulation Differences—SEC/HMWS

The data shown in FIG. 30 demonstrate that NaCl as excipient results in high turbidity in the pertuzumab-trastuzumab SC fixed-dose combination (FDC). Similarly, the data shown in FIG. 31 demonstrate that NaCl as an excipient results in higher amounts of high molecular weight species (HMWs). Accordingly, sucrose and trehalose are superior excipients for the FDC.

While certain embodiments of the present invention have been shown and described herein, it will be understood by those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for treating cancer comprising subcutaneously administering to a human subject with a HER2 positive cancer fixed doses of a HER2 antibody comprising the light chain variable region and heavy chain variable region amino acid sequences in SEQ ID Nos. 7 and 8, respectively, the method comprising subcutaneously administering to the human subject the HER2 antibody at a fixed loading dose of 1200 mg followed by at least one fixed maintenance dose of 600 mg.

2. The method of claim 1, wherein the HER2 antibody is pertuzumab.

3. The method of claim 1, wherein the administration of the loading dose is followed by administration of multiple maintenance doses.

4. The method of claim 2, wherein the first maintenance dose of pertuzumab is administered to the human subject approximately two weeks or approximately three weeks after administration of the loading dose of pertuzumab.

5. The method of claim 2, wherein fixed maintenance doses of pertuzumab are administered to the human subject approximately every 2 weeks or approximately every 3 weeks.

6. The method of claim 5, wherein the fixed maintenance doses of pertuzumab are administered approximately every 3 weeks.

7. The method of claim 1, wherein the HER2 positive cancer is selected from the group consisting of breast cancer, peritoneal cancer, fallopian tube cancer, lung cancer, colorectal cancer, biliary cancer, and bladder cancer.

8. The method of claim 1, wherein the cancer is breast cancer.

9. The method of claim 8, wherein the breast cancer is early breast cancer (EBC) or metastatic breast cancer (MBC).

10. The method of claim 1, comprising administering a second therapeutic agent to the patient.

11. The method of claim 10, wherein the second therapeutic agent is a different HER2 antibody.

12. The method of claim 11, wherein the second therapeutic agent is trastuzumab.

13. The method of claim 1, wherein the fixed doses of pertuzumab are administered subcutaneously in combination with subcutaneous administration of trastuzumab.

14. The method of claim 13, wherein each of the fixed doses of pertuzumab and the trastuzumab are co-administered subcutaneously as two separate subcutaneous injections.

15. The method of claim 13, wherein each of the fixed doses of pertuzumab is co-mixed with fixed dose trastuzumab, and administered as a single subcutaneous injection.

16. The method of claim 13, wherein each of the fixed doses of pertuzumab and fixed dose trastuzumab are administered as a single co-formulation for subcutaneous administration.

17. The method of claim 16, wherein a loading dose co-formulation comprises 1200 mg pertuzumab and 600 mg trastuzumab, and a maintenance dose co-formulation comprises 600 mg pertuzumab and 600 mg trastuzumab.

18. The method of claim 10, wherein the second therapeutic agent is a chemotherapeutic agent.

19. The method of claim 18, wherein the chemotherapeutic agent is selected from the group consisting of taxanes and anthracylines.

20. The method of claim 19, wherein the taxane is paclitaxel or docetaxel.

21. The method of claim 19, wherein the anthracycline comprises daunorubicin, doxorubicin, or epirubicin.

22. The method of claim 17, wherein the co-formulations further comprise recombinant human hyaluronidase (rHuPH20) at a concentration of between about 150 U/ml and 16,000 U/ml.

23. The method of claim 22, wherein the co-formulations comprise 1,000 U/ml or 2,000 U/ml rHuPH20.

24. The method of claim 17, wherein the loading dose co-formulation comprises 1200 mg pertuzumab at a concentration of 80 mg/ml, 600 mg trastuzumab at a concentration of 40 mg/ml, 2,000 U/mL recombinant human hyaluronidase (rHuPH20), 20 mM Histidine-HCl pH 5.5, 70 mM trehalose, 133 mM sucrose, 0.04% polysorbate 20, 10 mM methionine, and sterile water for injection.

25. The method of claim 17, wherein the maintenance dose co-formulation comprises 600 mg pertuzumab at a concentration of 60 mg/ml, 600 mg trastuzumab at a concentration of 60 mg/ml, 2,000 U/mL recombinant human hyaluronidase (rHuPH20), 20 mM Histidine-HCl pH 5.5, 105 mM trehalose, 100 mM sucrose, 0.04% polysorbate 20, 10 mM methionine, and sterile water for injection.

26. A method for treating HER2 positive cancer in a human patient comprising subcutaneously administering to the patient a fixed loading dose of 1200 mg of pertuzumab followed by fixed maintenance doses of 600 mg of pertuzumab.

27. A method for treating HER2 positive cancer in a human patient comprising subcutaneously administering to the patient a fixed loading dose of 1200 mg of pertuzumab in combination with a fixed dose of 600 mg of trastuzumab, followed every three weeks by a fixed maintenance dose of 600 mg pertuzumab in combination with a fixed dose of 600 mg of trastuzumab.

28. A method for treating HER2 positive cancer in a human patient comprising subcutaneously administering to the patient a co-formulation comprising 1200 mg of pertuzumab and 600 mg of trastuzumab followed every three weeks by a co-formulation comprising 600 pertuzumab and 600 mg trastuzumab.

* * * * *

SEQUENCE LISTING

<160> NUMBER OF SEQ ID NOS: 22

<210> SEQ ID NO 1
<211> LENGTH: 195
<212> TYPE: PRT
<213> ORGANISM: Homo sapiens

<400> SEQUENCE: 1

Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
            20                  25                  30

Val Val Gln Gly Asn Leu Glu Leu Thr Tyr Leu Pro Thr Asn Ala Ser
        35                  40                  45

Leu Ser Phe Leu Gln Asp Ile Gln Glu Val Gln Gly Tyr Val Leu Ile
    50                  55                  60

Ala His Asn Gln Val Arg Gln Val Pro Leu Gln Arg Leu Arg Ile Val
65                  70                  75                  80

Arg Gly Thr Gln Leu Phe Glu Asp Asn Tyr Ala Leu Ala Val Leu Asp
                85                  90                  95

Asn Gly Asp Pro Leu Asn Asn Thr Thr Pro Val Thr Gly Ala Ser Pro
            100                 105                 110

Gly Gly Leu Arg Glu Leu Gln Leu Arg Ser Leu Thr Glu Ile Leu Lys
        115                 120                 125

Gly Gly Val Leu Ile Gln Arg Asn Pro Gln Leu Cys Tyr Gln Asp Thr
    130                 135                 140

Ile Leu Trp Lys Asp Ile Phe His Lys Asn Asn Gln Leu Ala Leu Thr
145                 150                 155                 160

Leu Ile Asp Thr Asn Arg Ser Arg Ala Cys His Pro Cys Ser Pro Met
                165                 170                 175

Cys Lys Gly Ser Arg Cys Trp Gly Glu Ser Ser Glu Asp Cys Gln Ser
            180                 185                 190

Leu Thr Arg
        195

<210> SEQ ID NO 2
<211> LENGTH: 124
<212> TYPE: PRT
<213> ORGANISM: Homo sapiens

<400> SEQUENCE: 2

Thr Val Cys Ala Gly Gly Cys Ala Arg Cys Lys Gly Pro Leu Pro Thr
1               5                   10                  15

Asp Cys Cys His Glu Gln Cys Ala Ala Gly Cys Thr Gly Pro Lys His
            20                  25                  30

Ser Asp Cys Leu Ala Cys Leu His Phe Asn His Ser Gly Ile Cys Glu
        35                  40                  45

Leu His Cys Pro Ala Leu Val Thr Tyr Asn Thr Asp Thr Phe Glu Ser
    50                  55                  60

Met Pro Asn Pro Glu Gly Arg Tyr Thr Phe Gly Ala Ser Cys Val Thr
65                  70                  75                  80

Ala Cys Pro Tyr Asn Tyr Leu Ser Thr Asp Val Gly Ser Cys Thr Leu
                85                  90                  95

Val Cys Pro Leu His Asn Gln Glu Val Thr Ala Glu Asp Gly Thr Gln
            100                 105                 110

Arg Cys Glu Lys Cys Ser Lys Pro Cys Ala Arg Val
        115                 120

<210> SEQ ID NO 3
<211> LENGTH: 169
<212> TYPE: PRT
<213> ORGANISM: Homo sapiens

<400> SEQUENCE: 3

Cys Tyr Gly Leu Gly Met Glu His Leu Arg Glu Val Arg Ala Val Thr
1               5                   10                  15

Ser Ala Asn Ile Gln Glu Phe Ala Gly Cys Lys Lys Ile Phe Gly Ser
            20                  25                  30

Leu Ala Phe Leu Pro Glu Ser Phe Asp Gly Asp Pro Ala Ser Asn Thr
        35                  40                  45

Ala Pro Leu Gln Pro Glu Gln Leu Gln Val Phe Glu Thr Leu Glu Glu
    50                  55                  60

Ile Thr Gly Tyr Leu Tyr Ile Ser Ala Trp Pro Asp Ser Leu Pro Asp
65                  70                  75                  80

Leu Ser Val Phe Gln Asn Leu Gln Val Ile Arg Gly Arg Ile Leu His
                85                  90                  95

Asn Gly Ala Tyr Ser Leu Thr Leu Gln Gly Leu Gly Ile Ser Trp Leu
            100                 105                 110

Gly Leu Arg Ser Leu Arg Glu Leu Gly Ser Gly Leu Ala Leu Ile His
        115                 120                 125

His Asn Thr His Leu Cys Phe Val His Thr Val Pro Trp Asp Gln Leu
    130                 135                 140

Phe Arg Asn Pro His Gln Ala Leu Leu His Thr Ala Asn Arg Pro Glu
145                 150                 155                 160

Asp Glu Cys Val Gly Glu Gly Leu Ala
                165

<210> SEQ ID NO 4
<211> LENGTH: 142
<212> TYPE: PRT
<213> ORGANISM: Homo sapiens

```
<400> SEQUENCE: 4

Cys His Gln Leu Cys Ala Arg Gly His Cys Trp Gly Pro Gly Pro Thr
1               5                   10                  15

Gln Cys Val Asn Cys Ser Gln Phe Leu Arg Gly Gln Glu Cys Val Glu
            20                  25                  30

Glu Cys Arg Val Leu Gln Gly Leu Pro Arg Glu Tyr Val Asn Ala Arg
        35                  40                  45

His Cys Leu Pro Cys His Pro Glu Cys Gln Pro Gln Asn Gly Ser Val
    50                  55                  60

Thr Cys Phe Gly Pro Glu Ala Asp Gln Cys Val Ala Cys Ala His Tyr
65                  70                  75                  80

Lys Asp Pro Pro Phe Cys Val Ala Arg Cys Pro Ser Gly Val Lys Pro
                85                  90                  95

Asp Leu Ser Tyr Met Pro Ile Trp Lys Phe Pro Asp Glu Glu Gly Ala
            100                 105                 110

Cys Gln Pro Cys Pro Ile Asn Cys Thr His Ser Cys Val Asp Leu Asp
        115                 120                 125

Asp Lys Gly Cys Pro Ala Glu Gln Arg Ala Ser Pro Leu Thr
    130                 135                 140

<210> SEQ ID NO 5
<211> LENGTH: 107
<212> TYPE: PRT
<213> ORGANISM: Mus musculus

<400> SEQUENCE: 5

Asp Thr Val Met Thr Gln Ser His Lys Ile Met Ser Thr Ser Val Gly
1               5                   10                  15

Asp Arg Val Ser Ile Thr Cys Lys Ala Ser Gln Asp Val Ser Ile Gly
            20                  25                  30

Val Ala Trp Tyr Gln Gln Arg Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln Tyr Tyr Ile Tyr Pro Tyr
                85                  90                  95

Thr Phe Gly Gly Gly Thr Lys Leu Glu Ile Lys
            100                 105

<210> SEQ ID NO 6
<211> LENGTH: 119
<212> TYPE: PRT
<213> ORGANISM: Mus musculus

<400> SEQUENCE: 6

Glu Val Gln Leu Gln Gln Ser Gly Pro Glu Leu Val Lys Pro Gly Thr
1               5                   10                  15

Ser Val Lys Ile Ser Cys Lys Ala Ser Gly Phe Thr Phe Thr Asp Tyr
            20                  25                  30

Thr Met Asp Trp Val Lys Gln Ser His Gly Lys Ser Leu Glu Trp Ile
        35                  40                  45

Gly Asp Val Asn Pro Asn Ser Gly Gly Ser Ile Tyr Asn Gln Arg Phe
    50                  55                  60
```

```
Lys Gly Lys Ala Ser Leu Thr Val Asp Arg Ser Arg Ile Val Tyr
 65                  70                  75                  80

Met Glu Leu Arg Ser Leu Thr Phe Glu Asp Thr Ala Val Tyr Tyr Cys
                 85                  90                  95

Ala Arg Asn Leu Gly Pro Ser Phe Tyr Phe Asp Tyr Trp Gly Gln Gly
            100                 105                 110

Thr Thr Leu Thr Val Ser Ser
            115

<210> SEQ ID NO 7
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Asp Ile Gln Met Thr Gln Ser Pro Ser Ser Leu Ser Ala Ser Val Gly
  1               5                  10                  15

Asp Arg Val Thr Ile Thr Cys Lys Ala Ser Gln Asp Val Ser Ile Gly
                 20                  25                  30

Val Ala Trp Tyr Gln Gln Lys Pro Gly Lys Ala Pro Lys Leu Leu Ile
             35                  40                  45

Tyr Ser Ala Ser Tyr Arg Tyr Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Ile Tyr Pro Tyr
                 85                  90                  95

Thr Phe Gly Gln Gly Thr Lys Val Glu Ile Lys
            100                 105

<210> SEQ ID NO 8
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Thr Asp Tyr
                 20                  25                  30

Thr Met Asp Trp Val Arg Gln Ala Pro Gly Lys Gly Leu Glu Trp Val
             35                  40                  45

Ala Asp Val Asn Pro Asn Ser Gly Gly Ser Ile Tyr Asn Gln Arg Phe
 50                  55                  60

Lys Gly Arg Phe Thr Leu Ser Val Asp Arg Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asn Leu Gly Pro Ser Phe Tyr Phe Asp Tyr Trp Gly Gln Gly
            100                 105                 110

Thr Leu Val Thr Val Ser Ser
            115
```

-continued

<210> SEQ ID NO 9
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Leu Pro Trp
                85                  90                  95

Thr Phe Gly Gln Gly Thr Lys Val Glu Ile Lys
            100                 105

<210> SEQ ID NO 10
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Val Ile Ser Gly Asp Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Val Gly Tyr Ser Leu Tyr Asp Tyr Trp Gly Gln Gly
            100                 105                 110

Thr Leu Val Thr Val Ser Ser
        115

<210> SEQ ID NO 11
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Asp Ile Gln Met Thr Gln Ser Pro Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 12
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 13
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

```
Tyr Ser Ala Ser Phe Leu Tyr Ser Gly Val Pro Ser Arg Phe Ser Gly
         50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                     85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
                210

<210> SEQ ID NO 14
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Lys Asp Thr
                 20                  25                  30

Tyr Ile His Trp Val Arg Gln Ala Pro Gly Lys Gly Leu Glu Trp Val
             35                  40                  45

Ala Arg Ile Tyr Pro Thr Asn Gly Tyr Thr Arg Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
                100                 105                 110

Gly Thr Leu Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190
```

```
Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
        435                 440                 445

Gly

<210> SEQ ID NO 15
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Val His Ser Asp Ile Gln Met Thr Gln Ser Pro Ser Ser Leu Ser Ala
1               5                   10                  15

Ser Val Gly Asp Arg Val Thr Ile Thr Cys Lys Ala Ser Gln Asp Val
            20                  25                  30

Ser Ile Gly Val Ala Trp Tyr Gln Gln Lys Pro Gly Lys Ala Pro Lys
        35                  40                  45

Leu Leu Ile Tyr Ser Ala Ser Tyr Arg Tyr Thr Gly Val Pro Ser Arg
    50                  55                  60

Phe Ser Gly Ser Gly Ser Gly Thr Asp Phe Thr Leu Thr Ile Ser Ser
65                  70                  75                  80

Leu Gln Pro Glu Asp Phe Ala Thr Tyr Tyr Cys Gln Gln Tyr Tyr Ile
                85                  90                  95
```

Tyr Pro Tyr Thr Phe Gly Gln Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 16
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

```
Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
    275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
        340                 345                 350

Leu Pro Pro Ser Arg Glu Glu Met Thr Lys Asn Gln Val Ser Leu Thr
    355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
    435                 440                 445

Lys

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Asp or Ser

<400> SEQUENCE: 17

Gly Phe Thr Phe Thr Asp Tyr Thr Met Xaa
1               5                   10

<210> SEQ ID NO 18
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Asp Val Asn Pro Asn Ser Gly Gly Ser Ile Tyr Asn Gln Arg Phe Lys
1               5                   10                  15

Gly
```

```
<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asn Leu Gly Pro Ser Phe Tyr Phe Asp Tyr
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Lys Ala Ser Gln Asp Val Ser Ile Gly Val Ala
1               5                   10

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Arg or Leu
<220> FEATURE:
<221> NAME/KEY: MOD_RES
<222> LOCATION: (6)..(6)
<223> OTHER INFORMATION: Tyr or Glu
<220> FEATURE:
<221> NAME/KEY: MOD_RES
<222> LOCATION: (7)..(7)
<223> OTHER INFORMATION: Thr or Ser

<400> SEQUENCE: 21

Ser Ala Ser Tyr Xaa Xaa Xaa
1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Gln Tyr Tyr Ile Tyr Pro Tyr Thr
1               5
```